(12) United States Patent
Yamada et al.

(10) Patent No.: US 9,499,516 B2
(45) Date of Patent: Nov. 22, 2016

(54) NITROGEN-CONTAINING HETEROCYCLIC COMPOUND

(71) Applicant: Takeda Pharmaceutical Company Limited, Osaka-shi, Osaka (JP)

(72) Inventors: Masami Yamada, Kanagawa (JP); Shinkichi Suzuki, Kanagawa (JP); Takahiro Sugimoto, Kanagawa (JP); Minoru Nakamura, Kanagawa (JP); Hiroki Sakamoto, Kanagawa (JP); Makoto Kamata, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/013,625

(22) Filed: Feb. 2, 2016

(65) Prior Publication Data
US 2016/0152603 A1 Jun. 2, 2016

Related U.S. Application Data

(63) Continuation of application No. 14/693,342, filed on Apr. 22, 2015, now Pat. No. 9,315,458.

(30) Foreign Application Priority Data

Apr. 23, 2014 (JP) .................. 2014-089585

(51) Int. Cl.
*C07D 209/46* (2006.01)
*C07D 403/10* (2006.01)
*C07D 405/14* (2006.01)
*C07D 403/04* (2006.01)
*C07D 401/10* (2006.01)
*C07D 401/14* (2006.01)
*C07D 401/06* (2006.01)
*C07D 405/04* (2006.01)

(52) U.S. Cl.
CPC ........... *C07D 401/06* (2013.01); *C07D 209/46* (2013.01); *C07D 401/10* (2013.01); *C07D 401/14* (2013.01); *C07D 403/04* (2013.01); *C07D 403/10* (2013.01); *C07D 405/04* (2013.01); *C07D 405/14* (2013.01)

(58) Field of Classification Search
None
See application file for complete search history.

(56) References Cited

U.S. PATENT DOCUMENTS

| 5,025,033 | A | 6/1991 | Goto et al. |
| 5,538,983 | A | 7/1996 | Buxbaum et al. |
| 5,939,437 | A | 8/1999 | Kalindjian et al. |
| 2004/0044023 | A1 | 3/2004 | Cantillon |
| 2004/0215019 | A1 | 10/2004 | Straub et al. |
| 2006/0009414 | A1 | 1/2006 | Frey, II et al. |
| 2008/0039446 | A1 | 2/2008 | Straub et al. |
| 2008/0108659 | A1 | 5/2008 | Gandhi et al. |
| 2008/0227794 | A1 | 9/2008 | Van Wagenen et al. |
| 2009/0111830 | A1 | 4/2009 | Wagenen et al. |
| 2009/0275578 | A1 | 11/2009 | Clayton et al. |
| 2010/0317674 | A1 | 12/2010 | Van Wagenen et al. |
| 2011/0166155 | A1 | 7/2011 | Van Wagenen et al. |
| 2011/0301167 | A1 | 12/2011 | Beshore et al. |
| 2012/0040950 | A1 | 2/2012 | Aronov et al. |
| 2012/0202784 | A1 | 8/2012 | Aronov et al. |
| 2012/0245142 | A1 | 9/2012 | Papeo et al. |
| 2013/0109686 | A1 | 5/2013 | Beshore et al. |
| 2014/0038936 | A1 | 2/2014 | Aronov et al. |
| 2014/0288084 | A1 | 9/2014 | Lindsley et al. |
| 2015/0065498 | A1 | 3/2015 | Kuduk et al. |
| 2015/0307497 | A1 | 10/2015 | Sugimoto et al. |

FOREIGN PATENT DOCUMENTS

EP 0 326 106 8/1989
EP 2 821 401 1/2015

(Continued)

OTHER PUBLICATIONS

Bridges, et al., "Chemical lead optimization of a pan Gq mACHR M1, M3, M5 positive allosteric modulator (PAM) lead. Part II: Development of a potent and highly selective M1 PAM", Bioorganic & Medicinal Chemistry Letters, vol. 20, 2010, pp. 1972-1975.

(Continued)

*Primary Examiner* — Timothy R Rozof
(74) *Attorney, Agent, or Firm* — Hamre, Schumann, Mueller & Larson, P.C.

(57) ABSTRACT

The present invention provides a compound having a cholinergic muscarinic M1 receptor positive allosteric modulator activity and useful as an agent for the prophylaxis or treatment of Alzheimer's disease, schizophrenia, pain, sleep disorder, Parkinson's disease dementia, dementia with Lewy bodies, and the like.

The present invention relates to a compound represented by the formula (I) or a salt thereof.

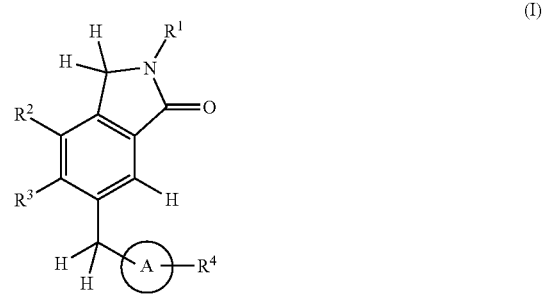

wherein each symbol is as described in the specification, or a salt thereof.

2 Claims, No Drawings

(56) References Cited

FOREIGN PATENT DOCUMENTS

| JP | 44-016647 | 7/1969 |
|---|---|---|
| WO | 95/30647 | 11/1995 |
| WO | 98/30243 | 7/1998 |
| WO | 01/82932 | 11/2001 |
| WO | 02/03684 | 1/2002 |
| WO | 02/074293 | 9/2002 |
| WO | 02/081446 | 10/2002 |
| WO | 02/081447 | 10/2002 |
| WO | 03/011858 | 2/2003 |
| WO | 2004/073639 | 9/2004 |
| WO | 2004/087158 | 10/2004 |
| WO | 2006/020879 | 2/2006 |
| WO | 2006/113485 | 10/2006 |
| WO | 2007/025177 | 3/2007 |
| WO | 2007/125287 | 11/2007 |
| WO | 2007/125290 | 11/2007 |
| WO | 2007/125293 | 11/2007 |
| WO | 2007/139464 | 12/2007 |
| WO | 2008/113072 | 9/2008 |
| WO | 2010/096338 | 8/2010 |
| WO | 2011/006794 | 1/2011 |
| WO | 2011/087776 | 7/2011 |
| WO | 2012/003147 | 1/2012 |
| WO | 2012/149524 | 11/2012 |
| WO | 2012/158475 | 11/2012 |
| WO | 2012/170599 | 12/2012 |
| WO | 2013/063549 | 5/2013 |
| WO | 2013/129622 | 6/2013 |
| WO | 2014/077401 | 5/2014 |
| WO | 2015/028483 | 3/2015 |
| WO | 2015/044072 | 4/2015 |
| WO | 2015/049574 | 4/2015 |

OTHER PUBLICATIONS

Gordon, et al., "A facile, protic ionic liquid route to N-substituted 5-hydroxy-4-methyl-3-oxoisoindoline-1-carboxamides and N-substituted 3-oxoisoindoline-4-carboxylic acids", Green Chemistry, vol. 12, 2010, pp. 1000-1006.

International Search Report issued in corresponding International Application No. PCT/JP2015/062912, Jul. 10, 2015, 4 pages.

NITROGEN-CONTAINING HETEROCYCLIC COMPOUND

TECHNICAL FIELD

The present invention relates to a nitrogen-containing heterocyclic compound which has a cholinergic muscarinic M1 receptor positive allosteric modulator activity and is useful as a medicament such as an agent for the prophylaxis or treatment of Alzheimer's disease, schizophrenia, pain, sleep disorder, Parkinson's disease dementia, dementia with Lewy bodies and the like. As used herein, the positive allosteric modulator activity refers to an action to potentiate receptor function by binding at a different site from that of an endogenous activator (acetylcholine for this receptor).

BACKGROUND OF THE INVENTION

Acetylcholine is a neurotransmitter that induces signal transduction in the central nervous system and the neuromuscular connections (the parasympathetic nerve and motor nerve). In the central nervous system, nuclei of origin of the acetylcholine neuron are in the brain stem and forebrain, and those acetylcholine neurons project to cerebral cortex, hippocampus, and limbic area. In addition, some interneurons in some brain areas such as striatum utilize acetylcholine as a neurotransmitter. Acetylcholine receptor is classified into a ligand dependent-ion channel (cholinergic nicotinic receptor) and a G-protein-coupled receptor (cholinergic muscarinic receptor). The cholinergic muscarinic receptor is one kind of receptor for excitatory neurotransmitter, acetylcholine, and was named based on the selective activation of the receptor by muscarine. The muscarinic receptor is further classified into subtypes of M1 to M5. The M1 receptor is known to be mainly distributed in the brain, and deeply involved particularly in learning, memory, sleep, neuropathic pain, and the like. The importance of cholinergic muscarinic M1 receptor in brain physiology is well known, and a compound which enhances M1 receptor function is expected to be useful as an agent for the prophylaxis or treatment of mental diseases, neurodegenerative diseases, memory disorders, pain, sleep disorders, Parkinson's disease dementia, dementia with Lewy bodies and the like (non-patent document 1).

WO 02/081447 A1 (Patent Document 1) discloses the following compound as a compound having a tumor necrosis factor-α (TNF-α) or a cAMP phosphodiesterase IV (PDE4) inhibitory activity and useful for the prophylaxis or treatment of inflammation and autoimmune disease.

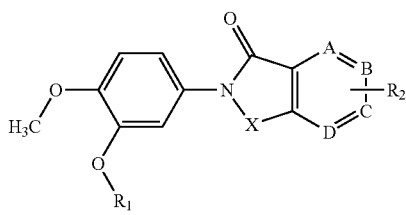

wherein each symbol is as defined in the document.

WO 02/081446 A1 (Patent Document 2) discloses the following compound as a compound having a tumor necrosis factor-α (TNF-α) or a cAMP phosphodiesterase IV (PDE4) inhibitory activity and useful for the prophylaxis or treatment of inflammation and autoimmune disease.

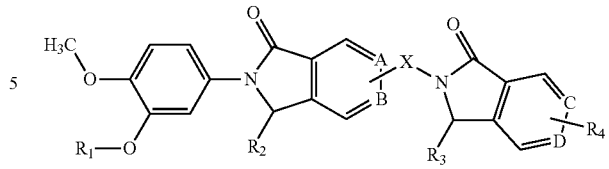

wherein each symbol is as defined in the document.

WO 2006/020879 A1 (Patent Document 3) discloses the following compound as a glutamic acid receptor potentiator useful for the prophylaxis or treatment of psychoneurotic disorder associated with glutamate dysfunction.

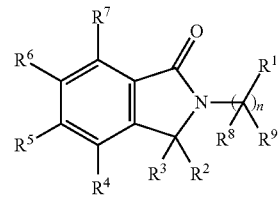

wherein each symbol is as defined in the document.

WO 2013/063549 A1 (Patent Document 4) discloses the following compound as a compound useful for the prophylaxis or treatment of psychoneurotic disorder associated with muscarinic acetylcholine receptor dysfunction.

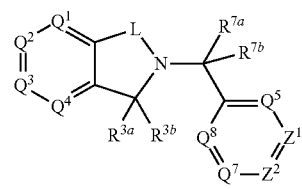

wherein each symbol is as defined in the document.

Bioorganic & Medicinal Chemistry Letters, 20 (2010) 1792-1975 (Non-Patent Document 2) discloses the following compound as an M1 receptor positive allosteric modulator.

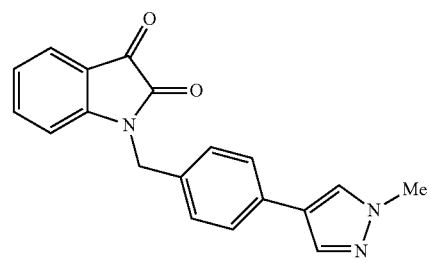 [SMILES: Cn1cc(-c2ccc(CN3C(=O)C(=O)c4ccccc43)cc2)cn1]

Gordon, C. P., Byrne, N., McCluskey, A. Green Chem., 2010, 12, 1000-1006. (Non-Patent Document 3) discloses the following compound similar to the compound of the present invention.

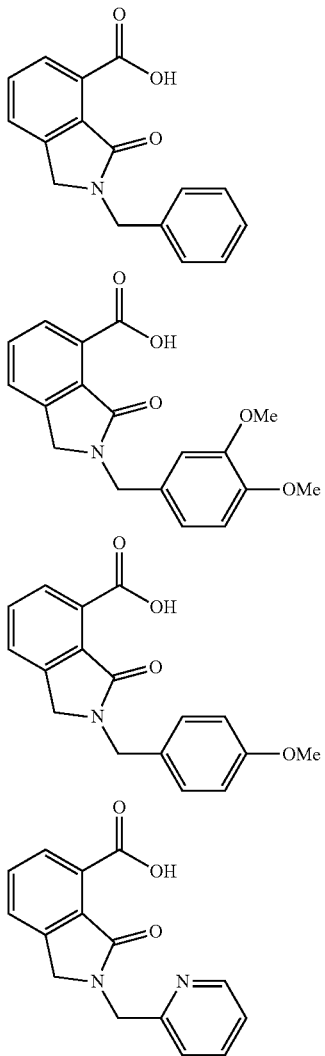

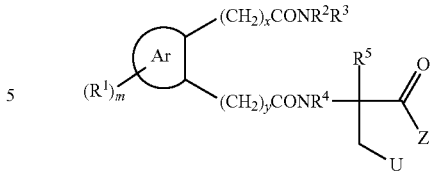

wherein each symbol is as defined in the document.

WO 2007/139464 A1 (Patent Document 7) discloses the following compound as a CB$_1$ receptor ligand useful for the prophylaxis or treatment of pain, cancer, multiple sclerosis, Parkinson's disease, Huntington's disease, Alzheimer's disease, anxiety disorder, gastrointestinal disorder and cardiovascular disorder.

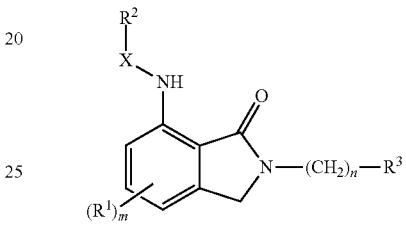

wherein each symbol is as defined in the document.

US 2008/0108659 A1 (Patent Document 8) discloses the following compound as a compound having poly(ADP ribose) polymerase (PARP) activity and useful for the prophylaxis or treatment of cancer, central nervous system disease, inflammation disease and the like.

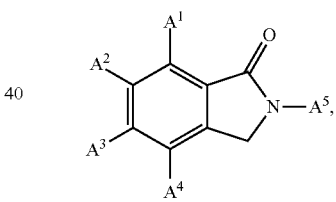

wherein each symbol is as defined in the document.

WO 2011/006794 A1 (Patent Document 9) discloses the following compound as a compound selectively inhibiting an activity of poly (ADP-ribose) polymerase PARP-1 with respect to poly (ADP-ribose) polymerase PARP-2 and useful for the prophylaxis or treatment of cancer, cardiovascular disorder, central nervous system disorder and the like.

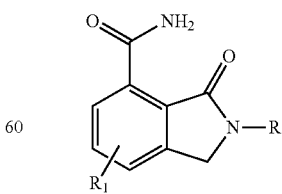

I wherein each symbol is as defined in the document.

WO 2012/003147 A1 (Patent Document 10) discloses the following compound as a compound having an M1PAM WO 2010/096338 A1 (Patent Document 5) discloses the following compound as an M1 receptor positive allosteric modulator useful for the prophylaxis or treatment of a Alzheimer's disease, schizophrenia, pain or sleep disorder.

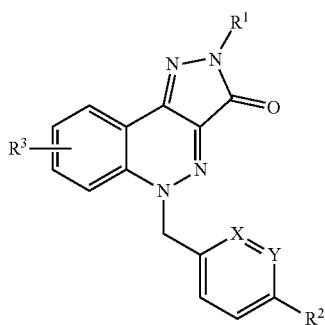

wherein each symbol is as defined in the document.

WO 95/030647 A1 (Patent Document 6) discloses the following compound similar to the compound of the present invention.

activity and useful for the prophylaxis or treatment of Alzheimer's disease, schizophrenia, pain, sleep disorder and the like.

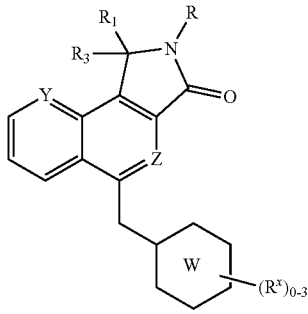

wherein each symbol is as defined in the document.

WO 2012/158475 A1 (Patent Document 11) discloses the following compound as a compound having an M1PAM activity and useful for the prophylaxis or treatment of Alzheimer's disease and other diseases.

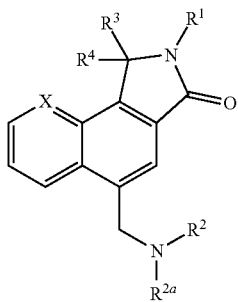

wherein each symbol is as defined in the document.

JP-B-S44-16647 (Patent Document 12) discloses the following compound similar to the compound of the present invention.

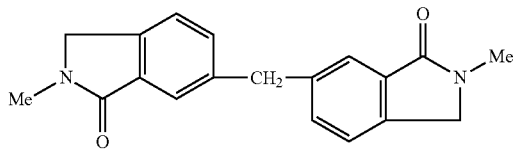 [SMILES: CN1Cc2ccc(Cc3ccc4c(c3)C(=O)N(C)C4)cc2C1=O]

DOCUMENT LIST

Patent Document

Patent Document 1: WO 02/081447 A1
Patent Document 2: WO 02/081446 A1
Patent Document 3: WO 2006/020879 A1
Patent Document 4: WO 2013/063549 A1
Patent Document 5: WO 2010/096338 A1
Patent Document 6: WO 95/030647 A1
Patent Document 7: WO 2007/139464 A1
Patent Document 8: US 2008/0108659 A1
Patent Document 9: WO 2011/006794 A1
Patent Document 10: WO 2012/003147 A1
Patent Document 11: WO 2012/158475 A1
Patent Document 12: JP-B-S44-16647

Non-Patent Document

Non-Patent Document 1: Nature Reviews Drug Discovery, 2007, 6, 721-733.
Non-Patent Document 2: Bioorganic & Medicinal Chemistry Letters, 20 (2010) 1792-1975.
Non-Patent Document 3: Gordon, C. P., Byrne, N., McCluskey, A. Green Chem., 2010, 12, 1000-1006.

SUMMARY OF THE INVENTION

Problems to be Solved by the Invention

The development of a compound having a cholinergic muscarinic M1 receptor (M1 receptor) positive allosteric modulator activity and useful as an agent for the prophylaxis or treatment of for Alzheimer's disease, schizophrenia, pain, sleep disorder, Parkinson's disease dementia, dementia with Lewy bodies and the like is desired. As used herein, the positive allosteric modulator activity refers to an action to potentiate receptor function by binding at a different site from that of an endogenous activator (acetylcholine for this receptor).

Means of Solving the Problems

The present inventors have conducted intensive studies in an attempt to solve the aforementioned problems and found that a compound represented by the following formula (I) has a cholinergic muscarinic M1 receptor positive allosteric modulator activity, which resulted in the completion of the present invention.

Accordingly, the present invention relates to the following.

[1] A compound represented by the formula (I):

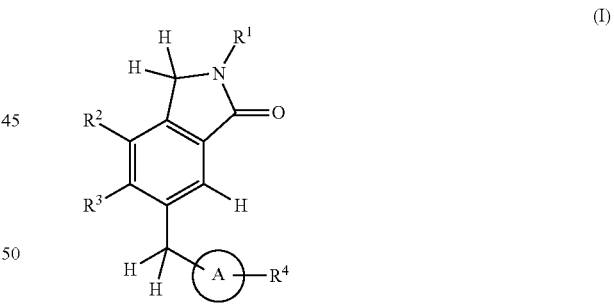

wherein
$R^1$ is an optionally substituted 5- or 6-membered cyclic group or an optionally substituted $C_{1-6}$ alkyl group;
$R^2$ and $R^3$ are the same or different and each is a hydrogen atom, a halogen atom, a cyano group, an optionally substituted $C_{1-6}$ alkyl group, an optionally substituted $C_{1-6}$ alkoxy group or an optionally substituted $C_{3-6}$ cycloalkyl group;
$R^4$ is a halogen atom, a cyano group, an optionally substituted $C_{1-6}$ alkyl group, an optionally substituted $C_{1-6}$ alkoxy group, an optionally substituted carbamoyl group or an optionally substituted 3- to 8-membered cyclic group; and
Ring A is an optionally further substituted 6-membered aromatic ring, or a salt thereof (in the present specification, to be referred to as compound (1)).

[2] The compound of the above-mentioned [1], wherein $R^1$ is
(1) an optionally substituted phenyl group,
(2) an optionally substituted $C_{5-6}$ cycloalkyl group,
(3) an optionally substituted 5- or 6-membered non-aromatic heterocyclic group,
(4) an optionally substituted 5- or 6-membered monocyclic aromatic heterocyclic group, or
(5) an optionally substituted $C_{1-6}$ alkyl group,
or a salt thereof.

[3] The compound of the above-mentioned [1] or [2], wherein $R^4$ is
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group,
or a salt thereof.

[4] The compound of any of the above-mentioned [1] to [3], wherein Ring A is a 6-membered aromatic ring optionally further substituted by 1 to 3 substituents, in addition to $R^4$, selected from
  (a) a halogen atom,
  (b) a $C_{1-6}$ alkyl group, and
  (c) a $C_{1-6}$ alkoxy group,
or a salt thereof.

[5] The compound of any of the above-mentioned [1] to [4], wherein
$R^1$ is
(1) an optionally substituted phenyl group,
(2) an optionally substituted $C_{5-6}$ cycloalkyl group,
(3) an optionally substituted 5- or 6-membered non-aromatic heterocyclic group,
(4) an optionally substituted 5- or 6-membered monocyclic aromatic heterocyclic group, or
(5) an optionally substituted $C_{1-6}$ alkyl group;
$R^2$ is
(1) a hydrogen atom,
(2) a halogen atom, or
(3) an optionally substituted $C_{1-6}$ alkyl group;
$R^3$ is
(1) a hydrogen atom,
(2) a halogen atom,
(3) a cyano group,
(4) an optionally substituted $C_{1-6}$ alkyl group,
(5) a $C_{1-6}$ alkoxy group, or
(6) a $C_{3-6}$ cycloalkyl group;
$R^4$ is
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group; and
  Ring A is a 6-membered aromatic ring optionally further substituted by 1 to 3 substituents, in addition to $R^4$, selected from
  (a) a halogen atom,
  (b) a $C_{1-6}$ alkyl group, and
  (c) a $C_{1-6}$ alkoxy group,
or a salt thereof.

[6] The compound of any of the above-mentioned [1] to [5], wherein
$R^1$ is
(1) a phenyl group optionally substituted by 1 to 3 substituents selected from
  (i) a halogen atom, and
  (ii) a cyano group,
(2) a $C_{5-6}$ cycloalkyl group optionally substituted by 1 to 3 substituents selected from
  (i) a hydroxy group,
  (ii) a $C_{1-6}$ alkyl group optionally substituted by 1 to 3 hydroxy groups, and
  (iii) a $C_{1-6}$ alkoxy group,
(3) a 5- or 6-membered monocyclic non-aromatic heterocyclic group optionally substituted by 1 to 3 hydroxy groups,
(4) a 5- or 6-membered monocyclic aromatic heterocyclic group optionally substituted by 1 to 3 halogen atoms, or
(5) a $C_{1-6}$ alkyl group optionally substituted by 1 to 3 substituents selected from
  (i) a hydroxy group, and
  (ii) a 3- to 8-membered monocyclic non-aromatic heterocyclic group;
$R^2$ is
(1) a hydrogen atom,
(2) a halogen atom, or
(3) a $C_{1-6}$ alkyl group;
$R^3$ is
(1) a hydrogen atom,
(2) a halogen atom,
(3) a cyano group,
(4) a $C_{1-6}$ alkyl group optionally substituted by 1 to 3 halogen atoms,
(5) a $C_{1-6}$ alkoxy group, or
(6) a $C_{3-6}$ cycloalkyl group;
$R^4$ is
(1) a halogen atom,
(2) a cyano group,
(3) a $C_{1-6}$ alkyl group,
(4) a $C_{1-6}$ alkoxy group optionally substituted by 1 to 3 halogen atoms,
(5) a carbamoyl group,
(6) a mono- or di-$C_{1-6}$ alkyl-carbamoyl group, or
(7) a 5- or 6-membered monocyclic aromatic heterocyclic group optionally substituted by 1 to 3 $C_{1-6}$ alkyl groups; and
  Ring A is a 6-membered aromatic ring optionally further substituted by 1 to 3 substituents, in addition to $R^4$, selected from
  (a) a halogen atom,
  (b) a $C_{1-6}$ alkyl group, and
  (c) a $C_{1-6}$ alkoxy group,
or a salt thereof.

[7] The compound of the above-mentioned [6], wherein the partial structure represented by the following formula:

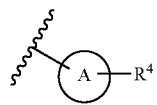

in the formula (I) is a partial structure represented by the following formula:

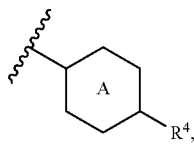

or a salt thereof.

[8] The compound of any of the above-mentioned [1] to [7], wherein
R¹ is
(1) a phenyl group optionally substituted by 1 to 3 substituents selected from
  (i) a halogen atom, and
  (ii) a cyano group,
(2) a $C_{5-6}$ cycloalkyl group optionally substituted by 1 to 3 hydroxy groups,
(3) a 5- or 6-membered monocyclic non-aromatic heterocyclic group optionally substituted by 1 to 3 hydroxy groups, or
(4) a $C_{1-6}$ alkyl group optionally substituted by 1 to 3 substituents selected from
  (i) a hydroxy group, and
  (ii) a 3- to 8-membered monocyclic non-aromatic heterocyclic group;
R² is
(1) a hydrogen atom,
(2) a halogen atom, or
(3) a $C_{1-6}$ alkyl group;
R³ is
(1) a hydrogen atom,
(2) a halogen atom,
(3) a cyano group,
(4) a $C_{1-6}$ alkyl group optionally substituted by 1 to 3 halogen atoms,
(5) a $C_{1-6}$ alkoxy group, or
(6) a $C_{3-6}$ cycloalkyl group;
R⁴ is
(1) a halogen atom,
(2) a cyano group,
(3) a $C_{1-6}$ alkyl group,
(4) a $C_{1-6}$ alkoxy group optionally substituted by 1 to 3 halogen atoms,
(5) a mono- or di-$C_{1-6}$ alkyl-carbamoyl group, or
(6) a 5- or 6-membered monocyclic aromatic heterocyclic group optionally substituted by 1 to 3 $C_{1-6}$ alkyl groups; and
Ring A is a 6-membered aromatic ring optionally further substituted by 1 to 3 substituents, in addition to R⁴, selected from
  (a) a halogen atom, and
  (b) a $C_{1-6}$ alkoxy group,
or a salt thereof.

[9] The compound of the above-mentioned [8], wherein the partial structure represented by the following formula:

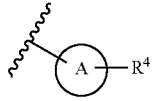

in the formula (I) is a partial structure represented by the following formula:

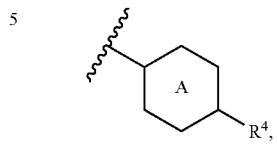

or a salt thereof.

[10] The compound of any of the above-mentioned [1] to [9], wherein
R¹ is
(1) a $C_{5-6}$ cycloalkyl group optionally substituted by 1 to 3 hydroxy groups, or
(2) a 5- or 6-membered monocyclic non-aromatic heterocyclic group optionally substituted by 1 to 3 hydroxy groups;
R² is
(1) a halogen atom, or
(2) a $C_{1-6}$ alkyl group;
R³ is a $C_{1-6}$ alkyl group;
R⁴ is
(1) a $C_{1-6}$ alkyl group,
(2) a $C_{1-6}$ alkoxy group, or
(3) a 5- or 6-membered monocyclic aromatic heterocyclic group; and
Ring A is a benzene ring or a pyridine ring, each of which is unsubstituted, in addition to R⁴,
or a salt thereof.

[11] The compound of the above-mentioned [10], wherein the partial structure represented by the following formula:

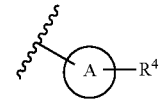

in the formula (I) is a partial structure represented by the following formula:

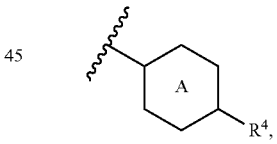

or a salt thereof.

[12] The compound of any of the above-mentioned [1] to [11], wherein
R¹ is
(1) a cyclohexyl group substituted by one hydroxy group, or
(2) a tetrahydropyranyl group substituted by one hydroxy group;
R² is
(1) a halogen atom, or
(2) a $C_{1-6}$ alkyl group;
R³ is a $C_{1-6}$ alkyl group;
R⁴ is
(1) a $C_{1-6}$ alkyl group,
(2) a $C_{1-6}$ alkoxy group, or
(3) a pyrazolyl group; and
Ring A is a benzene ring or a pyridine ring, each of which is unsubstituted, in addition to R⁴,
or a salt thereof.

[13] The compound of the above-mentioned [12], wherein the partial structure represented by the following formula:

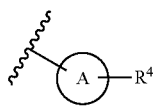

in the formula (I) is a partial structure represented by the following formula:

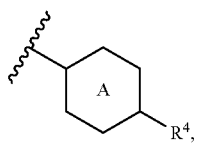

or a salt thereof.

[14] 2-[(3S,4S)-4-Hydroxytetrahydro-2H-pyran-3-yl]-6-(4-methoxybenzyl)-4,5-dimethyl-2,3-dihydro-1H-isoindol-1-one, or a salt thereof.

[15] 4-Fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one, or a salt thereof.

[16] 2-((1S,2S)-2-Hydroxycyclohexyl)-4,5-dimethyl-6-((6-methylpyridin-3-yl)methyl)isoindolin-1-one, or a salt thereof.

[17] A medicament comprising the compound of any of the above-mentioned [1] to [16] or a salt thereof.

[18] The medicament of the above-mentioned [17], which is a cholinergic muscarinic M1 receptor positive allosteric modulator.

[19] The medicament of the above-mentioned [17], which is an agent for the prophylaxis or treatment of Alzheimer's disease, schizophrenia, pain, sleep disorder, Parkinson's disease dementia or dementia with Lewy bodies.

[20] The compound of any of the above-mentioned [1] to [16] or a salt thereof for use in the prophylaxis or treatment of Alzheimer's disease, schizophrenia, pain, sleep disorder, Parkinson's disease dementia or dementia with Lewy bodies.

[21] A method of cholinergic muscarinic M1 receptor positive allosteric modulation in a mammal, which comprises administering an effective amount of the compound of any of the above-mentioned [1] to [16] or a salt thereof to the mammal.

[22] A method for the prophylaxis or treatment of Alzheimer's disease, schizophrenia, pain, sleep disorder, Parkinson's disease dementia or dementia with Lewy bodies in a mammal, which comprises administering an effective amount of the compound of any of the above-mentioned [1] to [16] or a salt thereof to the mammal.

[23] Use of the compound of any of the above-mentioned [1] to [16] or a salt thereof for the production of an agent for the prophylaxis or treatment of Alzheimer's disease, schizophrenia, pain, sleep disorder, Parkinson's disease dementia or dementia with Lewy bodies.

Effect of the Invention

The compound of the present invention has a cholinergic muscarinic M1 receptor positive allosteric modulator activity, and is useful as an agent for the prophylaxis or treatment of, for example, Alzheimer's disease, schizophrenia, pain, sleep disorder, Parkinson's disease dementia, dementia with Lewy bodies and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5 halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5 halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5 halogen atoms.

Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5 halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5 halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{1-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5 halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,

(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and
8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and
9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoylamino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a, 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{1-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

Each symbol in formula (I) is explained below.

$R^1$ is an optionally substituted 5- or 6-membered cyclic group or an optionally substituted $C_{1-6}$ alkyl group.

Examples of the "5- or 6-membered cyclic group" of the "optionally substituted 5- or 6-membered cyclic group" for $R^1$ include a phenyl group, a $C_{5-6}$ cycloalkyl group (cyclopentyl, cyclohexyl), a $C_{5-6}$ cycloalkenyl group (cyclopentenyl, cyclohexenyl), a 5- or 6-membered monocyclic aromatic heterocyclic group, a 5- or 6-membered monocyclic non-aromatic heterocyclic group and the like.

Examples of the "5- or 6-membered monocyclic aromatic heterocyclic group" exemplified as the "5- or 6-membered cyclic group" include a 5- or 6-membered monocyclic aromatic heterocyclic group containing, as a ring-constituting atom besides carbon atom, 1 to 4 heteroatoms selected from a nitrogen atom, a sulfur atom and an oxygen atom, and specific examples thereof include those exemplified as the "5- to 6-membered monocyclic aromatic heterocyclic group", from among the above-mentioned preferable examples of the "aromatic heterocyclic group".

Examples of the "5- or 6-membered monocyclic non-aromatic heterocyclic group" exemplified as the "5- or 6-membered cyclic group" include a 5- or 6-membered monocyclic non-aromatic heterocyclic group containing, as a ring-constituting atom besides carbon atom, 1 to 4 heteroatoms selected from a nitrogen atom, a sulfur atom and an oxygen atom, and specific examples thereof include 5- or 6-membered monocyclic non-aromatic heterocyclic groups such as tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisoxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl and the like.

The "$C_{1-6}$ alkyl group" of the "optionally substituted $C_{1-6}$ alkyl group" and the "5- or 6-membered cyclic group" of the "optionally substituted 5- or 6-membered cyclic group" for $R^1$ each optionally has 1 to 5 (preferably 1 to 3) substituents at substitutable position(s). Examples of the substituent include the above-mentioned Substituent Group A. When the number of the substituents is plural, the respective substituents may be the same or different.

$R^1$ is preferably
(1) an optionally substituted phenyl group,
(2) an optionally substituted $C_{5-6}$ cycloalkyl group,
(3) an optionally substituted 5- or 6-membered non-aromatic heterocyclic group,
(4) an optionally substituted 5- or 6-membered monocyclic aromatic heterocyclic group, or
(5) an optionally substituted $C_{1-6}$ alkyl group.

$R^1$ is more preferably
(1) a phenyl group, a $C_{5-6}$ cycloalkyl group (cyclopentyl, cyclohexyl), a 5- or 6-membered monocyclic non-aromatic heterocyclic group (e.g., tetrahydropyranyl) or a 5- or 6-membered monocyclic aromatic heterocyclic group (e.g., pyridyl), each of which is optionally substituted by 1 to 3 substituents selected from
  (i) a halogen atom (e.g., a fluorine atom, a chlorine atom),
  (ii) a cyano group,
  (iii) a hydroxy group,
  (iv) a $C_{1-6}$ alkyl group (e.g., methyl) optionally substituted by 1 to 3 hydroxy groups, and
  (v) a $C_{1-6}$ alkoxy group (e.g., methoxy), or (2) a $C_{1-6}$ alkyl group (e.g., methyl, isobutyl, 1,2-dimethylpropyl) optionally substituted by 1 to 3 substituents selected from
  (i) a hydroxy group, and
  (ii) a 3- to 14-membered non-aromatic heterocyclic group (preferably a 3- to 8-membered monocyclic non-aromatic heterocyclic group) (e.g., tetrahydrofuryl).

$R^1$ is further more preferably
(1) a phenyl group optionally substituted by 1 to 3 substituents selected from
  (i) a halogen atom (e.g., a fluorine atom), and
  (ii) a cyano group,
(2) a $C_{5-6}$ cycloalkyl group (cyclopentyl, cyclohexyl) optionally substituted by 1 to 3 substituents selected from
  (i) a hydroxy group,
  (ii) a $C_{1-6}$ alkyl group (e.g., methyl) optionally substituted by 1 to 3 hydroxy groups, and
  (iii) a $C_{1-6}$ alkoxy group (e.g., methoxy),
(3) a 5- or 6-membered monocyclic non-aromatic heterocyclic group (e.g., tetrahydropyranyl) optionally substituted by 1 to 3 hydroxy groups,
(4) a 5- or 6-membered monocyclic aromatic heterocyclic group (e.g., pyridyl) optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
  (i) a hydroxy group, and
  (ii) a 3- to 8-membered monocyclic non-aromatic heterocyclic group (e.g., tetrahydrofuryl).

$R^1$ is still more preferably
(1) a phenyl group optionally substituted by 1 to 3 substituents selected from
  (i) a halogen atom (e.g., a fluorine atom), and
  (ii) a cyano group,
(2) a $C_{5-6}$ cycloalkyl group (cyclopentyl, cyclohexyl) optionally substituted by 1 to 3 substituents selected from
  (i) a hydroxy group,
  (ii) a $C_{1-6}$ alkyl group (e.g., methyl) optionally substituted by 1 to 3 hydroxy groups, and
  (iii) a $C_{1-6}$ alkoxy group (e.g., methoxy),
(3) a tetrahydropyranyl group optionally substituted by 1 to 3 hydroxy groups,
(4) a pyridyl group optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
  (i) a hydroxy group, and
  (ii) a tetrahydrofuryl group.

In another embodiment, $R^1$ is more preferably
(1) a phenyl group, a $C_{5-6}$ cycloalkyl group (cyclopentyl, cyclohexyl), a 5- or 6-membered monocyclic non-aromatic heterocyclic group (e.g., tetrahydropyranyl) or a 5- or 6-membered monocyclic aromatic heterocyclic group (e.g., pyridyl), each of which is optionally substituted by 1 to 3 substituents selected from
  (i) a halogen atom (e.g., a fluorine atom, a chlorine atom),
  (ii) a cyano group, and
  (iii) a hydroxy group, or
(2) a $C_{1-6}$ alkyl group (e.g., methyl, isobutyl, 1,2-dimethylpropyl) optionally substituted by 1 to 3 substituents selected from
  (i) a hydroxy group, and
  (ii) a 3- to 14-membered non-aromatic heterocyclic group (preferably a 3- to 8-membered monocyclic non-aromatic heterocyclic group) (e.g., tetrahydrofuryl).

In this embodiment, $R^1$ is further more preferably
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a 5- or 6-membered monocyclic non-aromatic heterocyclic group (e.g., tetrahydropyranyl) optionally substituted by 1 to 3 hydroxy groups,
(4) a 5- or 6-membered monocyclic aromatic heterocyclic group (e.g., pyridyl) optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
   (i) a hydroxy group, and
   (ii) a 3- to 8-membered monocyclic non-aromatic heterocyclic group (e.g., tetrahydrofuryl).

In this embodiment, $R^1$ is still more preferably
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a tetrahydropyranyl group optionally substituted by 1 to 3 hydroxy groups,
(4) a pyridyl group optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
   (i) a hydroxy group, and
   (ii) a tetrahydrofuryl group.

In another embodiment, $R^1$ is preferably
(1) an optionally substituted phenyl group,
(2) an optionally substituted $C_{5-6}$ cycloalkyl group,
(3) an optionally substituted 5- or 6-membered non-aromatic heterocyclic group, or
(4) an optionally substituted $C_{1-6}$ alkyl group.

In this embodiment, $R^1$ is more preferably
(1) a phenyl group, a $C_{5-6}$ cycloalkyl group (cyclopentyl, cyclohexyl) or a 5- or 6-membered monocyclic non-aromatic heterocyclic group (e.g., tetrahydropyranyl), each of which is optionally substituted by 1 to 3 substituents selected from
   (i) a halogen atom (e.g., a fluorine atom),
   (ii) a cyano group, and
   (iii) a hydroxy group, or
(2) a $C_{1-6}$ alkyl group (e.g., methyl, isobutyl) optionally substituted by 1 to 3 substituents selected from
   (i) a hydroxy group, and
   (ii) a 3- to 14-membered non-aromatic heterocyclic group (preferably a 3- to 8-membered monocyclic non-aromatic heterocyclic group) (e.g., tetrahydrofuryl).

In this embodiment, $R^1$ is further more preferably
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a 5- or 6-membered monocyclic non-aromatic heterocyclic group (e.g., tetrahydropyranyl) optionally substituted by 1 to 3 hydroxy groups, or
(4) a $C_{1-6}$ alkyl group (e.g., methyl, isobutyl) optionally substituted by 1 to 3 substituents selected from
   (i) a hydroxy group, and
   (ii) a 3- to 8-membered monocyclic non-aromatic heterocyclic group (e.g., tetrahydrofuryl).

In this embodiment, $R^1$ is still more preferably
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a tetrahydropyranyl group optionally substituted by 1 to 3 hydroxy groups, or
(4) a $C_{1-6}$ alkyl group (e.g., methyl, isobutyl) optionally substituted by 1 to 3 substituents selected from
   (i) a hydroxy group, and
   (ii) a tetrahydrofuryl group.

In another embodiment, $R^1$ is still more preferably
(1) a $C_{5-6}$ cycloalkyl group (e.g., cyclohexyl) optionally substituted by 1 to 3 hydroxy groups, or
(2) a 5- or 6-membered monocyclic non-aromatic heterocyclic group (e.g., tetrahydropyranyl) optionally substituted by 1 to 3 hydroxy groups.

In this embodiment, $R^1$ is even more preferably
(1) a $C_{5-6}$ cycloalkyl group (e.g., cyclohexyl) substituted by 1 to 3 hydroxy groups, or
(2) a 5- or 6-membered monocyclic non-aromatic heterocyclic group (e.g., tetrahydropyranyl) substituted by 1 to 3 hydroxy groups.

In this embodiment, $R^1$ is particularly preferably
(1) a cyclohexyl group substituted by one hydroxy group, or
(2) a tetrahydropyranyl group substituted by one hydroxy group.

$R^2$ and $R^3$ are the same or different and each is a hydrogen atom, a halogen atom, a cyano group, an optionally substituted $C_{1-6}$ alkyl group, an optionally substituted $C_{1-6}$ alkoxy group or an optionally substituted $C_{3-6}$ cycloalkyl group.

Examples of the "$C_{3-6}$ cycloalkyl group" of the "optionally substituted $C_{3-6}$ cycloalkyl group" for $R^2$ or $R^3$ include cyclopropyl, cyclobutyl, cyclopentyl and cyclohexyl.

The "$C_{1-6}$ alkyl group" of the "optionally substituted $C_{1-6}$ alkyl group", the "$C_{1-6}$ alkoxy group" of the "optionally substituted $C_{1-6}$ alkoxy group" and the "$C_{3-6}$ cycloalkyl group" of the "optionally substituted $C_{3-6}$ cycloalkyl group" for $R^2$ or $R^3$ each optionally has 1 to 5 (preferably 1 to 3) substituents at substitutable position(s). Examples of the substituent include the above-mentioned Substituent Group A. When the number of the substituents is plural, the respective substituents may be the same or different.

$R^2$ is preferably
(1) a hydrogen atom,
(2) a halogen atom (e.g., a fluorine atom, a chlorine atom), or
(3) an optionally substituted $C_{1-6}$ alkyl group (e.g., methyl).

$R^2$ is more preferably
(1) a hydrogen atom,
(2) a halogen atom (e.g., a chlorine atom, a fluorine atom), or
(3) a $C_{1-6}$ alkyl group (e.g., methyl).

$R^2$ is further more preferably
(1) a halogen atom (e.g., a fluorine atom), or
(2) a $C_{1-6}$ alkyl group (e.g., methyl).

$R^3$ is preferably
(1) a hydrogen atom,
(2) a halogen atom (e.g., a chlorine atom),
(3) a cyano group, (4) an optionally substituted $C_{1-6}$ alkyl group (e.g., methyl, ethyl),
(5) a $C_{1-6}$ alkoxy group (e.g., methoxy), or
(6) a $C_{3-6}$ cycloalkyl group (e.g., cyclopropyl).

$R^3$ is more preferably
(1) a hydrogen atom,
(2) a halogen atom (e.g., a chlorine atom),
(3) a cyano group,
(4) a $C_{5-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl).

$R^3$ is further more preferably
(1) a hydrogen atom,
(2) a halogen atom (e.g., a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl).

$R^3$ is particularly preferably a $C_{1-6}$ alkyl group (e.g., methyl).

$R^4$ is a halogen atom, a cyano group, an optionally substituted $C_{1-6}$ alkyl group, an optionally substituted $C_{1-6}$ alkoxy group, an optionally substituted carbamoyl group or an optionally substituted 3- to 8-membered cyclic group.

Examples of the "3- to 8-membered cyclic group" of the "optionally substituted 3- to 8-membered cyclic group" for $R^4$ include a phenyl group, a $C_{3-8}$ cycloalkyl group, a $C_{3-8}$ cycloalkenyl group, a 5- or 6-membered monocyclic aromatic heterocyclic group, a 3- to 8-membered monocyclic non-aromatic heterocyclic group and the like, and a 5- or 6-membered monocyclic aromatic heterocyclic group is preferable.

Examples of the "$C_{3-8}$ cycloalkyl group" exemplified as the above-mentioned "3- to 8-membered cyclic group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and the like.

Examples of the "$C_{3-8}$cycloalkenyl group" exemplified as the above-mentioned "3- to 8-membered cyclic group" include cyclopropenyl, cyclobutenyl, cyclopentenyl, cyclohexenyl, cycloheptenyl and cyclooctenyl.

Examples of the "5- or 6-membered monocyclic aromatic heterocyclic group" exemplified as the above-mentioned "3- to 8-membered cyclic group" include a 5- or 6-membered monocyclic aromatic heterocyclic group containing, as a ring-constituting atom besides carbon atom, 1 to 4 heteroatoms selected from a nitrogen atom, a sulfur atom and an oxygen atom, and specific examples thereof include those exemplified as the "5- to 6-membered monocyclic aromatic heterocyclic group", from among the above-mentioned preferable examples of the "aromatic heterocyclic group".

Examples of the "3- to 8-membered monocyclic non-aromatic heterocyclic group" exemplified as the above-mentioned "3- to 8-membered cyclic group" include a 3- to 8-membered monocyclic non-aromatic heterocyclic group containing, as a ring-constituting atom besides carbon atom, 1 to 4 heteroatoms selected from a nitrogen atom, a sulfur atom and an oxygen atom, and specific examples thereof include those exemplified as the "3- to 8-membered monocyclic non-aromatic heterocyclic group", from among the above-mentioned preferable examples of the "non-aromatic heterocyclic group".

The "$C_{1-6}$ alkyl group" of the "optionally substituted $C_{1-6}$ alkyl group", the "$C_{1-6}$ alkoxy group" of the "optionally substituted $C_{1-6}$ alkoxy group" and the "3- to 8-membered cyclic group" of the "optionally substituted 3- to 8-membered cyclic group" for $R^4$ each optionally has 1 to 5 (preferably 1 to 3) substituents at substitutable position(s). Examples of the substituent include the above-mentioned Substituent Group A. When the number of the substituents is plural, the respective substituents may be the same or different.

$R^4$ is preferably bonded to the carbon atom at the p-position (4-position) in the "6-membered aromatic ring" of the "optionally further substituted 6-membered aromatic ring" for Ring A (i.e., at the p-position (4-position) relative to the binding site of the oxoisoindolinylmethyl in the formula (I)).

That is, the partial structure represented by the following formula:

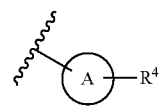

in the formula (I) is preferably a partial structure represented by the following formula:

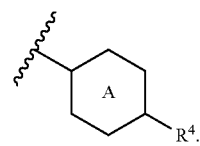

$R^4$ is preferably
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group.

$R^4$ is more preferably
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy, isopropoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 $C_{1-6}$ alkyl groups (e.g., methyl).

$R^4$ is further more preferably
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy, isopropoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl),
(7) a pyrazolyl group optionally substituted by 1 to 3 $C_{1-6}$ alkyl groups (e.g., methyl), (8) a pyridyl group optionally substituted by 1 to 3 $C_{1-6}$ alkyl groups (e.g., methyl),
(9) a triazolyl group optionally substituted by 1 to 3 $C_{1-6}$ alkyl groups (e.g., methyl), or
(10) a pyridazinyl group optionally substituted by 1 to 3 $C_{1-6}$ alkyl groups (e.g., methyl).

In another embodiment, $R^4$ is more preferably
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 $C_{1-6}$ alkyl groups (e.g., methyl).

In this embodiment, $R^4$ is further more preferably
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl),
(7) a pyrazolyl group optionally substituted by 1 to 3 $C_{1-6}$ alkyl groups (e.g., methyl),
(8) a pyridyl group optionally substituted by 1 to 3 $C_{1-6}$ alkyl groups (e.g., methyl),
(9) a triazolyl group optionally substituted by 1 to 3 $C_{1-6}$ alkyl groups (e.g., methyl), or
(10) a pyridazinyl group optionally substituted by 1 to 3 $C_{1-6}$ alkyl groups (e.g., methyl).

In another embodiment, $R^4$ is more preferably
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom),
(5) a mono- or di-$C_{1-6}$ alkyl-carbamoyl group (e.g., methylcarbamoyl), or
(6) a 5- or 6-membered monocyclic aromatic heterocyclic group (e.g., pyrazolyl, pyridyl, triazolyl) optionally substituted by 1 to 3 $C_{1-6}$ alkyl groups (e.g., methyl).

In this embodiment, $R^4$ is further more preferably
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom),
(5) a mono- or di-$C_{1-6}$ alkyl-carbamoyl group (e.g., methylcarbamoyl),
(6) a pyrazolyl group optionally substituted by 1 to 3 $C_{1-6}$ alkyl groups (e.g., methyl),
(7) a pyridyl group optionally substituted by 1 to 3 $C_{1-6}$ alkyl groups (e.g., methyl), or
(8) a triazolyl group optionally substituted by 1 to 3 $C_{1-6}$ alkyl groups (e.g., methyl).

In another embodiment, $R^4$ is further more preferably
(1) a $C_{1-6}$ alkyl group (e.g., methyl),
(2) a $C_{1-6}$ alkoxy group (e.g., methoxy), or
(3) a 5- or 6-membered monocyclic aromatic heterocyclic group (e.g., pyrazolyl).

$R^4$ is particularly preferably
(1) a $C_{1-6}$ alkyl group (e.g., methyl),
(2) a $C_{1-6}$ alkoxy group (e.g., methoxy), or
(3) a pyrazolyl group.

Ring A is an optionally further substituted 6-membered aromatic ring.

Examples of the "6-membered aromatic ring" of the "optionally further substituted 6-membered aromatic ring" for Ring A include a benzene ring, a pyridine ring, a pyridazine ring, a pyrimidine ring, a pyrazine ring, a triazine ring and the like, a benzene ring and a pyridine ring are preferable.

The "6-membered aromatic ring" of the "optionally further substituted 6-membered aromatic ring" for Ring A optionally has 1 to 4 (preferably 1 to 3) substituents, in addition to $R^4$, at substitutable position(s). Examples of the substituent include the above-mentioned Substituent Group A. When the number of the substituents is plural, the respective substituents may be the same or different.

Ring A is preferably a 6-membered aromatic ring (e.g., a benzene ring, a pyridine ring) optionally further substituted by 1 to 3 substituents, in addition to $R^4$, selected from
  (a) a halogen atom (e.g., a fluorine atom),
  (b) a $C_{1-6}$ alkyl group (e.g., methyl),
  (c) a $C_{1-6}$ alkoxy group (e.g., methoxy),
  (d) a cyano group,
  (e) a carbamoyl group,
  (f) a mono- or di-$C_{1-6}$ alkyl-carbamoyl group (e.g., methylcarbamoyl), and
  (g) a 5- to 14-membered aromatic heterocyclic group (preferably a 5- or 6-membered monocyclic aromatic heterocyclic group) (e.g., pyrazolyl, triazolyl) optionally substituted by 1 to 3 $C_{1-6}$ alkyl groups (e.g., methyl).

Ring A is more preferably a 6-membered aromatic ring (e.g., a benzene ring, a pyridine ring) optionally further substituted by 1 to 3 substituents, in addition to $R^4$, selected from
  (a) a halogen atom (e.g., a fluorine atom),
  (b) a $C_{1-6}$ alkyl group (e.g., methyl),
  (c) a $C_{1-6}$ alkoxy group (e.g., methoxy),
  (d) a cyano group,
  (e) a carbamoyl group,
  (f) a mono- or di-$C_{1-6}$ alkyl-carbamoyl group (e.g., methylcarbamoyl),
  (g) a pyrazolyl group optionally substituted by 1 to 3 $C_{1-6}$ alkyl groups (e.g., methyl), and
  (h) a triazolyl group optionally substituted by 1 to 3 $C_{1-6}$ alkyl groups (e.g., methyl).

Ring A is further more preferably
(1) a benzene ring optionally further substituted by 1 to 3 substituents, in addition to $R^4$, selected from
  (a) a halogen atom (e.g., a fluorine atom),
  (b) a $C_{1-6}$ alkyl group (e.g., methyl),
  (c) a $C_{1-6}$ alkoxy group (e.g., methoxy),
  (d) a cyano group,
  (e) a carbamoyl group,
  (f) a mono- or di-$C_{1-6}$ alkyl-carbamoyl group (e.g., methylcarbamoyl),
  (g) a pyrazolyl group optionally substituted by 1 to 3 $C_{1-6}$ alkyl groups (e.g., methyl), and
  (h) a triazolyl group optionally substituted by 1 to 3 $C_{1-6}$ alkyl groups (e.g., methyl), or
(2) a pyridine ring.

In another embodiment, Ring A is preferably a 6-membered aromatic ring (e.g., a benzene ring, a pyridine ring) optionally further substituted by 1 to 3 substituents, in addition to $R^4$, selected from (a) a halogen atom (e.g., a fluorine atom),
(b) a $C_{1-6}$ alkyl group (e.g., methyl),
(c) a $C_{1-6}$ alkoxy group (e.g., methoxy),
(d) a cyano group,
(e) a mono- or di-$C_{1-6}$ alkyl-carbamoyl group (e.g., methylcarbamoyl), and
(f) a 5- to 14-membered aromatic heterocyclic group (preferably a 5- or 6-membered monocyclic aromatic heterocyclic group) (e.g., pyrazolyl).

In this embodiment, Ring A is more preferably a 6-membered aromatic ring (e.g., a benzene ring, a pyridine ring) optionally further substituted by 1 to 3 substituents, in addition to $R^4$, selected from
(a) a halogen atom (e.g., a fluorine atom),
(b) a $C_{1-6}$ alkoxy group (e.g., methoxy),
(c) a cyano group,
(d) a mono- or di-$C_{1-6}$ alkyl-carbamoyl group (e.g., methylcarbamoyl), and
(e) a 5- to 14-membered aromatic heterocyclic group (preferably a 5- or 6-membered monocyclic aromatic heterocyclic group) (e.g., pyrazolyl).

In this embodiment, Ring A is further more preferably a 6-membered aromatic ring (e.g., a benzene ring, a pyridine ring) optionally further substituted by 1 to 3 substituents, in addition to $R^4$, selected from
(a) a halogen atom (e.g., a fluorine atom),
(b) a $C_{1-6}$ alkoxy group (e.g., methoxy),
(c) a cyano group,
(d) a mono- or di-$C_{1-6}$ alkyl-carbamoyl group (e.g., methylcarbamoyl), and
(e) a pyrazolyl group.

In this embodiment, Ring A is still more preferably
(1) a benzene ring optionally further substituted by 1 to 3 substituents, in addition to $R^4$, selected from
(a) a halogen atom (e.g., a fluorine atom),
(b) a $C_{1-6}$ alkoxy group (e.g., methoxy),
(c) a cyano group,
(d) a mono- or di-$C_{1-6}$ alkyl-carbamoyl group (e.g., methylcarbamoyl), and
(e) a pyrazolyl group, or
(2) a pyridine ring.

In another embodiment, Ring A is preferably a 6-membered aromatic ring (e.g., a benzene ring, a pyridine ring) optionally further substituted by 1 to 3 substituents, in addition to $R^4$, selected from
(a) a halogen atom (e.g., a fluorine atom),
(b) a $C_{1-6}$ alkyl group (e.g., methyl), and
(c) a $C_{1-6}$ alkoxy group (e.g., methoxy).

In this embodiment, Ring A is more preferably
(1) a benzene ring optionally further substituted by 1 to 3 substituents, in addition to $R^4$, selected from
(a) a halogen atom (e.g., a fluorine atom),
(b) a $C_{1-6}$ alkyl group (e.g., methyl), and
(c) a $C_{1-6}$ alkoxy group (e.g., methoxy), or
(2) a pyridine ring.

In another embodiment, Ring A is preferably a 6-membered aromatic ring (e.g., a benzene ring, a pyridine ring) optionally further substituted by 1 to 3 substituents, in addition to $R^4$, selected from
(a) a halogen atom (e.g., a fluorine atom), and
(b) a $C_{1-6}$ alkoxy group (e.g., methoxy).

In this embodiment, Ring A is more preferably
(1) a benzene ring optionally further substituted by 1 to 3 substituents, in addition to $R^4$, selected from
(a) a halogen atom (e.g., a fluorine atom), and
(b) a $C_{1-6}$ alkoxy group (e.g., methoxy), or
(2) a pyridine ring.

Ring A is particularly preferably a benzene ring or a pyridine ring, each of which is unsubstituted, in addition to $R^4$.

Preferable examples of compound (I) include the following compounds.

[Compound A-1]
Compound (I) wherein
$R^1$ is
(1) an optionally substituted phenyl group,
(2) an optionally substituted $C_{5-6}$ cycloalkyl group,
(3) an optionally substituted 5- or 6-membered non-aromatic heterocyclic group,
(4) an optionally substituted 5- or 6-membered monocyclic aromatic heterocyclic group, or
(5) an optionally substituted $C_{1-6}$ alkyl group;
$R^2$ is
(1) a hydrogen atom,
(2) a halogen atom (e.g., a fluorine atom, a chlorine atom), or
(3) an optionally substituted $C_{1-6}$ alkyl group (e.g., methyl);
$R^3$ is
(1) a hydrogen atom,
(2) a halogen atom (e.g., a chlorine atom),
(3) a cyano group,
(4) an optionally substituted $C_{1-6}$ alkyl group (e.g., methyl, ethyl),
(5) a $C_{1-6}$ alkoxy group (e.g., methoxy), or
(6) a $C_{3-6}$ cycloalkyl group (e.g., cyclopropyl);
$R^4$ is
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group; and
Ring A is a 6-membered aromatic ring (e.g., a benzene ring, a pyridine ring) optionally further substituted by 1 to 3 substituents, in addition to $R^4$, selected from
(a) a halogen atom (e.g., a fluorine atom),
(b) a $C_{1-6}$ alkyl group (e.g., methyl), and
(c) a $C_{1-6}$ alkoxy group (e.g., methoxy).

In [Compound A-1], the partial structure represented by the following formula:

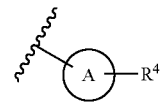

in the formula (I) is preferably a partial structure represented by the following formula:

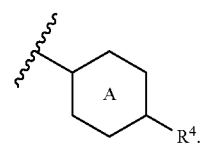

[Compound A-2]
Compound (I) wherein
$R^1$ is
(1) a phenyl group, a $C_{5-6}$ cycloalkyl group (cyclopentyl, cyclohexyl), a 5- or 6-membered monocyclic non-aromatic heterocyclic group (e.g., tetrahydropyranyl) or a 5- or 6-membered monocyclic aromatic heterocyclic group (e.g., pyridyl), each of which is optionally substituted by 1 to 3 substituents selected from
  (i) a halogen atom (e.g., a fluorine atom, a chlorine atom),
  (ii) a cyano group,
  (iii) a hydroxy group,
  (iv) a $C_{1-6}$ alkyl group (e.g., methyl) optionally substituted by 1 to 3 hydroxy groups, and
  (v) a $C_{1-6}$ alkoxy group (e.g., methoxy), or
(2) a $C_{1-6}$ alkyl group (e.g., methyl, isobutyl, 1,2-dimethylpropyl) optionally substituted by 1 to 3 substituents selected from
  (i) a hydroxy group, and
  (ii) a 3- to 14-membered non-aromatic heterocyclic group (preferably a 3- to 8-membered monocyclic non-aromatic heterocyclic group) (e.g., tetrahydrofuryl);
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy, isopropoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 $C_{1-6}$ alkyl groups (e.g., methyl); and
  Ring A is a 6-membered aromatic ring (e.g., a benzene ring, a pyridine ring) optionally further substituted by 1 to 3 substituents, in addition to $R^4$, selected from
  (a) a halogen atom (e.g., a fluorine atom),
  (b) a $C_{1-6}$ alkyl group (e.g., methyl), and
  (c) a $C_{1-6}$ alkoxy group (e.g., methoxy).
  In [Compound A-2], the partial structure represented by the following formula:

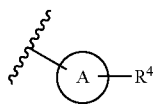

in the formula (I) is preferably a partial structure represented by the following formula:

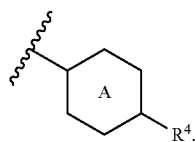

[Compound A-3]
  Compound (I) wherein
  $R^1$ is
(1) a phenyl group optionally substituted by 1 to 3 substituents selected from
  (i) a halogen atom (e.g., a fluorine atom), and
  (ii) a cyano group,
(2) a $C_{1-6}$ cycloalkyl group (cyclopentyl, cyclohexyl) optionally substituted by 1 to 3 substituents selected from
  (i) a hydroxy group,
  (ii) a $C_{1-6}$ alkyl group (e.g., methyl) optionally substituted by 1 to 3 hydroxy groups, and
  (iii) a $C_{1-6}$ alkoxy group (e.g., methoxy),
(3) a 5- or 6-membered monocyclic non-aromatic heterocyclic group (e.g., tetrahydropyranyl) optionally substituted by 1 to 3 hydroxy groups,
(4) a 5- or 6-membered monocyclic aromatic heterocyclic group (e.g., pyridyl) optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
  (i) a hydroxy group, and
  (ii) a 3- to 8-membered monocyclic non-aromatic heterocyclic group (e.g., tetrahydrofuryl);
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy, isopropoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 $C_{1-6}$ alkyl groups (e.g., methyl); and
  Ring A is a 6-membered aromatic ring (e.g., a benzene ring, a pyridine ring) optionally further substituted by 1 to 3 substituents, in addition to $R^4$, selected from
  (a) a halogen atom (e.g., a fluorine atom),
  (b) a $C_{1-6}$ alkyl group (e.g., methyl), and
  (c) a $C_{1-6}$ alkoxy group (e.g., methoxy).

In [Compound A-3], the partial structure represented by the following formula:

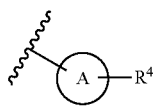

in the formula (I) is preferably a partial structure represented by the following formula:

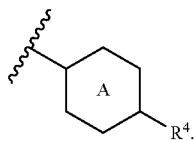

[Compound A-4]
Compound (I) wherein
$R^1$ is
(1) a phenyl group optionally substituted by 1 to 3 substituents selected from
    (i) a halogen atom (e.g., a fluorine atom), and
    (ii) a cyano group,
(2) a $C_{5-6}$ cycloalkyl group (cyclopentyl, cyclohexyl) optionally substituted by 1 to 3 substituents selected from
    (i) a hydroxy group,
    (ii) a $C_{1-6}$ alkyl group (e.g., methyl) optionally substituted by 1 to 3 hydroxy groups, and
    (iii) a $C_{1-6}$ alkoxy group (e.g., methoxy),
(3) a tetrahydropyranyl group optionally substituted by 1 to 3 hydroxy groups,
(4) a pyridyl group optionally substituted by 1 to 3 halogen atoms (e.g., a fluorine atom, a chlorine atom), or
(5) a $C_{1-6}$ alkyl group (e.g., methyl, isobutyl, 1,2-dimethylpropyl) optionally substituted by 1 to 3 substituents selected from
    (i) a hydroxy group, and
    (ii) a tetrahydrofuryl group;
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy, isopropoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl),
(7) a pyrazolyl group optionally substituted by 1 to 3 $C_{1-6}$ alkyl groups (e.g., methyl),
(8) a pyridyl group optionally substituted by 1 to 3 $C_{1-6}$ alkyl groups (e.g., methyl),
(9) a triazolyl group optionally substituted by 1 to 3 $C_{1-6}$ alkyl groups (e.g., methyl), or
(10) a pyridazinyl group optionally substituted by 1 to 3 $C_{1-6}$ alkyl groups (e.g., methyl); and
Ring A is
(1) a benzene ring optionally further substituted by 1 to 3 substituents, in addition to $R^4$, selected from
    (a) a halogen atom (e.g., a fluorine atom),
    (b) a $C_{1-6}$ alkyl group (e.g., methyl), and
    (c) a $C_{1-6}$ alkoxy group (e.g., methoxy), or
(2) a pyridine ring.

In [Compound A-4], the partial structure represented by the following formula:

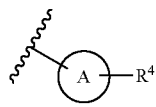

in the formula (I) is preferably a partial structure represented by the following formula:

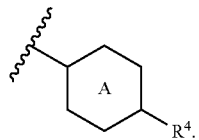

[Compound B-1]
Compound (I) wherein
$R^1$ is
(1) a phenyl group, a $C_{5-6}$ cycloalkyl group (cyclopentyl, cyclohexyl), a 5- or 6-membered monocyclic non-aromatic heterocyclic group (e.g., tetrahydropyranyl) or a 5- or 6-membered monocyclic aromatic heterocyclic group (e.g., pyridyl), each of which is optionally substituted by 1 to 3 substituents selected from
    (i) a halogen atom (e.g., a fluorine atom, a chlorine atom),
    (ii) a cyano group, and
    (iii) a hydroxy group, or
(2) a $C_{1-6}$ alkyl group (e.g., methyl, isobutyl, 1,2-dimethylpropyl) optionally substituted by 1 to 3 substituents selected from
    (i) a hydroxy group, and
    (ii) a 3- to 14-membered non-aromatic heterocyclic group (preferably a 3- to 8-membered monocyclic non-aromatic heterocyclic group) (e.g., tetrahydrofuryl);
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);

R⁴ is
(1) a halogen atom (e.g., a fluorine atom, a chlorine atom),
(2) a cyano group,
(3) a C$_{1-6}$ alkyl group (e.g., methyl, ethyl),
(4) a C$_{1-6}$ alkoxy group (e.g., methoxy, ethoxy) optionally substituted by 1 to 3 halogen atoms (e.g., a fluorine atom),
(5) a carbamoyl group,
(6) a mono- or di-C$_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 C$_{1-6}$ alkyl groups (e.g., methyl); and Ring A is a 6-membered aromatic ring (e.g., a benzene ring, a pyridine ring) optionally further substituted by 1 to 3 substituents, in addition to R⁴, selected from
   (a) a halogen atom (e.g., a fluorine atom),
   (b) a C$_{1-6}$ alkyl group (e.g., methyl), and
   (c) a C$_{1-6}$ alkoxy group (e.g., methoxy).

In [Compound B-1], the partial structure represented by the following formula:

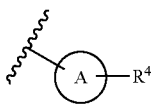

in the formula (I) is preferably a partial structure represented by the following formula:

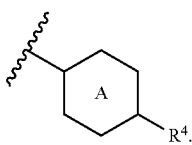

[Compound B-2]
Compound (I) wherein
R¹ is
(1) a phenyl group optionally substituted by 1 to 3 substituents selected from
   (i) a halogen atom (e.g., a fluorine atom), and
   (ii) a cyano group,
(2) a C$_{5-6}$ cycloalkyl group (cyclopentyl, cyclohexyl) optionally substituted by 1 to 3 hydroxy groups,
(3) a 5- or 6-membered monocyclic non-aromatic heterocyclic group (e.g., tetrahydropyranyl) optionally substituted by 1 to 3 hydroxy groups,
(4) a 5- or 6-membered monocyclic aromatic heterocyclic group (e.g., pyridyl) optionally substituted by 1 to 3 halogen atoms (e.g., a fluorine atom, a chlorine atom), or
(5) a C$_{1-6}$ alkyl group (e.g., methyl, isobutyl, 1,2-dimethylpropyl) optionally substituted by 1 to 3 substituents selected from
   (i) a hydroxy group, and
   (ii) a 3- to 8-membered monocyclic non-aromatic heterocyclic group (e.g., tetrahydrofuryl);
R² is
(1) a hydrogen atom,
(2) a halogen atom (e.g., a chlorine atom, a fluorine atom), or
(3) a C$_{1-6}$ alkyl group (e.g., methyl);

R³ is
(1) a hydrogen atom,
(2) a halogen atom (e.g., a chlorine atom),
(3) a cyano group,
(4) a C$_{1-6}$ alkyl group (e.g., methyl, ethyl) optionally substituted by 1 to 3 halogen atoms (e.g., a fluorine atom),
(5) a C$_{1-6}$ alkoxy group (e.g., methoxy), or
(6) a C$_{3-6}$ cycloalkyl group (e.g., cyclopropyl);
R⁴ is
(1) a halogen atom (e.g., a fluorine atom, a chlorine atom),
(2) a cyano group,
(3) a C$_{1-6}$ alkyl group (e.g., methyl, ethyl),
(4) a C$_{1-6}$ alkoxy group (e.g., methoxy, ethoxy) optionally substituted by 1 to 3 halogen atoms (e.g., a fluorine atom),
(5) a carbamoyl group,
(6) a mono- or di-C$_{1-6}$ alkyl-carbamoyl group (e.g., methylcarbamoyl), or
(7) a 5- or 6-membered monocyclic aromatic heterocyclic group (e.g., pyrazolyl, pyridyl, triazolyl, pyridazinyl) optionally substituted by 1 to 3 C$_{1-6}$ alkyl groups (e.g., methyl); and Ring A is a 6-membered aromatic ring (e.g., a benzene ring, a pyridine ring) optionally further substituted by 1 to 3 substituents, in addition to R⁴, selected from
   (a) a halogen atom (e.g., a fluorine atom),
   (b) a C$_{1-6}$ alkyl group (e.g., methyl), and
   (c) a C$_{1-6}$ alkoxy group (e.g., methoxy).

In [Compound B-2], the partial structure represented by the following formula:

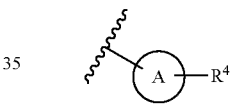

in the formula (I) is preferably a partial structure represented by the following formula:

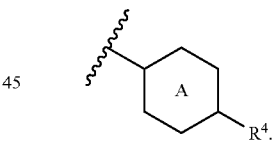

[Compound B-3]
Compound (I) wherein
R¹ is
(1) a phenyl group optionally substituted by 1 to 3 substituents selected from
   (i) a halogen atom (e.g., a fluorine atom), and
   (ii) a cyano group,
(2) a C$_{5-6}$ cycloalkyl group (cyclopentyl, cyclohexyl) optionally substituted by 1 to 3 hydroxy groups,
(3) a tetrahydropyranyl group optionally substituted by 1 to 3 hydroxy groups,
(4) a pyridyl group optionally substituted by 1 to 3 halogen atoms (e.g., a fluorine atom, a chlorine atom), or
(5) a C$_{1-6}$ alkyl group (e.g., methyl, isobutyl, 1,2-dimethylpropyl) optionally substituted by 1 to 3 substituents selected from
   (i) a hydroxy group, and
   (ii) a tetrahydrofuryl group;

$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl, ethyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl, ethyl),
(4) a $C_{1-6}$ alkoxy group (e.g., methoxy, ethoxy) optionally substituted by 1 to 3 halogen atoms (e.g., a fluorine atom),
(5) a carbamoyl group,
(6) a mono- or di-$C_{1-6}$ alkyl-carbamoyl group (e.g., methylcarbamoyl),
(7) a pyrazolyl group optionally substituted by 1 to 3 $C_{1-6}$ alkyl groups (e.g., methyl),
(8) a pyridyl group optionally substituted by 1 to 3 $C_{1-6}$ alkyl groups (e.g., methyl),
(9) a triazolyl group optionally substituted by 1 to 3 $C_{1-6}$ alkyl groups (e.g., methyl), or
(10) a pyridazinyl group optionally substituted by 1 to 3 $C_{1-6}$ alkyl groups (e.g., methyl); and
Ring A is
(1) a benzene ring optionally further substituted by 1 to 3 substituents, in addition to $R^4$, selected from
 (a) a halogen atom (e.g., a fluorine atom),
 (b) a $C_{1-6}$ alkyl group (e.g., methyl), and
 (c) a $C_{1-6}$ alkoxy group (e.g., methoxy), or
(2) a pyridine ring.
In [Compound B-3], the partial structure represented by the following formula:

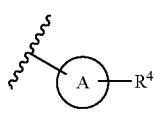

in the formula (I) is preferably a partial structure represented by the following formula:

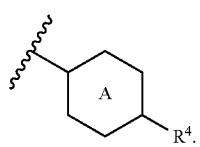

[Compound C-1]
Compound (I) wherein
$R^1$ is
(1) an optionally substituted phenyl group,
(2) an optionally substituted $C_{5-6}$ cycloalkyl group,
(3) an optionally substituted 5- or 6-membered non-aromatic heterocyclic group, or
(4) an optionally substituted $C_{1-6}$ alkyl group;

$R^2$ is
(1) a hydrogen atom,
(2) a halogen atom (e.g., a fluorine atom, a chlorine atom), or
(3) an optionally substituted $C_{1-6}$ alkyl group (e.g., methyl);
$R^3$ is
(1) a hydrogen atom,
(2) a halogen atom (e.g., a chlorine atom),
(3) a cyano group,
(4) an optionally substituted $C_{1-6}$ alkyl group (e.g., methyl),
(5) a $C_{1-6}$ alkoxy group (e.g., methoxy), or
(6) a $C_{3-6}$ cycloalkyl group (e.g., cyclopropyl);
$R^4$ is
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group; and
Ring A is a 6-membered aromatic ring (e.g., a benzene ring, a pyridine ring) optionally further substituted by 1 to 3 substituents, in addition to $R^4$, selected from
 (a) a halogen atom (e.g., a fluorine atom), and
 (b) a $C_{1-6}$ alkoxy group (e.g., methoxy).
[Compound Ca-1]
Compound (I) wherein
$R^1$ is
(1) an optionally substituted phenyl group,
(2) an optionally substituted $C_{5-6}$ cycloalkyl group,
(3) an optionally substituted 5- or 6-membered non-aromatic heterocyclic group, or
(4) an optionally substituted $C_{1-6}$ alkyl group;
$R^2$ is
(1) a hydrogen atom,
(2) a halogen atom (e.g., a fluorine atom, a chlorine atom), or
(3) an optionally substituted $C_{1-6}$ alkyl group (e.g., methyl);
$R^3$ is
(1) a hydrogen atom,
(2) a halogen atom (e.g., a chlorine atom),
(3) a cyano group,
(4) an optionally substituted $C_{1-6}$ alkyl group (e.g., methyl),
(5) a $C_{1-6}$ alkoxy group (e.g., methoxy), or
(6) a $C_{3-6}$ cycloalkyl group (e.g., cyclopropyl);
$R^4$ is
(1) a halogen atom,
(2) a cyano group,
(3) a $C_{1-6}$ alkyl group,
(4) an optionally substituted $C_{1-6}$ alkoxy group,
(5) an optionally substituted carbamoyl group, or
(6) an optionally substituted 5- or 6-membered monocyclic aromatic heterocyclic group;
Ring A is a 6-membered aromatic ring (e.g., a benzene ring, a pyridine ring) optionally further substituted by 1 to 3 substituents, in addition to $R^4$, selected from
 (a) a halogen atom (e.g., a fluorine atom), and
 (b) a $C_{1-6}$ alkoxy group (e.g., methoxy); and
the partial structure represented by the following formula:

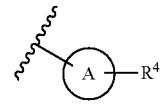

in the formula (I) is a partial structure represented by the following formula:

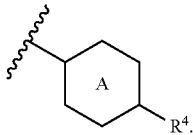

[Compound C-2]
Compound (I) wherein
R$^1$ is
(1) a phenyl group, a C$_{5-6}$ cycloalkyl group (cyclopentyl, cyclohexyl) or a 5- or 6-membered monocyclic non-aromatic heterocyclic group (e.g., tetrahydropyranyl), each of which is optionally substituted by 1 to 3 substituents selected from
   (i) a halogen atom (e.g., a fluorine atom),
   (ii) a cyano group, and
   (iii) a hydroxy group, or
(2) a C$_{1-6}$ alkyl group (e.g., methyl, isobutyl) optionally substituted by 1 to 3 substituents selected from
   (i) a hydroxy group, and
   (ii) a 3- to 14-membered non-aromatic heterocyclic group (preferably a 3- to 8-membered monocyclic non-aromatic heterocyclic group) (e.g., tetrahydrofuryl);
R$^2$ is
(1) a hydrogen atom,
(2) a halogen atom (e.g., a chlorine atom, a fluorine atom), or
(3) a C$_{1-6}$ alkyl group (e.g., methyl);
R$^3$ is
(1) a hydrogen atom,
(2) a halogen atom (e.g., a chlorine atom),
(3) a cyano group,
(4) a C$_{1-6}$ alkyl group (e.g., methyl) optionally substituted by 1 to 3 halogen atoms (e.g., a fluorine atom),
(5) a C$_{1-6}$ alkoxy group (e.g., methoxy), or
(6) a C$_{3-6}$ cycloalkyl group (e.g., cyclopropyl);
R$^4$ is
(1) a halogen atom (e.g., a chlorine atom, a fluorine atom),
(2) a cyano group,
(3) a C$_{1-6}$ alkyl group (e.g., methyl),
(4) a C$_{1-6}$ alkoxy group (e.g., methoxy) optionally substituted by 1 to 3 halogen atoms (e.g., a fluorine atom),
(5) a mono- or di-C$_{1-6}$ alkyl-carbamoyl group (e.g., methylcarbamoyl), or
(6) a 5- or 6-membered monocyclic aromatic heterocyclic group (e.g., pyrazolyl, pyridyl, triazolyl) optionally substituted by 1 to 3 C$_{1-6}$ alkyl groups (e.g., methyl); and
Ring A is a 6-membered aromatic ring (e.g., a benzene ring, a pyridine ring) optionally further substituted by 1 to 3 substituents, in addition to R$^4$, selected from
   (1) a halogen atom (e.g., a fluorine atom), and
   (2) a C$_{1-6}$ alkoxy group (e.g., methoxy).
[Compound Ca-2]
Compound (I) wherein
R$^1$ is
(1) a phenyl group, a C$_{5-6}$ cycloalkyl group (cyclopentyl, cyclohexyl) or a 5- or 6-membered monocyclic non-aromatic heterocyclic group (e.g., tetrahydropyranyl), each of which is optionally substituted by 1 to 3 substituents selected from
   (i) a halogen atom (e.g., a fluorine atom),
   (ii) a cyano group, and
   (iii) a hydroxy group, or
(2) a C$_{1-6}$ alkyl group (e.g., methyl, isobutyl) optionally substituted by 1 to 3 substituents selected from
   (i) a hydroxy group, and
   (ii) a 3- to 14-membered non-aromatic heterocyclic group (preferably a 3- to 8-membered monocyclic non-aromatic heterocyclic group) (e.g., tetrahydrofuryl);
R$^2$ is
(1) a hydrogen atom,
(2) a halogen atom (e.g., a chlorine atom, a fluorine atom), or
(3) a C$_{1-6}$ alkyl group (e.g., methyl);
R$^3$ is
(1) a hydrogen atom,
(2) a halogen atom (e.g., a chlorine atom),
(3) a cyano group,
(4) a C$_{1-6}$ alkyl group (e.g., methyl) optionally substituted by 1 to 3 halogen atoms (e.g., a fluorine atom),
(5) a C$_{1-6}$ alkoxy group (e.g., methoxy), or
(6) a C$_{3-6}$ cycloalkyl group (e.g., cyclopropyl);
R$^4$ is
(1) a halogen atom (e.g., a chlorine atom, a fluorine atom),
(2) a cyano group,
(3) a C$_{1-6}$ alkyl group (e.g., methyl),
(4) a C$_{1-6}$ alkoxy group (e.g., methoxy) optionally substituted by 1 to 3 halogen atoms (e.g., a fluorine atom),
(5) a mono- or di-C$_{1-6}$ alkyl-carbamoyl group (e.g., methylcarbamoyl), or
(6) a 5- or 6-membered monocyclic aromatic heterocyclic group (e.g., pyrazolyl, pyridyl, triazolyl) optionally substituted by 1 to 3 C$_{1-6}$ alkyl groups (e.g., methyl);
Ring A is a 6-membered aromatic ring (e.g., a benzene ring, a pyridine ring) optionally further substituted by 1 to 3 substituents, in addition to R$^4$, selected from
   (1) a halogen atom (e.g., a fluorine atom), and
   (2) a C$_{1-6}$ alkoxy group (e.g., methoxy); and
the partial structure represented by the following formula:

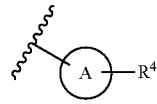

in the formula (I) is a partial structure represented by the following formula:

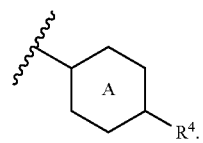

[Compound C-3]
Compound (I) wherein
R$^1$ is
(1) a phenyl group optionally substituted by 1 to 3 substituents selected from
   (i) a halogen atom (e.g., a fluorine atom), and
   (ii) a cyano group,
(2) a C$_{5-6}$ cycloalkyl group (cyclopentyl, cyclohexyl) optionally substituted by 1 to 3 hydroxy groups,
(3) a 5- or 6-membered monocyclic non-aromatic heterocyclic group (e.g., tetrahydropyranyl) optionally substituted by 1 to 3 hydroxy groups, or (4) a $C_{1-6}$ alkyl group (e.g., methyl, isobutyl) optionally substituted by 1 to 3 substituents selected from
   (i) a hydroxy group, and
   (ii) a 3- to 8-membered monocyclic non-aromatic heterocyclic group (e.g., tetrahydrofuryl);
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom),
(5) a mono- or di-$C_{1-6}$ alkyl-carbamoyl group (e.g., methylcarbamoyl), or
(6) a 5- or 6-membered monocyclic aromatic heterocyclic group (e.g., pyrazolyl, pyridyl, triazolyl) optionally substituted by 1 to 3 $C_{1-6}$ alkyl groups (e.g., methyl); and
Ring A is a 6-membered aromatic ring (e.g., a benzene ring, a pyridine ring) optionally further substituted by 1 to 3 substituents, in addition to $R^4$, selected from
(a) a halogen atom (e.g., a fluorine atom), and
(b) a $C_{1-6}$ alkoxy group (e.g., methoxy).
[Compound Ca-3]
Compound (I) wherein
$R^1$ is
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a 5- or 6-membered monocyclic non-aromatic heterocyclic group (e.g., tetrahydropyranyl) optionally substituted by 1 to 3 hydroxy groups, or
(4) a $C_{1-6}$ alkyl group (e.g., methyl, isobutyl) optionally substituted by 1 to 3 substituents selected from
   (i) a hydroxy group, and
   (ii) a 3- to 8-membered monocyclic non-aromatic heterocyclic group (e.g., tetrahydrofuryl);
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom),
(5) a mono- or di-$C_{1-6}$ alkyl-carbamoyl group (e.g., methylcarbamoyl), or
(6) a 5- or 6-membered monocyclic aromatic heterocyclic group (e.g., pyrazolyl, pyridyl, triazolyl) optionally substituted by 1 to 3 $C_{1-6}$ alkyl groups (e.g., methyl);
Ring A is a 6-membered aromatic ring (e.g., a benzene ring, a pyridine ring) optionally further substituted by 1 to 3 substituents, in addition to $R^4$, selected from
(a) a halogen atom (e.g., a fluorine atom), and
(b) a $C_{1-6}$ alkoxy group (e.g., methoxy); and
the partial structure represented by the following formula:

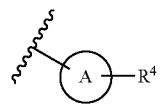

in the formula (I) is a partial structure represented by the following formula:

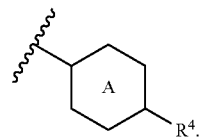

[Compound C-4]
Compound (I) wherein
$R^1$ is
(1) a phenyl group optionally substituted by 1 to 3 substituents selected from
   (i) a halogen atom (e.g., a fluorine atom), and
   (ii) a cyano group,
(2) a $C_{1-6}$ cycloalkyl group (cyclopentyl, cyclohexyl) optionally substituted by 1 to 3 hydroxy groups,
(3) a tetrahydropyranyl group optionally substituted by 1 to 3 hydroxy groups, or
(4) a $C_{1-6}$ alkyl group (e.g., methyl, isobutyl) optionally substituted by 1 to 3 substituents selected from
   (i) a hydroxy group, and
   (ii) a tetrahydrofuryl group;
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom), (5) a mono- or di-$C_{1-6}$ alkyl-carbamoyl group (e.g., methylcarbamoyl),
(6) a pyrazolyl group optionally substituted by 1 to 3 $C_{1-6}$ alkyl groups (e.g., methyl),
(7) a pyridyl group optionally substituted by 1 to 3 $C_{1-6}$ alkyl groups (e.g., methyl), or
(8) a triazolyl group optionally substituted by 1 to 3 $C_{1-6}$ alkyl groups (e.g., methyl); and
Ring A is
(1) a benzene ring optionally further substituted by 1 to 3 substituents, in addition to $R^4$, selected from
   (a) a halogen atom (e.g., a fluorine atom), and
   (b) a $C_{1-6}$ alkoxy group (e.g., methoxy), or
(2) a pyridine ring.

[Compound Ca-4]
Compound (I) wherein
$R^1$ is
(1) a phenyl group optionally substituted by 1 to 3 substituents selected from
   (i) a halogen atom (e.g., a fluorine atom), and
   (ii) a cyano group,
(2) a $C_{5-6}$ cycloalkyl group (cyclopentyl, cyclohexyl) optionally substituted by 1 to 3 hydroxy groups,
(3) a tetrahydropyranyl group optionally substituted by 1 to 3 hydroxy groups, or
(4) a $C_{1-6}$ alkyl group (e.g., methyl, isobutyl) optionally substituted by 1 to 3 substituents selected from
   (i) a hydroxy group, and
   (ii) a tetrahydrofuryl group;
$R^2$ is
(1) a hydrogen atom,
(2) a halogen atom (e.g., a chlorine atom, a fluorine atom), or
(3) a $C_{1-6}$ alkyl group (e.g., methyl);
$R^3$ is
(1) a hydrogen atom,
(2) a halogen atom (e.g., a chlorine atom),
(3) a cyano group,
(4) a $C_{1-6}$ alkyl group (e.g., methyl) optionally substituted by 1 to 3 halogen atoms (e.g., a fluorine atom),
(5) a $C_{1-6}$ alkoxy group (e.g., methoxy), or
(6) a $C_{3-6}$ cycloalkyl group (e.g., cyclopropyl);
$R^4$ is
(1) a halogen atom (e.g., a fluorine atom, a chlorine atom),
(2) a cyano group,
(3) a $C_{1-6}$ alkyl group (e.g., methyl),
(4) a $C_{1-6}$ alkoxy group (e.g., methoxy) optionally substituted by 1 to 3 halogen atoms (e.g., a fluorine atom),
(5) a mono- or di-$C_{1-6}$ alkyl-carbamoyl group (e.g., methylcarbamoyl),
(6) a pyrazolyl group optionally substituted by 1 to 3 $C_{1-6}$ alkyl groups (e.g., methyl),
(7) a pyridyl group optionally substituted by 1 to 3 $C_{1-6}$ alkyl groups (e.g., methyl), or
(8) a triazolyl group optionally substituted by 1 to 3 $C_{1-6}$ alkyl groups (e.g., methyl);
Ring A is
(1) a benzene ring optionally further substituted by 1 to 3 substituents, in addition to $R^4$, selected from
   (a) a halogen atom (e.g., a fluorine atom), and
   (b) a $C_{1-6}$ alkoxy group (e.g., methoxy), or
(2) a pyridine ring; and
the partial structure represented by the following formula:

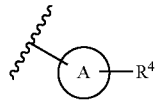

in the formula (I) is a partial structure represented by the following formula:

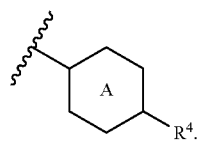

[Compound D-1]
Compound (I) wherein
$R^1$ is
(1) a $C_{5-6}$ cycloalkyl group (e.g., cyclohexyl) optionally substituted by 1 to 3 hydroxy groups, or
(2) a 5- or 6-membered monocyclic non-aromatic heterocyclic group (e.g., tetrahydropyranyl) optionally substituted by 1 to 3 hydroxy groups;
$R^2$ is
(1) a halogen atom (e.g., a fluorine atom), or
(2) a $C_{1-6}$ alkyl group (e.g., methyl);
$R^3$ is a $C_{1-6}$ alkyl group (e.g., methyl);
$R^4$ is
(1) a $C_{1-6}$ alkyl group (e.g., methyl),
(2) a $C_{1-6}$ alkoxy group (e.g., methoxy), or
(3) a 5- or 6-membered monocyclic aromatic heterocyclic group (e.g., pyrazolyl); and
Ring A is a benzene ring or a pyridine ring, each of which is unsubstituted, in addition to $R^4$.

[Compound Da-1]
Compound (I) wherein
$R^1$ is
(1) a $C_{5-6}$ cycloalkyl group (e.g., cyclohexyl) optionally substituted by 1 to 3 hydroxy groups, or
(2) a 5- or 6-membered monocyclic non-aromatic heterocyclic group (e.g., tetrahydropyranyl) optionally substituted by 1 to 3 hydroxy groups;
$R^2$ is
(1) a halogen atom (e.g., a fluorine atom), or
(2) a $C_{1-6}$ alkyl group (e.g., methyl);
$R^3$ is a $C_{1-6}$ alkyl group (e.g., methyl);
$R^4$ is
(1) a $C_{1-6}$ alkyl group (e.g., methyl),
(2) a $C_{1-6}$ alkoxy group (e.g., methoxy), or
(3) a 5- or 6-membered monocyclic aromatic heterocyclic group (e.g., pyrazolyl);
Ring A is a benzene ring or a pyridine ring, each of which is unsubstituted, in addition to $R^4$; and
the partial structure represented by the following formula:

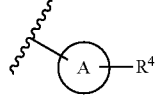

in the formula (I) is a partial structure represented by the following formula:

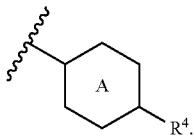

[Compound D-2]
Compound (I) wherein
$R^1$ is
(1) a cyclohexyl group substituted by one hydroxy group, or
(2) a tetrahydropyranyl group substituted by one hydroxy group;
$R^2$ is
(1) a halogen atom (e.g., a fluorine atom), or
(2) a $C_{1-6}$ alkyl group (e.g., methyl);
$R^3$ is a $C_{1-6}$ alkyl group (e.g., methyl);
$R^4$ is
(1) a $C_{1-6}$ alkyl group (e.g., methyl),
(2) a $C_{1-6}$ alkoxy group (e.g., methoxy), or
(3) a pyrazolyl group; and
Ring A is a benzene ring or a pyridine ring, each of which is unsubstituted, in addition to $R^4$.

[Compound Da-2]
Compound (I) wherein
$R^1$ is
(1) a cyclohexyl group substituted by one hydroxy group, or
(2) a tetrahydropyranyl group substituted by one hydroxy group;
$R^2$ is
(1) a halogen atom (e.g., a fluorine atom), or
(2) a $C_{1-6}$ alkyl group (e.g., methyl);
$R^3$ is a $C_{1-6}$ alkyl group (e.g., methyl);
$R^4$ is
(1) a $C_{1-6}$ alkyl group (e.g., methyl),
(2) a $C_{1-6}$ alkoxy group (e.g., methoxy), or
(3) a pyrazolyl group;
Ring A is a benzene ring or a pyridine ring, each of which is unsubstituted, in addition to $R^4$; and
the partial structure represented by the following formula:

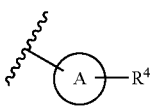

in the formula (I) is a partial structure represented by the following formula:

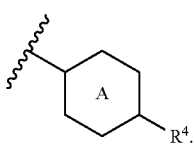

[Compound E]
2-[(3S,4S)-4-Hydroxytetrahydro-2H-pyran-3-yl]-6-(4-methoxybenzyl)-4,5-dimethyl-2,3-dihydro-1H-isoindol-1-one, or a salt thereof 4-Fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one, or a salt thereof
2-((1S,2S)-2-Hydroxycyclohexyl)-4,5-dimethyl-6-((6-methylpyridin-3-yl)methyl)isoindolin-1-one, or a salt thereof When compound (I) is in a form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, preferable examples of the pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are all encompassed in compound (I) of the present invention.

The production methods of the compound of the present invention are explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalents-1 equivalents, preferably 0.01 equivalents-0.2 equivalents, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like;
water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts. inorganic acids: hydrochloric acid, sulfuric acid, nitric acid, hydrobromic acid, phosphoric acid and the like; organic acids: acetic acid, trifluoroacetic acid, citric acid, p-toluenesulfonic acid, 10-camphorsulfonic acid and the like; Lewis acid: boron trifluoride diethyl ether complex, zinc iodide, anhydrous aluminium chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & SonsInc); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, protection or deprotection of functional groups is performed according to a method known per se, for example, the methods described in Wiley-Interscience, 2007, "Protective Groups in Organic Synthesis, 4th Ed." (Theodora W. Greene, Peter G. M. Wuts); Thieme, 2004, "Protecting Groups 3rd Ed." (P. J. Kocienski) and the like, or the methods described in the Examples.

Examples of the protecting group for hydroxyl group of alcohol and the like and phenolic hydroxyl group include ether-type protecting groups such as methoxymethyl ether, benzyl ether, t-butyldimethylsilyl ether, tetrahydropyranyl ether and the like; carboxylate-type protecting groups such as acetate and the like; sulfonate-type protecting groups such as methanesulfonate and the like; carbonate-type protecting groups such as t-butyl carbonate and the like; and the like.

Examples of the protecting group for carbonyl group of aldehyde include acetal-type protecting groups such as dimethyl acetal and the like; cyclic acetal-type protecting groups such as cyclic 1,3-dioxane and the like; and the like.

Examples of the protecting group for carbonyl group of ketone include ketal-type protecting groups such as dimethyl ketal and the like; cyclic ketal-type protecting groups such as cyclic 1,3-dioxane and the like; oxime-type protecting groups such as O-methyloxime and the like; hydrazone-type protecting groups such as N,N-dimethylhydrazone and the like; and the like.

Examples of the protecting group for carboxyl group include ester-type protecting groups such as methyl ester and the like; amide-type protecting groups such as N,N-dimethylamide and the like; and the like.

Examples of the protecting group for thiol include ether-type protecting groups such as benzyl thioether and the like; ester-type protecting groups such as thioacetate, thiocarbonate, thiocarbamate and the like; and the like.

Examples of the protecting group for amino group, and aromatic heterocycle such as imidazole, pyrrole, indole and the like include carbamate-type protecting groups such as benzyl carbamate, tert-butyl carbamate and the like; amide-type protecting groups such as acetamide and the like; alkylamine-type protecting groups such as N-triphenylmethylamine and the like; sulfonamide-type protecting groups such as methanesulfonamide and the like; and the like.

Protecting groups can be removed by a method known per se, for example, methods using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), reduction methods and the like.

When reduction reaction is carried out in each step, examples of the reducing agent to be used include metal hydrides such as lithium aluminium hydride, sodium triacetoxyborohydride, sodium cyanoborohydride, diisobutylaluminium hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodic acids such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., a basic salt, an organic base etc.) are used as a reagent.

When nucleophilic addition reaction by a carbo anion, nucleophilic 1,4-addition reaction (Michael addition reaction) by a carbo anion or nucleophilic displacement reaction by a carbo anion is carried out in each step, examples of the base to be used for generation of the carbo anion include organic lithiums, metal alkoxides, inorganic bases, organic bases and the like.

When Grignard reagent is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or ureation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine) rhodium(III) chloride and the like; cobalt compounds; copper compounds such as copper oxide, copper(I) iodide and the like; platinum compounds and the like. In addition, a base can be added to the reaction system, and examples thereof include inorganic bases, basic salts and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl)phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride, N-phenylbis(trifluoromethanesulfonimide) and the like.

When hydrolysis reaction is carried out in each step, an acid or a base is used as a reagent. For acid hydrolysis reaction of t-butyl ester, formic acid, triethylsilane and the like may be added to reductively-trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced from compound (1) or compound (2) according to the following method.

Scheme (a)

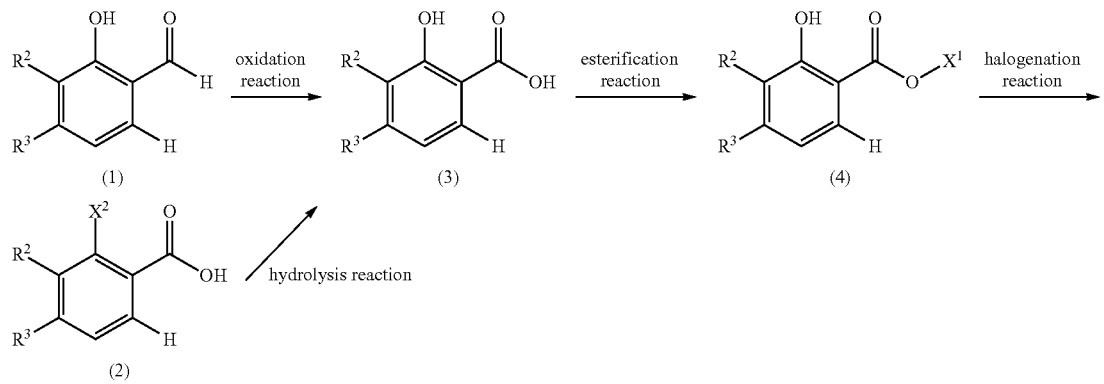

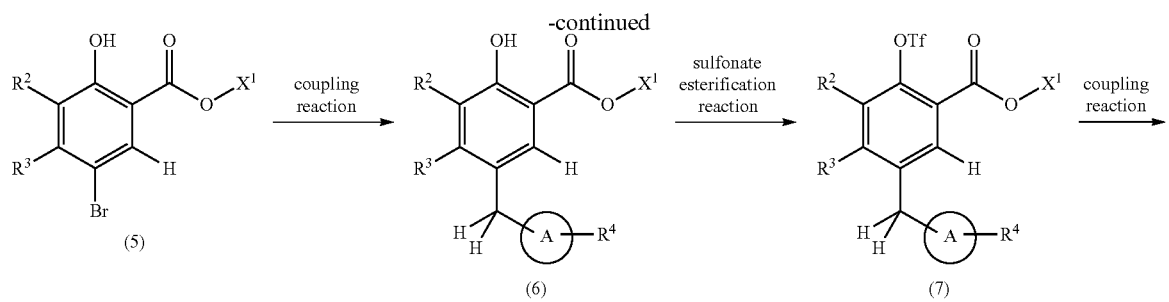

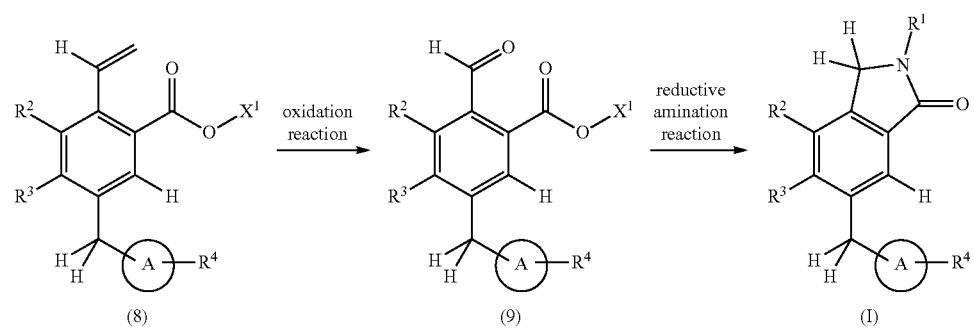

wherein $X^1$ is a $C_{1-6}$ alkyl group (e.g., methyl, ethyl), $X^2$ is a halogen at (e.g., a fluorine atom), and the other symbols are are defined above.

In Scheme (a), compound (3) can be produced by subjecting compound (1) to an oxidation reaction using an oxidant containing manganese such as potassium permanganate and the like, or subjecting compound (2) to a hydrolysis reaction.

Compound (4) can be produced by esterification reaction between compound (3) and alcohols under the acidic conditions with sulfuric acid.

Compound (5) can be produced by subjecting compound (4) to a halogenation reaction using a halogenating agent such as bromine and the like.

Compound (6) can be produced by subjecting compound (5) to a coupling reaction in the presence of a metal catalyst. The reaction may be a two step-reaction via a borate. The halide to be reacted with a borate can be produced according to a method known per se.

Compound (7) can be produced by subjecting compound (6) to a sulfonate esterification reaction using a sulfonating agent.

Compound (8) can be produced by subjecting compound (7) to a coupling reaction in the presence of a palladium compound.

Compound (9) can be produced by subjecting compound (8) to an oxidation reaction.

Compound (I) can be produced by subjecting compound (9) to a reductive amination reaction with an amine using a reducing agent.

Compound (I) can also be produced from compound (6) according to the following method.

Scheme (b)

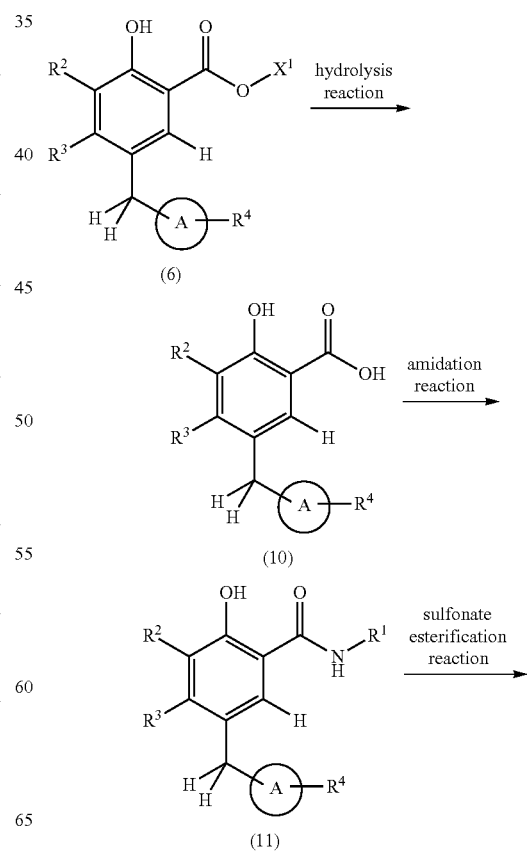

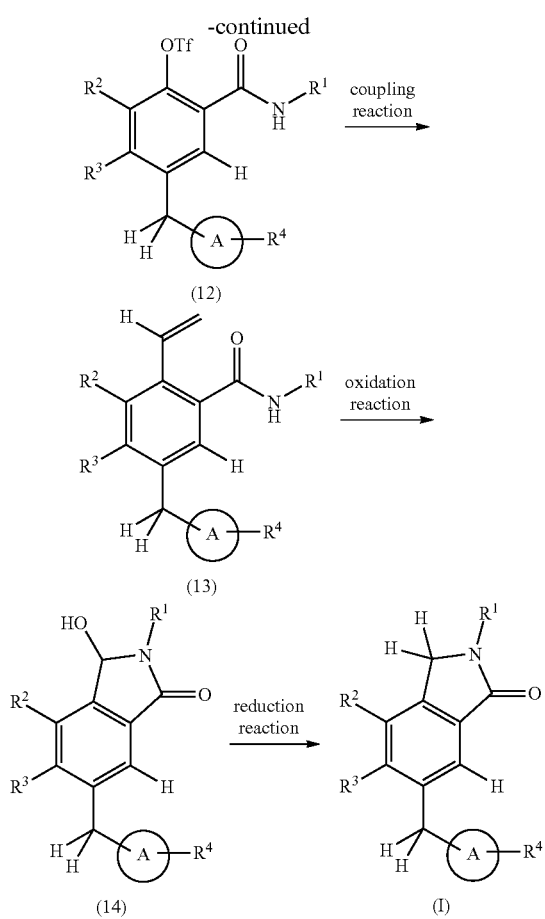

wherein each symbol is as defined above.

In Scheme (b), compound (10) can be produced by subjecting compound (6) to a hydrolysis reaction using an acid or a base.

Compound (11) can be produced by activating compound (10) using an activating agent of a carboxylic acid, and then subjecting the resulting compound to an amidation reaction with an amine.

Compound (12) can be produced by subjecting compound (11) to a sulfonate esterification reaction using a sulfonating agent.

Compound (13) can be produced by subjecting compound (12) to a coupling reaction in the presence of a palladium compound.

Compound (14) can be produced by subjecting compound (13) to an oxidation reaction. In the reaction, the resulting aldehyde is cyclized. Examples of the oxidant to be used include those similar to the oxidant used in the step of producing compound (9) from compound (8) in Scheme (a).

Compound (I) can be produced by subjecting compound (14) to a reduction reaction.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, the optical isomer is obtained using an optically active synthetic intermediate, or subjecting the final racemate product to an optical resolution according to a conventional method.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

When compound (I) is obtained as a free compound, the compound can be converted to an objective salt according to a method known per se or a method analogous thereto. Conversely, when it is obtained in the form of a salt, the salt can be converted to a free form or other objective salt according to a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation or t-butylation, and the like);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation, and the like);

a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be a crystal, and a single crystal form and a mixture of crystal forms are both encompassed in compound (I) of the present invention. The crystal can be produced by crystallizing according to a crystallization method known per se.

Compound (I) is useful for mammals (e.g., mouse, rat, hamster, rabbit, cat, dog, bovine, sheep, monkey, human etc.) as an agent for the prophylaxis or treatment of diseases, for example, (1) psychiatric diseases (e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, autism spectrum syndrome, fragile X syndrome, Rett syndrome, adjustment disorder, bipolar disorder, neurosis, schizophrenia (e.g., positive symptom, negative symptom, and cognitive impairment), cognitive impairment associated with schizophrenia, chronic fatigue syndrome, anxiety neurosis, compulsive neurosis, epilepsy, anxiety symptom, anxious mental state, emotional abnormality, cyclothymia, nervous erethism, faint, addiction, low sex drive, attention deficit hyperactivity disorder (ADHD), psychotic major depression, refractory major depression, treatment-resistant depression], (2) neurodegenerative diseases [e.g., Alzheimer's disease, Alzheimer-type senile dementia, Parkinson's disease, Parkinson's disease dementia, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's syndrome, vascular dementia, postencephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, multiple sclerosis], (3) age-related cognition and memory disorders [e.g., age-related memory disorders, senile dementia]

(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency-syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nerological vomiting, peptic ulcer, diarrhea, constipation, postoperative ileus, stress gastrointestinal disorder, and (7) pain.

A cholinergic muscarinic M1 receptor positive allosteric modulator is particularly preferably useful for the prophylaxis or treatment of Alzheimer's disease, schizophrenia, pain, sleep disorder, Parkinson's disease dementia, dementia with Lewy bodies and the like.

Since compound (I) has a high cholinergic muscarinic M1 receptor positive allosteric modulator activity, it is expected to provide an excellent prophylactic or therapeutic effect for the above-mentioned diseases.

Compound (I) shows excellent solubility in water, the second solution of Japanese Pharmacopeia Elution Test, or the second solution of Japanese Pharmacopoeia Disintegration Test, shows excellent in vivo kinetics (e.g., plasma drug half-life, intracerebral migration, metabolic stability, CYP inhibition), shows low toxicity (e.g., more excellent as a medicament in terms of acute toxicity, chronic toxicity, genetic toxicity, reproductive toxicity, cardiotoxicity, drug interaction, carcinogenicity, phototoxicity, and the like), and also has excellent properties as a pharmaceutical product such as a few side effects. Therefore, compound (I) can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intraorgan, intranasal, intradermal, instillation, intracerebral, intrarectal, intravaginal, intraperitoneal and intratumor administrations, administration to the vicinity of tumor etc. and direct administration to the lesion.

A preparation containing compound (I) may be any of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-H9-263545.

In the preparation of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and safely administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with Alzheimer's disease, the dose is, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

A medicament containing the compound of the present invention can be safely administered solely or by mixing with a pharmaceutically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, $5\text{-HT}_{1A}$ agonist (buspirone hydrochloride, tandospirone citrate, osemozotan hydrochloride etc.), $5\text{-HT}_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), $5\text{-HT}_{2A}$ antagonist, $5\text{-HT}_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, rasagiline, zonisamide, entacapone, amantadine, talipexole, pramipexole, ropinirole, rotigotine, apomorphine, cabergoline, pergolide, bromocriptine, istradefylline, trihexyphenidyl, biperiden, piroheptine, profenamine, promethazine, droxidopa, combination of those drugs etc.), therapeutic drug for Parkinson's disease dementia (rivastigmine), therapeutic drug for dementia with Lewy bodies (donepezil), therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, anti-obesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination drug of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

The "osmium oxide (fixed catalyst I)" in Example means osmium oxide (VIII) (about 7% content) fixed to high solvent resistance polymer, which is commercially available from Wako Pure Chemical Industries, Ltd., unless otherwise specified. In addition, "sodium hydride" means a 60% oil dispersion (mineral mixture).

In the following Examples, the following abbreviations are used.

THF: tetrahydrofuran
DMF: N,N-dimethylformamide
DMSO: dimethyl sulfoxide
NBS: N-bromosuccinimide
AIBN: 2,2'-azobis(isobutyronitrile)
DME: 1,2-dimethoxyethane
$[M+H]^+$: molecular ion peak
M: mol concentration
N: normal concentration
HPLC: high-performance liquid chromatography
tRn (n=1-4): retention time in high-performance liquid chromatography (the number means elution order)

$^1$H NMR (proton nuclear magnetic resonance spectrum) was measured by Fourier-transform NMR. For the analysis, ACD/SpecManager (trade name) and the like were used. Peaks with very mild protons such as a hydroxy group, an amino group and the like are not sometimes described.

MS (mass spectrum) was measured by LC/MS (liquid chromatography mass spectrometer). As Ionization, ESI (Electro Spray Ionization) method, or APCI (Atomospheric Pressure Chemical Ionization) method was used. The data indicates those actual measured value (found). Generally, molecular ion peaks are observed. In the case of a compound having a tert-butoxycarbonyl group (—Boc), a peak after elimination of a tert-butoxycarbonyl group or tert-butyl group may be observed as a fragment ion. In the case of a compound having a hydroxy group (—OH), a peak after elimination of $H_2O$ may be observed as a fragment ion. In the case of a salt, a molecular ion peak or fragment ion peak of free form is generally observed.

Example 1 rac-2-(trans-2-hydroxycyclohexyl)-6-((6-(1-methyl-1H-pyrazol-4-yl)pyridin-3-yl)methyl)isoindolin-1-one A) methyl 5-bromo-2-(bromomethyl)benzoate To a solution of methyl 5-bromo-2-methylbenzoate (5.27 g) in trifluoromethylbenzene (50.0 mL) were added AIBN (0.04 g) and N-bromosuccinimide (4.50 g), and the mixture was stirred at 90° C. for 4 hr under argon atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (4.89 g).

$^1$H NMR (300 MHz, CDCl$_3$) δ 3.95 (3H, s), 4.90 (2H, s), 7.34 (1H, d, J=8.3 Hz), 7.62 (1H, dd, J=8.2, 2.2 Hz), 8.11 (1H, d, J=2.1 Hz).

B) rac-6-bromo-2-(trans-2-hydroxycyclohexyl)isoindolin-1-one

To a solution of methyl 5-bromo-2-(bromomethyl)benzoate (0.50 g) in DMF (5.00 mL) were added trans-2-aminocyclohexanol hydrochloride (0.37 g) and N-ethyldiisopropylamine (1.42 mL), and the mixture was stirred at 80° C. for 3 hr. To the reaction mixture was added 5% aqueous sodium bicarbonate, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (0.22 g).

MS: $[M+H]^+$ 312.0.

C) rac-6-((6-chloropyridin-3-yl)methyl)-2-(trans-2-hydroxycyclohexyl)isoindolin-1-one To a solution of rac-6-bromo-2-(trans-2-hydroxycyclohexyl)isoindolin-1-one (0.23 g) in THF (3.0 mL) were added ((6-chloropyridin-3-yl)methyl)zinc(II) chloride (3.66 mL) and bis(tri-tert-butylphosphine)palladium(0) (0.07 g) under ice-cooling, and the mixture was stirred at room temperature for 3 hr under argon atmosphere. To the reaction mixture were added 5% aqueous sodium bicarbonate and ethyl acetate, the mixture was stirred, and the insoluble substance was removed by filtration. The filtrate was extracted with ethyl acetate, the organic layer was washed with saturated brine, and dried over anhydrous sodium sulfate, and the solvent was evaporated under reduced pressure. The residue was purified by silica gel column chromatography (ethyl acetate/hexane) to give the title compound (0.15 g).

MS: $[M+H]^+$ 357.2.

D) rac-2-(trans-2-hydroxycyclohexyl)-6-((6-(1-methyl-1H-pyrazol-4-yl)pyridin-3-yl)methyl)isoindolin-1-one To a solution of rac-6-((6-chloropyridin-3-yl)methyl)-2-(trans-2-hydroxycyclohexyl)isoindolin-1-one (0.09 g) in a mixed solvent of THF (9.00 mL)-water (3.00 mL) were added 1-methyl-4-(4,4,5,5-tetramethyl-1,3,2-dioxaborolan-2-yl)-1H-pyrazole (0.11 g), cesium carbonate (0.33 g) and bis(tri-tert-butylphosphine)palladium(0) (0.03 g), and the mixture was stirred overnight at 85° C. under argon atmosphere. To the reaction mixture was added water, and the mixture was extracted with ethyl acetate. The organic layer was washed with saturated brine, and dried over anhydrous sodium sulfate, and the solvent was evaporated under reduced pressure. The residue was purified by silica gel column chromatography (methanol/ethyl acetate) to give the title compound (0.03 g).

$^1$H NMR (300 MHz, DMSO-d$_6$) δ 1.27 (3H, brs), 1.53 (1H, brs), 1.66 (3H, brs), 1.94 (1H, brs), 3.54 (1H, brs), 3.78 (1H, d, J=7.0 Hz), 3.86 (3H, s), 4.05 (1H, brs), 4.39 (2H, s), 4.71 (1H, d, J=5.5 Hz), 7.43-7.68 (5H, m), 7.92 (1H, s), 8.21 (1H, s), 8.45 (1H, s).

Example 2 rac-5-chloro-2-(trans-2-hydroxycyclohexyl)-6-(4-(H-pyrazol-1-yl)benzyl)isoindolin-1-one

A) methyl 4-chloro-2-hydroxy-5-(4,4,5,5-tetramethyl-1,3,2-dioxaborolan-2-yl)benzoate To a solution of methyl 5-bromo-4-chloro-2-hydroxybenzoate (2.40 g) in toluene (75.0 mL) were added bis(pinacolato)diboron (3.44 g), potassium acetate (2.66 g) and trans-dichlorobis(triphenylphosphine)palladium(II) (0.32 g), and the mixture was stirred at 110° C. for 14 hr under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (1.34 g).

MS: $[M-H]^+$ 311.1.

B) methyl 5-(4-(1H-pyrazol-1-yl)benzyl)-4-chloro-2-hydroxybenzoate

To a solution of methyl 4-chloro-2-hydroxy-5-(4,4,5,5-tetramethyl-1,3,2-dioxaborolan-2-yl)benzoate (0.15 g) in a mixed solvent of toluene (4.00 mL)-ethanol (0.80 mL)-water (0.80 mL) were added 1-(4-(bromomethyl)phenyl)-1H-pyrazole (0.11 g), tetrakis(triphenylphosphine)palladium(0) (0.06 g) and tripotassium phosphate (0.26 g), and the mixture was stirred overnight at 100° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.06 g).

$^1$H NMR (300 MHz, CDCl$_3$) δ 3.90-3.93 (3H, m), 4.06 (2H, s), 6.41-6.48 (1H, m), 7.07 (1H, s), 7.23 (1H, s), 7.26 (1H, s), 7.57-7.66 (3H, m), 7.71 (1H, d, J=1.5 Hz), 7.89 (1H, d, J=3.0 Hz), 10.69 (1H, s).

C) methyl 5-(4-(1H-pyrazol-1-yl)benzyl)-4-chloro-2-(((trifluoromethyl)sulfonyl)oxy)benzoate To a solution of methyl 5-(4-(1H-pyrazol-1-yl)benzyl)-4-chloro-2-hydroxybenzoate (0.18 g) in DMF (3.00 mL) were added sodium hydride (0.03 g) and N-phenylbis(trifluoromethanesulfonimide) (0.21 g) under ice-cooling, and the mixture was stirred at room temperature for 4 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.18 g).

MS: $[M+H]^+$ 475.0.

D) methyl 5-(4-(1H-pyrazol-1-yl)benzyl)-4-chloro-2-vinylbenzoate

To a solution of methyl 5-(4-(1H-pyrazol-1-yl)benzyl)-4-chloro-2-(((trifluoromethyl)sulfonyl)oxy)benzoate (0.18 g) in DMF (3.50 mL) were added tributylvinyltin (0.17 mL), trans-dichlorobis(triphenylphosphine)palladium(II) (0.01 g) and lithium chloride (0.12 g), and the mixture was stirred at 90° C. for 1 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.13 g).

MS: $[M+H]^+$ 353.1.

E) methyl 5-(4-(1H-pyrazol-1-yl)benzyl)-4-chloro-2-formylbenzoate

To a solution of methyl 5-(4-(1H-pyrazol-1-yl)benzyl)-4-chloro-2-vinylbenzoate (0.12 g) in a mixed solvent of acetone (2.00 mL)-acetonitrile (2.00 mL)-water (2.00 mL) were added osmium oxide (fixed catalyst I) (0.04 g) and sodium periodate (0.36 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound as a crude product. This compound was used in the next step without an additional purification.

F) rac-5-chloro-2-(trans-2-hydroxycyclohexyl)-6-(4-(1H-pyrazol-1-yl)benzyl)isoindolin-1-one A solution of methyl 5-(4-(1H-pyrazol-1-yl)benzyl)-4-chloro-2-formylbenzoate (0.12 g), trans-2-aminocyclohexanol hydrochloride (0.05 g), triethylamine (0.05 mL) and anhydrous magnesium sulfate (0.08 g) in THF (2.50 mL) was stirred at room temperature for 1 hr. The insoluble substance was removed by filtration, and the filtrate was concentrated under reduced pressure. The residue was diluted with methanol (2.50 mL) and THF (2.50 mL), sodium triacetoxyborohydride (0.15 g) was added thereto, and the mixture was stirred at room temperature for 3 hr. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.05 mg).

$^1$H NMR (300 MHz, DMSO-d$_6$) δ 1.23-1.36 (3H, m), 1.48-1.72 (4H, m), 1.89-2.00 (1H, m), 3.49-3.62 (1H, m), 3.74-3.85 (1H, m), 4.20 (2H, s), 4.42 (2H, s), 4.76 (1H, d, J=5.3 Hz), 6.48-6.54 (1H, m), 7.32 (2H, d, J=8.7 Hz), 7.66 (1H, s), 7.69-7.78 (4H, m), 8.43 (1H, d, J=2.6 Hz).

Example 3 rac-2-(trans-2-hydroxycyclohexyl)-5-methoxy-6-(4-(1H-pyrazol-1-yl)benzyl)isoindolin-1-one

A) methyl 5-bromo-2-hydroxy-4-methoxybenzoate

To a solution of 5-bromo-2-hydroxy-4-methoxybenzoic acid (2.00 g) in methanol (10.0 mL) was added 0.6M (diazomethyl)trimethylsilane/hexane solution (14.8 mL) under ice-cooling, and the mixture was stirred for 3 hr. To the reaction mixture was added acetic acid (0.12 mL), and the solvent was evaporated under reduced pressure. The residue was purified by silica gel column chromatography (ethyl acetate/hexane) to give the title compound (2.08 g).

$^1$H NMR (300 MHz, CDCl$_3$) δ 3.91 (3H, s), 3.93 (H, s), 6.49 (1H, s), 7.99 (1H, s), 10.93 (1H, s).

B) methyl 2-hydroxy-4-methoxy-5-(4,4,5,5-tetramethyl-1,3,2-dioxaborolan-2-yl)benzoate To a solution of methyl 5-bromo-2-hydroxy-4-methoxybenzoate (2.08 g) in toluene (70.0 mL) were added bis(pinacolato)diboron (3.03 g), potassium acetate (2.35 g) and trans-dichlorobis(triphenylphosphine)palladium(II) (0.28 g), and the mixture was stirred at 110° C. for 14 hr under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (1.93 g).

MS: [M−H]$^+$ 309.2.

C) methyl 5-(4-(1H-pyrazol-1-yl)benzyl)-2-hydroxy-4-methoxybenzoate

To a solution of methyl 2-hydroxy-4-methoxy-5-(4,4,5,5-tetramethyl-1,3,2-dioxaborolan-2-yl)benzoate (0.80 g) in a mixed solvent of DME (12.0 mL)-water (4.00 mL) were added 1-(4-(bromomethyl)phenyl)-1H-pyrazole (0.62 g), tetrakis(triphenylphosphine)palladium(0) (0.15 g) and sodium carbonate (0.55 g), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.48 g).

MS: [M−H]$^+$ 339.1.

D) methyl 5-(4-(1H-pyrazol-1-yl)benzyl)-4-methoxy-2-(((trifluoromethyl)sulfonyl)oxy)benzoate To a solution of methyl 5-(4-(1H-pyrazol-1-yl)benzyl)-2-hydroxy-4-methoxybenzoate (0.18 g) in DMF (4.00 mL) were added sodium hydride (0.03 g) and N-phenylbis(trifluoromethanesulfonimide)(0.21 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.24 g).

MS: [M+H]$^+$ 471.1.

E) methyl 5-(4-(1H-pyrazol-1-yl)benzyl)-4-methoxy-2-vinylbenzoate

To a solution of methyl 5-(4-(1H-pyrazol-1-yl)benzyl)-4-methoxy-2-(((trifluoromethyl)sulfonyl)oxy)benzoate (0.23 g) in DMF (4.50 mL) were added tributylvinyltin (0.22 mL), trans-dichlorobis(triphenylphosphine)palladium(II) (0.02 g) and lithium chloride (0.16 g), and the mixture was stirred at 90° C. for 1 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.16 g).

MS: [M+H]$^+$ 349.1.

F) methyl 5-(4-(1H-pyrazol-1-yl)benzyl)-2-formyl-4-methoxybenzoate

To a solution of methyl 5-(4-(1H-pyrazol-1-yl)benzyl)-4-methoxy-2-vinylbenzoate (0.16 g) in a mixed solvent of acetone (2.20 mL)-acetonitrile (2.20 mL)-water (2.20 mL) were added osmium oxide (fixed catalyst I) (0.06 g) and sodium periodate (0.48 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.16 g) as a crude product. This compound was used in the next step without an additional purification.

MS: [M+H]$^+$ 351.1.

G) rac-2-(trans-2-hydroxycyclohexyl)-5-methoxy-6-(4-(1H-pyrazol-1-yl)benzyl)isoindolin-1-one A solution of methyl 5-(4-(1H-pyrazol-1-yl)benzyl)-2-formyl-4-methoxybenzoate (0.16 g), trans-2-aminocyclohexanol hydrochloride (0.07 g), triethylamine (0.06 mL) and anhydrous magnesium sulfate (0.10 g) in THF (3.50 mL) was stirred at room temperature for 2 hr. The insoluble substance was removed by filtration, and the filtrate was concentrated under reduced pressure. The residue was diluted with methanol (3.50 mL) and THF (3.50 mL), sodium triacetoxyborohydride (0.19 g) was added thereto, and the mixture was stirred at room temperature for 3.5 hr. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.04 g).

$^1$H NMR (300 MHz, DMSO-d$_6$) δ 1.16-1.36 (3H, m), 1.42-1.74 (4H, m), 1.88-2.00 (1H, m), 3.49-3.63 (1H, m), 3.70-3.83 (1H, m), 3.87 (3H, s), 3.99 (2H, s), 4.37 (2H, s), 4.70 (1H, d, J=5.7 Hz), 6.48-6.53 (1H, m), 7.20 (1H, s), 7.31 (2H, d, J=8.7 Hz), 7.41 (1H, s), 7.67-7.77 (3H, m), 8.42 (1H, d, J=2.6 Hz).

Example 4

2-((1S,2S)-2-hydroxycyclopentyl)-5-methyl-6-(4-(1H-pyrazol-1-yl)benzyl)isoindolin-1-one

A) 5-bromo-2-hydroxy-4-methylbenzoic acid

To a solution of 2-hydroxy-4-methylbenzoic acid (5.00 g) in acetic acid (70.0 mL) was added dropwise bromine (1.68 mL), and the mixture was stirred at room temperature for 5.5 hr. To the reaction mixture was added water, and the precipitate was collected by filtration, and dried under reduced pressure to give the title compound (6.78 g).

MS: [M−H]⁺ 229.0.

B) methyl 5-bromo-2-hydroxy-4-methylbenzoate

To a solution of 5-bromo-2-hydroxy-4-methylbenzoic acid (6.78 g) in methanol (200 mL) was added dropwise sulfuric acid (6.77 mL), and the mixture was stirred overnight at 70° C. The reaction mixture was concentrated under reduced pressure, the residue was neutralized with saturated aqueous sodium bicarbonate solution under ice-cooling, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (6.56 g).

MS: [M−H]⁺ 243.0.

C) methyl 2-hydroxy-4-methyl-5-(4,4,5,5-tetramethyl-1,3,2-dioxaborolan-2-yl)benzoate To a solution of methyl 5-bromo-2-hydroxy-4-methylbenzoate (3.20 g) in toluene (95.0 mL) were added bis(pinacolato)diboron (4.97 g), potassium acetate (3.84 g) and trans-dichlorobis(triphenylphosphine)palladium(II) (0.46 g), and the mixture was stirred at 110° C. for 15 hr under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (3.84 g).

MS: [M+H]⁺ 293.1.

D) methyl 5-(4-(1H-pyrazol-1-yl)benzyl)-2-hydroxy-4-methylbenzoate

To a solution of methyl 2-hydroxy-4-methyl-5-(4,4,5,5-tetramethyl-1,3,2-dioxaborolan-2-yl)benzoate (1.40 g) in a mixed solvent of DME (21.0 mL)-water (7.00 mL) were added 1-(4-(bromomethyl)phenyl)-1H-pyrazole (1.14 g), tetrakis(triphenylphosphine)palladium(0) (0.28 g) and sodium carbonate (1.02 g), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.85 g).

MS: [M+H]⁺ 323.1.

E) methyl 5-(4-(1H-pyrazol-1-yl)benzyl)-4-methyl-2-(((trifluoromethyl)sulfonyl)oxy)benzoate To a solution of methyl 5-(4-(1H-pyrazol-1-yl)benzyl)-2-hydroxy-4-methylbenzoate (0.85 g) in DMF (17.0 mL) were added sodium hydride (0.13 g) and N-phenylbis(trifluoromethanesulfonimide)(1.03 g) under ice-cooling, and the mixture was stirred at room temperature for 3 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (1.13 g).

MS: [M+H]⁺ 455.1.

F) methyl 5-(4-(1H-pyrazol-1-yl)benzyl)-4-methyl-2-vinylbenzoate

To a solution of methyl 5-(4-(1H-pyrazol-1-yl)benzyl)-4-methyl-2-(((trifluoromethyl)sulfonyl)oxy)benzoate (1.12 g) in DMF (25.0 mL) were added tributylvinyltin (1.08 mL), trans-dichlorobis(triphenylphosphine)palladium(II) (0.09 g) and lithium chloride (0.77 g), and the mixture was stirred at 90° C. 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.73 g).

MS: [M+H]⁺ 333.1.

G) methyl 5-(4-(1H-pyrazol-1-yl)benzyl)-2-formyl-4-methylbenzoate

To a solution of methyl 5-(4-(1H-pyrazol-1-yl)benzyl)-4-methyl-2-vinylbenzoate (0.31 g) in a mixed solvent of acetone (6.20 mL)-acetonitrile (6.20 mL)-water (6.20 mL) were added osmium oxide (fixed catalyst I) (0.12 g) and sodium periodate (1.00 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.16 g) as a crude product. This compound was used in the next step without an additional purification.

MS: [M+H]⁺ 335.1.

H) 2-((1S,2S)-2-hydroxycyclopentyl)-5-methyl-6-(4-(1H-pyrazol-1-yl)benzyl)isoindolin-1-one A solution of methyl 5-(4-(1H-pyrazol-1-yl)benzyl)-2-formyl-4-methylbenzoate (0.16 g), (1S,2S)-2-aminocyclopentanol hydrochloride (0.06 g), triethylamine (0.07 mL) and anhydrous magnesium sulfate (0.11 g) in THF (3.10 mL) was stirred at room temperature for 3 hr. The insoluble substance was removed by filtration, and the filtrate was concentrated under reduced pressure. The residue was diluted with methanol (3.10 mL) and THF (3.10 mL), sodium triacetoxyborohydride (0.20 g) was added thereto, and the mixture was stirred overnight at room temperature. The reaction mixture was diluted with ethyl acetate, and the organic layer was washed with water and saturated brine. The organic layer was dried over anhydrous magnesium sulfate, and the solvent was evaporated under reduced pressure. The residue was purified by silica gel column chromatography (ethyl acetate/hexane) to give the title compound (71 mg).

¹H NMR (300 MHz, DMSO-d₆) δ 1.45-1.97 (6H, m), 2.32 (3H, s), 4.00-4.28 (4H, m), 4.40 (2H, s), 4.90 (1H, d, J=4.9 Hz), 6.49-6.56 (1H, m), 7.25 (2H, d, J=8.5 Hz), 7.41 (2H, d, J=12.8 Hz), 7.67-7.81 (3H, m), 8.44 (1H, d, J=2.5 Hz).

Example 5 rac-6-((6-(1,3-dimethyl-1H-pyrazol-4-yl)pyridin-3-yl)methyl)-2-(trans-2-hydroxycyclohexyl)-5-methyl-isoindolin-1-one A) methyl 5-((6-chloropyridin-3-yl)methyl)-2-hydroxy-4-methylbenzoate To a solution of methyl 5-bromo-2-hydroxy-4-methylbenzoate (0.61 g) in THF (20.0 mL) were added 0.5M (2-chloro-5-pyridyl)methylzinc chloride/THF solution (12.5 mL) and bis(tri-tert-butylphosphine)palladium(0) (0.13 g), and the mixture was stirred overnight at room temperature under argon atmosphere. The reaction mixture was concentrated under reduced pressure, and the residue was purified by silica gel column chromatography (ethyl acetate/hexane) to give the title compound (0.52 g).
MS: [M+H]⁺ 292.0.

B) methyl 5-((6-(1,3-dimethyl-1H-pyrazol-4-yl)pyridin-3-yl)methyl)-2-hydroxy-4-methylbenzoate To a solution of methyl 5-((6-chloropyridin-3-yl)methyl)-2-hydroxy-4-methylbenzoate (0.09 g) in a mixed solvent of THF (2.40 mL)-water (0.80 mL) were added 1,3-dimethyl-4-(4,4,5,5-tetramethyl-1,3,2-dioxaborolan-2-yl)-1H-pyrazole (0.14 g), potassium carbonate (0.17 g) and tetrakis(triphenylphosphine)palladium(0) (0.03 g), and the mixture was stirred overnight at 85° C. under argon atmosphere. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.09 g).
MS: [M+H]⁺ 352.1.

C) methyl 5-((6-(1,3-dimethyl-1H-pyrazol-4-yl)pyridin-3-yl)methyl)-4-methyl-2-(((trifluoromethyl)sulfonyl)oxy)benzoate To a solution of methyl 5-((6-(1,3-dimethyl-1H-pyrazol-4-yl)pyridin-3-yl)methyl)-2-hydroxy-4-methylbenzoate (0.27 g) in DMF (6.00 mL) were added sodium hydride (0.04 g) and N-phenylbis(trifluoromethanesulfonimide) (0.30 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.26 g).
MS: [M+H]⁺ 484.1.

D) methyl 5-((6-(1,3-dimethyl-1H-pyrazol-4-yl)pyridin-3-yl)methyl)-4-methyl-2-vinylbenzoate To a solution of methyl 5-((6-(1,3-dimethyl-1H-pyrazol-4-yl)pyridin-3-yl)methyl)-4-methyl-2-(((trifluoromethyl)sulfonyl)oxy)benzoate (0.26 g) in DMF (5.5 mL) were added tributylvinyltin (0.24 mL), trans-dichlorobis(triphenylphosphine)palladium(II) (0.02 g) and lithium chloride (0.17 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.18 g).
MS: [M+H]⁺ 362.1.

E) methyl 5-((6-(1,3-dimethyl-1H-pyrazol-4-yl)pyridin-3-yl)methyl)-2-formyl-4-methylbenzoate To a solution of methyl 5-((6-(1,3-dimethyl-1H-pyrazol-4-yl)pyridin-3-yl)methyl)-4-methyl-2-vinylbenzoate (0.18 g) in a mixed solvent of acetone (2.80 mL)-acetonitrile (2.80 mL)-water (2.80 mL) were added osmium oxide (fixed catalyst I) (0.06 g) and sodium periodate (0.53 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.18 g) as a crude product. This compound was used in the next step without an additional purification.
MS: [M+H]⁺ 364.2.

F) rac-6-((6-(1,3-dimethyl-1H-pyrazol-4-yl)pyridin-3-yl)methyl)-2-(trans-2-hydroxycyclohexyl)-5-methylisoindolin-1-one A solution of methyl 5-((6-(1,3-dimethyl-1H-pyrazol-4-yl)pyridin-3-yl)methyl)-2-formyl-4-methylbenzoate (0.09 g), trans-2-aminocyclohexanol hydrochloride (0.04 g), triethylamine (0.04 mL) and anhydrous magnesium sulfate (0.06 g) in THF (2.00 mL) was stirred at room temperature for 1.5 hr. The insoluble substance was removed by filtration, and the filtrate was concentrated under reduced pressure. The residue was diluted with methanol (2.00 mL) and THF (2.00 mL), sodium triacetoxyborohydride (0.11 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.05 g).
¹H NMR (300 MHz, CDCl₃) δ 1.27-1.59 (5H, m), 1.81 (2H, d, J=11.7 Hz), 1.92 (1H, d, J=13.2 Hz), 2.13-2.24 (1H, m), 2.35 (3H, s), 2.49 (3H, s), 3.61-3.73 (1H, m), 3.87 (3H, s), 4.03 (2H, s), 4.06-4.15 (1H, m), 4.29-4.47 (2H, m), 7.27-7.39 (3H, m), 7.64 (1H, s), 7.76 (1H, s), 8.42 (1H, d, J=1.5 Hz).

Example 6 rac-2-(trans-2-hydroxycyclohexyl)-5-methyl-6-((2'-methyl-2,4'-bipyridin-5-yl)methyl)isoindolin-1-one A) methyl 2-hydroxy-4-methyl-5-((2'-methyl-[2,4'-bipyridine]-5-yl)methyl)benzoate To a solution of methyl 5-((6-chloropyridin-3-yl)methyl)-2-hydroxy-4-methylbenzoate (0.35 g) in a mixed solvent of THF (8.40 mL)-water (2.80 mL) were added 2-methyl-4-(4,4,5,5-tetramethyl-1,3,2-dioxaborolan-2-yl)pyridine (0.53 g), potassium carbonate (0.66 g) and tetrakis(triphenylphosphine)palladium(0) (0.14 g), and the mixture was stirred overnight at 85° C. under argon atmosphere. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.35 g).

MS: [M+H]$^+$ 349.1.

B) methyl 4-methyl-5-((2'-methyl-[2,4'-bipyridine]-5-yl)methyl)-2-(((trifluoromethyl)sulfonyl)oxy)benzoate To a solution of methyl 2-hydroxy-4-methyl-5-((2'-methyl-[2,4'-bipyridine]-5-yl)methyl)benzoate (0.34 g) in DMF (7.00 mL) were added sodium hydride (0.05 g) and N-phenylbis(trifluoromethanesulfonimide) (0.39 g) under ice-cooling, and the mixture was stirred at room temperature for 2.5 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.22 g).

MS: [M+H]$^+$ 481.1.

C) methyl 4-methyl-5-((2'-methyl-[2,4'-bipyridine]-5-yl)methyl)-2-vinylbenzoate

To a solution of methyl 4-methyl-5-((2'-methyl-[2,4'-bipyridine]-5-yl)methyl)-2-(((trifluoromethyl)sulfonyl)oxy)benzoate (0.21 g) in DMF (4.00 mL) were added tributylvinyltin (0.19 mL), trans-dichlorobis(triphenylphosphine)palladium(II) (0.02 g) and lithium chloride (0.14 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.11 g).

MS: [M+H]$^+$ 359.1.

D) methyl 2-formyl-4-methyl-5-((2'-methyl-[2,4'-bipyridine]-5-yl)methyl)benzoate To a solution of methyl 4-methyl-5-((2'-methyl-[2,4'-bipyridine]-5-yl)methyl)-2-vinylbenzoate (0.11 g) in a mixed solvent of acetone (2.00 mL)-acetonitrile (2.00 mL)-water (2.00 mL) were added osmium oxide (fixed catalyst I) (0.04 g) and sodium periodate (0.33 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.11 g) as a crude product. This compound was used in the next step without an additional purification.

MS: [M+H]$^+$ 361.2.

E) rac-2-(trans-2-hydroxycyclohexyl)-5-methyl-6-((2'-methyl-2,4'-bipyridin-5-yl)methyl)isoindolin-1-one A solution of methyl 2-formyl-4-methyl-5-((2'-methyl-[2,4'-bipyridine]-5-yl)methyl)benzoate (0.06 g), trans-2-aminocyclohexanol hydrochloride (0.02 g), triethylamine (0.02 mL) and anhydrous magnesium sulfate (0.04 g) in THF (1.20 mL) was stirred at room temperature for 1.5 hr. The insoluble substance was removed by filtration, and the filtrate was concentrated under reduced pressure. The residue was diluted with methanol (1.20 mL) and THF (1.20 mL), sodium triacetoxyborohydride (0.06 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.02 g).

$^1$H NMR (300 MHz, DMSO-d$_6$) δ 1.23-1.36 (3H, m), 1.45-1.72 (4H, m), 1.90-2.01 (1H, m), 2.35 (3H, s), 2.54 (3H, s), 3.58 (1H, dt, J=11.8, 5.6 Hz), 3.74-3.85 (1H, m), 4.16 (2H, s), 4.38 (2H, s), 4.73 (1H, d, J=5.7 Hz), 7.41 (1H, s), 7.47 (1H, s), 7.66 (1H, dd, J=7.9, 2.3 Hz), 7.81 (1H, d, J=5.3 Hz), 7.90 (1H, s), 8.01 (1H, d, J=8.3 Hz), 8.53 (1H, d, J=5.3 Hz), 8.61 (1H, d, J=1.5 Hz).

Example 7

3-fluoro-2-(5-methyl-1-oxo-6-(4-(1H-pyrazol-1-yl)benzyl)-1,3-dihydro-2H-isoindol-2-yl)benzonitrile A) 6-(4-(1H-pyrazol-1-yl)benzyl)-2-(2,4-dimethoxybenzyl)-5-methylisoindolin-1-one A solution of methyl 5-(4-(1H-pyrazol-1-yl)benzyl)-2-formyl-4-methylbenzoate (0.30 g), (2,4-dimethoxyphenyl)methanamine (0.02 g) and anhydrous magnesium sulfate (0.21 g) in THF (6.00 mL) was stirred at room temperature for 1.5 hr. The insoluble substance was removed by filtration, and the filtrate was concentrated under reduced pressure. The residue was diluted with methanol (6.00 mL) and THF (6.00 mL), sodium triacetoxyborohydride (0.38 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.25 g).

MS: [M+H]$^+$ 454.2.

B) 6-(4-(1H-pyrazol-1-yl)benzyl)-5-methylisoindolin-1-one

To a solution of 6-(4-(1H-pyrazol-1-yl)benzyl)-2-(2,4-dimethoxybenzyl)-5-methylisoindolin-1-one (0.24 g) in trifluoroacetic acid (4.34 mL) was added anisole (0.23 mL), and the mixture was stirred at 80° C. for 2 hr. The reaction mixture was concentrated under reduced pressure, and the residue was purified by silica gel column chromatography (ethyl acetate/hexane) to give the title compound (0.15 g).
MS: [M+H]⁺ 304.1.

C) 3-fluoro-2-(5-methyl-1-oxo-6-(4-(1H-pyrazol-1-yl)benzyl)-1,3-dihydro-2H-isoindol-2-yl)benzonitrile To a solution of 6-(4-(1H-pyrazol-1-yl)benzyl)-5-methyl-isoindolin-1-one (0.05 g) in DMF (1.00 mL) were added potassium carbonate (0.07 g) and 2,3-difluorobenzonitrile (0.05 g), and the mixture was stirred overnight at 150° C. under argon atmosphere. The reaction mixture was diluted with water and ethyl acetate, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) and then HPLC (water/methanol) to give the title compound (7.80 mg).
$^1$H NMR (300 MHz, DMSO-$d_6$) δ 2.39 (3H, s), 4.16 (2H, s), 4.90 (2H, s), 6.50-6.55 (1H, m), 7.31 (2H, d, J=8.5 Hz), 7.54 (1H, s), 7.62 (1H, s), 7.65-7.73 (2H, m), 7.75-7.91 (4H, m), 8.45 (1H, d, J=2.4 Hz).

Example 8

5-methyl-6-(4-(1H-pyrazol-1-yl)benzyl)-2-(tetrahydro-2H-pyran-4-yl)isoindolin-1-one A solution of methyl 5-(4-(1H-pyrazol-1-yl)benzyl)-2-formyl-4-methylbenzoate (0.10 g), tetrahydro-2H-pyran-4-amine (0.03 g) and anhydrous magnesium sulfate (0.07 g) in THF (2.00 mL) was stirred at room temperature for 1 hr. The insoluble substance was removed by filtration, and the filtrate was concentrated under reduced pressure. The residue was diluted with methanol (2.00 mL) and THF (2.00 mL), sodium triacetoxyborohydride (0.13 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.04 g).
$^1$H NMR (300 MHz, DMSO-$d_6$) δ 1.59-1.70 (2H, m), 1.80 (2H, qd, J=12.1, 4.3 Hz), 2.32 (3H, s), 3.3-3.49 (2H, m), 3.94 (2H, dd, J=11.1, 4.0 Hz), 4.09 (2H, s), 4.18-4.29 (1H, m), 4.41 (2H, s), 6.49-6.55 (1H, m), 7.25 (2H, d, J=8.3 Hz), 7.42 (2H, d, J=13.9 Hz), 7.70-7.78 (3H, m), 8.44 (1H, d, J=2.6 Hz).

Example 9 rac-5-cyclopropyl-2-(trans-2-hydroxycyclopentyl)-6-(4-(1H-pyrazol-1-yl)benzyl)isoindolin-1-one

A) methyl 4-bromo-2-hydroxybenzoate

To a solution of 4-bromo-2-hydroxybenzoic acid (15.0 g) in methanol (150 mL) was added dropwise thionyl chloride (10.1 mL) under ice-cooling, and the mixture was stirred overnight at 70° C. under argon atmosphere. The reaction mixture was concentrated under reduced pressure, and the residue was purified by silica gel column chromatography (ethyl acetate/hexane) to give the title compound (14.2 g).
$^1$H NMR (300 MHz, DMSO-$d_6$) δ 3.88 (3H, s), 7.10-7.18 (1H, m), 7.21-7.28 (1H, m), 7.69 (1H, d, J=8.3 Hz), 10.65 (1H, s).

B) methyl 4-cyclopropyl-2-hydroxybenzoate

To a solution of methyl 4-bromo-2-hydroxybenzoate (3.00 g) in toluene (30.0 mL) were added tris(dibenzylideneacetone)dipalladium(0) (0.60 g), 2-dicyclohexylphosphino-2',6'-dimethoxybiphenyl (0.53 g), cyclopropylboronic acid (2.79 g) and sodium carbonate (3.44 g), and the mixture was stirred overnight at 100° C. under argon atmosphere. The reaction mixture was diluted with ethyl acetate, and the mixture was washed with water and saturated brine. The organic layer was dried over anhydrous sodium sulfate, and the solvent was evaporated under reduced pressure. The residue was purified by silica gel column chromatography (ethyl acetate/hexane) to give the title compound (1.80 g).
$^1$H NMR (300 MHz, DMSO-$d_6$) δ 0.70-0.80 (2H, m), 0.97-1.07 (2H, m), 1.85-1.99 (1H, m), 3.87 (3H, s), 6.61-6.73 (2H, m), 7.65 (1H, d, J=7.9 Hz), 10.50 (1H, s).

C) methyl 5-bromo-4-cyclopropyl-2-hydroxybenzoate

To a solution of methyl 4-cyclopropyl-2-hydroxybenzoate (1.80 g) in acetic acid (15.0 mL) was added dropwise bromine (1.57 g) under ice-cooling. The mixture was stirred at room temperature for 2 hr, to the reaction mixture was added water, and the resulting solid was collected by filtration. The obtained solid was dried under reduced pressure to give the title compound (2.28 g).
$^1$H NMR (300 MHz, DMSO-$d_6$) δ 0.69-0.82 (2H, m), 1.02-1.12 (2H, m), 2.04-2.18 (1H, m), 3.87 (3H, s), 6.58 (1H, s), 7.88 (1H, s), 10.38 (1H, s).

D) methyl 4-cyclopropyl-2-hydroxy-5-(4,4,5,5-tetramethyl-1,3,2-dioxaborolan-2-yl)benzoate To a solution of methyl 5-bromo-4-cyclopropyl-2-hydroxybenzoate (1.05 g) in toluene (30 mL) were added bis(pinacolato)diboron (1.48 g), potassium acetate (1.14 g) and trans-dichlorobis(triphenylphosphine)palladium(II) (0.14 g), and the mixture was stirred at 110° C. for 15 hr under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.72 g).
MS: [M+H]⁺ 319.2.

E) methyl 5-(4-(1H-pyrazol-1-yl)benzyl)-4-cyclopropyl-2-hydroxybenzoate

To a solution of methyl 4-cyclopropyl-2-hydroxy-5-(4,4,5,5-tetramethyl-1,3,2-dioxaborolan-2-yl)benzoate (0.36 g) in a mixed solvent of DME (5.70 mL)-water (1.90 mL) were added 1-(4-(bromomethyl)phenyl)-1H-pyrazole (0.27 g), tetrakis(triphenylphosphine)palladium(0) (0.07 g) and sodium carbonate (0.24 g), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.26 g).

MS: [M+H]$^+$ 349.1.

F) methyl 5-(4-(1H-pyrazol-1-yl)benzyl)-4-cyclopropyl-2-(((trifluoromethyl)sulfonyl)oxy)benzoate To a solution of methyl 5-(4-(1H-pyrazol-1-yl)benzyl)-4-cyclopropyl-2-hydroxybenzoate (0.25 g) in DMF (5.00 mL) were added sodium hydride (0.04 g) and N-phenylbis(trifluoromethanesulfonimide)(0.29 g) under ice-cooling, and the mixture was stirred at room temperature for 3 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.33 g).

MS: [M+H]$^+$ 481.1.

G) methyl 5-(4-(1H-pyrazol-1-yl)benzyl)-4-cyclopropyl-2-vinylbenzoate

To a solution of methyl 5-(4-(1H-pyrazol-1-yl)benzyl)-4-cyclopropyl-2-(((trifluoromethyl)sulfonyl)oxy)benzoate (0.33 g) to in DMF (6.60 mL) were added tributylvinyltin (0.30 mL), trans-dichlorobis(triphenylphosphine)palladium (II) (0.02 g) and lithium chloride (0.22 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.22 g).

MS: [M+H]$^+$ 359.2.

H) methyl 5-(4-(1H-pyrazol-1-yl)benzyl)-4-cyclopropyl-2-formylbenzoate

To a solution of methyl 5-(4-(1H-pyrazol-1-yl)benzyl)-4-cyclopropyl-2-vinylbenzoate (0.22 g) in a mixed solvent of acetone (4.40 mL)-acetonitrile (4.40 mL)-water (4.40 mL) were added osmium oxide (fixed catalyst I) (0.08 g) and sodium periodate (0.65 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.22 g) as a crude product. This compound was used in the next step without an additional purification.

MS: [M+H]$^+$ 361.2.

I) rac-5-cyclopropyl-2-(trans-2-hydroxycyclopentyl)-6-(4-(1H-pyrazol-1-yl)benzyl)isoindolin-1-one A solution of methyl 5-(4-(1H-pyrazol-1-yl)benzyl)-4-cyclopropyl-2-formylbenzoate (0.11 g), trans-2-aminocyclopentanol hydrochloride (0.04 g), triethylamine (0.04 mL) and anhydrous magnesium sulfate (0.07 g) in THF (2.20 mL) was stirred at room temperature for 5 hr. The insoluble substance was removed by filtration, and the filtrate was concentrated under reduced pressure. The residue was diluted with methanol (2.20 mL) and THF (2.20 mL), sodium triacetoxyborohydride (0.13 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.06 g).

$^1$H NMR (300 MHz, DMSO-d$_6$) δ 0.62-0.70 (2H, m), 0.89-0.98 (2H, m), 1.47-1.75 (4H, m), 1.79-2.07 (3H, m), 4.06-4.25 (2H, m), 4.27 (2H, s), 4.38 (2H, s), 4.90 (1H, d, J=4.9 Hz), 6.49-6.54 (1H, m), 7.19 (1H, s), 7.28 (2H, d, J=8.3 Hz), 7.44 (1H, s), 7.70-7.78 (3H, m), 8.44 (1H, d, J=2.3 Hz).

Example 10 rac-4-chloro-2-(trans-2-hydroxycyclohexyl)-6-(4-(1H-pyrazol-1-yl)benzyl)-5-(trifluoromethyl)isoindolin-1-one A) 2-chloro-1-(methoxymethoxy)-3-(trifluoromethyl)benzene To a suspension of sodium hydride (3.78 g) in THF (150 mL) were added dropwise 2-chloro-3-hydroxybenzotrifluoride (12.4 g) and chloromethyl methyl ether (6.10 g) under ice-cooling, and the mixture was stirred at 12° C. for 16 hr. The reaction mixture was poured into saturated aqueous sodium chloride solution, and the mixture was extracted with ethyl acetate. The organic layer was dried over anhydrous sodium sulfate, and the solvent was evaporated under reduced pressure to give the title compound (16.8 g) as a crude product.

$^1$H NMR (400 MHz, CDCl$_3$) δ 3.53 (3H, s), 5.28 (2H, s), 7.27-7.32 (1H, m), 7.34-7.39 (2H, m).

B) methyl 3-chloro-2-[(methoxycarbonyl)oxy]-4-(trifluoromethyl)benzoate

To a solution of 2-chloro-1-(methoxymethoxy)-3-(trifluoromethyl)benzene (11.8 g) in THF (100 mL) was added dropwise n-butyllithium (2.5M hexane solution) (21.0 mL) at −10° C., and the mixture was stirred for 2 hr. Then, to the reaction mixture was added dropwise a solution of methyl chloroformate (23.0 g) in THF (50.0 mL), and the mixture was stirred at 10° C. for 16 hr. The reaction mixture was poured into saturated aqueous sodium bicarbonate solution, and the mixture was extracted with ethyl acetate (×2). The organic layer was dried over anhydrous sodium sulfate, and the solvent was evaporated under reduced pressure. The residue was purified by flash silica gel column chromatography (ethyl acetate/petroleum ether) to give the title compound (6.00 g).

$^1$H NMR (400 MHz, CDCl$_3$) δ 3.93 (3H, s), 3.99 (3H, s), 7.69 (1H, d, J=8.4 Hz), 8.00 (1H, d, J=8.4 Hz).

C) methyl 3-chloro-2-hydroxy-4-(trifluoromethyl)benzoate

To a solution of methyl 3-chloro-2-[(methoxycarbonyl)oxy]-4-(trifluoromethyl)benzoate (6.00 g) in methanol (60.0 mL) was added potassium carbonate (8.00 g), and the mixture was stirred at 15° C. for 16 hr. The reaction mixture was filtered, the filtrate was neutralized with 1N hydrochloric acid, and the mixture was extracted with ethyl acetate. The organic layer was washed with saturated brine, and dried over anhydrous sodium sulfate, and the solvent was evaporated under reduced pressure to give the title compound (3.50 g).

$^1$H NMR (400 MHz, CDCl$_3$) δ 4.06 (3H, s), 7.29 (1H, d, J=5.2 Hz), 7.90 (1H, d, J=8.0 Hz), 11.55 (1H, brs).

D) methyl 5-bromo-3-chloro-2-hydroxy-4-(trifluoromethyl)benzoate

To a solution of methyl 3-chloro-2-hydroxy-4-(trifluoromethyl)benzoate (6.30 g) in DMF (65.0 mL) was added N-bromosuccinimide (4.41 g), and the mixture was stirred at 15° C. for 16 hr. The reaction mixture was poured into water, and the mixture was extracted with ethyl acetate. The organic layer was washed with saturated brine, and dried over anhydrous sodium sulfate, and the solvent was evaporated under reduced pressure to give the title compound (7.00 g).

$^1$H NMR (400 MHz, CDCl$_3$) δ 4.03 (3H, s), 8.13 (1H, s), 11.43 (1H, brs).

E) methyl 3-chloro-2-hydroxy-5-(4,4,5,5-tetramethyl-1,3,2-dioxaborolan-2-yl)-4-(trifluoromethyl)benzoate To a solution of methyl 5-bromo-3-chloro-2-hydroxy-4-(trifluoromethyl)benzoate (4.80 g) in toluene (70.0 mL) were added bis(pinacolato)diboron (5.48 g), potassium acetate (4.20 g) and trans-dichlorobis(triphenylphosphine)palladium(II) (0.51 g), and the mixture was stirred at 110° C. for 16 hr under argon atmosphere. The reaction mixture was allowed to be cooled to room temperature, and filtered, and the filtrate was extracted with ethyl acetate. The organic layer was dried over anhydrous sodium sulfate, and the solvent was evaporated under reduced pressure. The residue was purified by flash silica gel column chromatography (ethyl acetate/petroleum ether) to give the title compound (2.10 g).

$^1$H NMR (400 MHz, CDCl$_3$) δ 1.37 (12H, s), 4.02 (3H, s), 7.88 (1H, s), 11.57 (1H, brs).

F) ethyl 4-(1H-pyrazol-1-yl)benzoate

To a solution of ethyl 4-fluorobenzoate (105 g) in DMSO (250 mL) were added pyrazole (34.0 g) and potassium carbonate (138 g), and the mixture was heated with stirring at 130° C. for 16 hr. The reaction mixture was diluted with water, and the mixture was extracted with ethyl acetate. The organic layer was washed with saturated brine, and dried over anhydrous sodium sulfate, and the solvent was evaporated under reduced pressure to give the title compound (73.7 g).

$^1$H NMR (400 MHz, CDCl$_3$) δ 1.40 (3H, t, J=7.2 Hz), 4.38 (2H, q, J=7.2 Hz), 6.49 (1H, t, J=2.0 Hz), 7.75 (1H, d, J=1.6 Hz), 7.77 (2H, d, J=8.8 Hz), 7.99 (1H, d, J=2.4 Hz), 8.12 (2H, d, J=8.8 Hz).

G) [4-(1H-pyrazol-1-yl)phenyl]methanol

To a solution of ethyl 4-(1H-pyrazol-1-yl)benzoate (73.7 g) in THF (500 mL) were added sodium borohydride (19.5 g) and calcium chloride (56.8 g) under ice-cooling, and the mixture was stirred at room temperature for 16 hr, and then heated with reflux for 2 days. The reaction mixture was diluted with 1N hydrochloric acid, and the mixture was extracted with ethyl acetate (×4). The organic layer was washed with saturated brine, and dried over anhydrous sodium sulfate. The solvent was evaporated under reduced pressure, and the residue was washed with tert-butyl methyl ether to give the title compound (49.6 g).

$^1$HNMR (400 MHz, CDCl$_3$) δ 2.79 (1H, brs), 4.68 (2H, s), 6.45 (1H, t, J=2.0 Hz), 7.38 (2H, d, J=7.6 Hz), 7.61 (2H, d, J=8.4 Hz), 7.70 (1H, s), 7.89 (1H, d, J=1.6 Hz).

H) 1-[4-(chloromethyl)phenyl]-1H-pyrazole

To a solution of [4-(1H-pyrazol-1-yl)phenyl]methanol (24.0 g) in 1,2-dichloroethane (200 mL) was added dropwise thionyl chloride (26.3 g) under ice-cooling, and the mixture was stirred at room temperature for 16 hr. The reaction mixture was concentrated under reduced pressure, and the residue was washed with tert-butyl methyl ether to give the title compound (23.5 g).

$^1$HNMR (400 MHz, CDCl$_3$) δ 4.62 (2H, s), 6.48 (1H, t, J=2.0 Hz), 7.47 (2H, d, J=8.8 Hz), 7.69 (2H, d, J=8.8 Hz), 7.73 (1H, d, J=2.0 Hz), 7.93 (1H, d, J=2.4 Hz).

I) methyl 3-chloro-2-hydroxy-5-[4-(1H-pyrazol-1-yl)benzyl]-4-(trifluoromethyl)benzoate and 3-chloro-2-hydroxy-5-[4-(1H-pyrazol-1-yl)benzyl]-4-(trifluoromethyl)benzoic acid To a solution of methyl 3-chloro-2-hydroxy-5-(4,4,5,5-tetramethyl-1,3,2-dioxaborolan-2-yl)-4-(trifluoromethyl)benzoate (1.50 g) in 1,4-dioxane (30.0 mL) were added 1-(4-(chloromethyl)phenyl)-1H-pyrazole (0.76 g), tetrakis(triphenylphosphine)palladium(0) (0.23 g) and tripotassium phosphate trihydrate (2.10 g), and the mixture was stirred at 90° C. for 16 hr under nitrogen atmosphere. The reaction mixture was allowed to be cooled to room temperature, water and ethyl acetate were added thereto, and the mixture was partitioned. The organic layer was dried over anhydrous sodium sulfate, and the solvent was evaporated under reduced pressure. The residue was purified by flash silica gel column chromatography (ethyl acetate/petroleum ether) to give methyl 3-chloro-2-hydroxy-5-[4-(1H-pyrazol-1-yl)benzyl]-4-(trifluoromethyl)benzoate (0.12 g) and 3-chloro-2-hydroxy-5-[4-(1H-pyrazol-1-yl)benzyl]-4-(trifluoromethyl)benzoic acid (0.70 g).

$^1$H NMR (400 MHz, CDCl$_3$) δ 3.98 (3H, s), 4.21 (2H, d, J=2.0 Hz), 6.40 (1H, t, J=2.0 Hz), 7.12 (2H, d, J=8.4 Hz), 7.62 (2H, d, J=8.4 Hz), 7.68 (1H, s), 7.72 (1H, d, J=1.6 Hz), 7.90 (1H, d, J=2.4 Hz), 11.40 (1H, brs).

$^1$H NMR (400 MHz, CDCl$_3$) δ 3.49 (2H, s), 4.18 (1H, s), 6.40-6.52 (1H, m), 7.05-7.24 (2H, m), 7.44-7.58 (2H, m), 7.78-7.95 (3H, m). An active proton was not observed.

J) methyl 3-chloro-5-[4-(1H-pyrazol-1-yl)benzyl]-4-(trifluoromethyl)-2-{[(trifluoromethyl)sulfonyl]oxy}benzoate To a solution of methyl 3-chloro-2-hydroxy-5-[4-(1H-pyrazol-1-yl)benzyl]-4-(trifluoromethyl)benzoate (0.15 g) in dichloromethane (5.00 mL) were added triethylamine (0.05 g) and trifluoromethanesulfonic anhydride (0.14 g) under ice-cooling, and the mixture was stirred at room temperature for 16 hr. To the reaction mixture was added water, and the mixture was extracted with ethyl acetate. The organic layer was dried over anhydrous sodium sulfate, and the solvent was evaporated under reduced pressure to give the title compound (0.24 g) as a crude product. This compound was used in the next step without an additional purification.

MS: [M+H]+ 542.9.

K) methyl 3-chloro-2-ethenyl-5-[4-(1H-pyrazol-1-yl)benzyl]-4-(trifluoromethyl)benzoate To a solution of methyl 3-chloro-5-[4-(1H-pyrazol-1-yl)benzyl]-4-(trifluoromethyl)-2-{[(trifluoromethyl)sulfonyl]oxy}benzoate (0.24 g) in THF (5.00 mL)-water (5.00 mL) were added potassium vinyltrifluoroborate (0.07 g), cesium carbonate (0.24 g) and tetrakis(triphenylphosphine)palladium(0) (0.01 g), and the mixture was stirred at 90° C. for 16 hr under nitrogen atmosphere. To the reaction mixture was added water, and the mixture was extracted with ethyl acetate. The organic layer was dried over anhydrous sodium sulfate, and the solvent was evaporated under reduced pressure. The residue was purified by prep-thin layer chromatography (ethyl acetate/petroleum ether) to give the title compound (0.08 g).

$^1$H NMR (400 MHz, CDCl$_3$) δ 3.83 (3H, s), 4.28 (2H, d, J=2.0 Hz), 5.32 (1H, d, J=18.0 Hz), 5.54 (1H, d, J=12.4 Hz), 6.43-6.48 (1H, t, J=2.4 Hz), 6.94 (1H, dd, J=17.6, 11.2 Hz), 7.15 (2H, d, J=8.4 Hz), 7.37 (1H, s), 7.63 (2H, d, J=8.8 Hz), 7.71 (1H, d, J=1.2 Hz), 7.90 (1H, d, J=2.4 Hz).

L) ethyl 3-chloro-2-hydroxy-5-[4-(1H-pyrazol-1-yl)benzyl]-4-(trifluoromethyl)benzoate To a solution of 3-chloro-2-hydroxy-5-[4-(1H-pyrazol-1-yl)benzyl]-4-(trifluoromethyl)benzoic acid (0.60 g) in dichloromethane (20.0 mL) was added oxalyl chloride (0.29 g) under ice-cooling, and the mixture was stirred at 15° C. for 16 hr. The reaction mixture was added to a solution of triethylamine (2.00 mL) in ethanol (40.0 mL), and the mixture was stirred for 1 hr. The mixture was concentrated under reduced pressure, and the residue was diluted with ethyl acetate. The mixture was washed with 1N hydrochloric acid and saturated aqueous sodium bicarbonate solution, and the organic layer was concentrated under reduced pressure. The residue was purified by flash silica gel column chromatography (ethyl acetate/petroleum ether) to give the title compound (0.20 g).

$^1$H NMR (400 MHz, CDCl$_3$) δ 1.41 (3H, t, J=7.2 Hz), 4.22 (2H, d, J=2.0 Hz), 4.45 (2H, q, J=7.2 Hz), 6.42-6.49 (1H, m), 7.11 (2H, d, J=8.8 Hz), 7.59-7.64 (2H, m), 7.66-7.73 (2H, m), 7.89 (1H, d, J=2.4 Hz), 11.49 (1H, brs).

M) ethyl 3-chloro-5-[4-(1H-pyrazol-1-yl)benzyl]-4-(trifluoromethyl)-2-{[(trifluoromethyl)sulfonyl]oxy}benzoate To a solution of ethyl 3-chloro-2-hydroxy-5-[4-(1H-pyrazol-1-yl)benzyl]-4-(trifluoromethyl)benzoate (0.20 g) in dichloromethane (15.0 mL) were added triethylamine (0.10 g) and trifluoromethanesulfonic anhydride (0.27 g) under ice-cooling, and the mixture was stirred at room temperature for 16 hr. To the reaction mixture was added water, and the mixture was extracted with ethyl acetate. The organic layer was dried over anhydrous sodium sulfate, and the solvent was evaporated under reduced pressure to give the title compound (0.25 g) as a crude product. This compound was used in the next step without an additional purification.

MS: [M+H]+ 557.0.

N) ethyl 3-chloro-2-ethenyl-5-[4-(1H-pyrazol-1-yl)benzyl]-4-(trifluoromethyl)benzoate To a solution of ethyl 3-chloro-5-[4-(1H-pyrazol-1-yl)benzyl]-4-(trifluoromethyl)-2-{[(trifluoromethyl)sulfonyl]oxy}benzoate (0.25 g) in THF (8.00 mL)-water (5.00 mL) were added potassium vinyltrifluoroborate (0.13 g), cesium carbonate (0.46 g) and tetrakis(triphenylphosphine)palladium(0) (0.03 g), and the mixture was stirred at 80° C. for 16 hr under nitrogen atmosphere. To the reaction mixture was added water, and the mixture was extracted with ethyl acetate. The organic layer was dried over anhydrous sodium sulfate, and the solvent was evaporated under reduced pressure. The residue was purified by thin layer chromatography (ethyl acetate/petroleum ether) to give the title compound (0.08 g).

$^1$H NMR (400 MHz, CDCl$_3$) δ 1.32 (3H, t, J=7.2 Hz), 4.25-4.34 (4H, m), 5.34 (1H, d, J=17.6 Hz), 5.54 (1H, d, J=12.4 Hz), 6.46 (1H, t, J=2.0 Hz), 6.94 (1H, dd, J=17.2, 11.2 Hz), 7.15 (2H, d, J=8.0 Hz), 7.36 (1H, s), 7.63 (2H, d, J=8.8 Hz), 7.71 (1H, d, J=1.6 Hz), 7.90 (1H, d, J=2.4 Hz).

O) 3-chloro-2-ethenyl-5-[4-(1H-pyrazol-1-yl)benzyl]-4-(trifluoromethyl)benzoic acid To a solution of methyl 3-chloro-2-ethenyl-5-[4-(1H-pyrazol-1-yl)benzyl]-4-(trifluoromethyl)benzoate (0.80 g) and ethyl 3-chloro-2-ethenyl-5-[4-(1H-pyrazol-1-yl)benzyl]-4-(trifluoromethyl)benzoate (0.80 g) in THF (5.08 mL)-water (5.08 mL) were added lithium hydroxide monohydrate (0.20 g) and methanol (0.50 mL), and the mixture was stirred at 15° C. for 16 hr. The reaction mixture was poured into 1N hydrochloric acid, and the mixture was extracted with ethyl acetate. The organic layer was dried over anhydrous sodium sulfate, and the solvent was evaporated under reduced pressure to give the title compound (0.15 g).

$^1$H NMR (400 MHz, CDCl$_3$) δ 4.28 (2H, s), 5.44 (1H, d, J=17.2 Hz), 5.59 (1H, d, J=12.0 Hz), 6.49 (1H, t, J=2.0 Hz), 6.96 (1H, dd, J=18.0, 11.6 Hz), 7.16 (2H, d, J=8.4 Hz), 7.51 (1H, s), 7.59 (2H, d, J=8.4 Hz), 7.80 (1H, d, J=1.6 Hz), 7.90 (1H, d, J=2.4 Hz).

P) rac-3-chloro-2-ethenyl-N-(trans-2-hydroxycyclohexyl)-5-[4-(1H-pyrazol-1-yl)benzyl]-4-(trifluoromethyl)benzamide To a solution of 3-chloro-2-ethenyl-5-[4-(1H-pyrazol-1-yl)benzyl]-4-(trifluoromethyl)benzoic acid (0.05 g), trans-2-aminocyclohexanol hydrochloride (0.03 g), 1-hydroxybenzotriazole (0.03 g) and 1-(3-dimethylaminopropyl)-3-ethylcarbodiimide hydrochloride (0.04 g) in dichloromethane (5.00 mL) was added triethylamine (0.04 g), and the mixture was stirred for 16 hr. The reaction mixture was poured into water, and the mixture was extracted with ethyl acetate. The organic layer was washed with 1N hydrochloric acid and saturated aqueous sodium bicarbonate solution, and dried over anhydrous sodium sulfate, and the solvent was evaporated under reduced pressure to give the title compound (0.07 g).

$^1$H NMR (400 MHz, CDCl$_3$) δ 1.25-1.40 (4H, m), 1.70-1.77 (2H, m), 1.90-2.00 (1H, m), 2.05-2.10 (1H, m), 3.32-3.40 (1H, m), 3.60-3.80 (1H, m), 4.26 (2H, s), 5.50-5.75 (3H, m), 6.45 (1H, t, J=2.0 Hz), 6.85-6.98 (1H, m), 7.14 (2H, d, J=8.4 Hz), 7.30 (1H, s), 7.61 (2H, d, J=8.4 Hz), 7.71 (1H, d, J=1.2 Hz), 7.89 (1H, d, J=2.4 Hz).

Q) rac-4-chloro-2-(trans-2-hydroxycyclohexyl)-6-(4-(H-pyrazol-1-yl)benzyl)-5-(trifluoromethyl)isoindolin-1-one To a solution of rac-3-chloro-2-ethenyl-N-(trans-2-hydroxycyclohexyl)-5-[4-(1H-pyrazol-1-yl)benzyl]-4-(trifluoromethyl)benzamide (0.07 g) in a mixed solvent of acetone (2.00 mL)-acetonitrile (2.00 mL)-water (2.00 mL) were added potassium osmate(VI) dihydrate (4.00 mg) and sodium periodate (0.08 g), and the mixture was stirred for 16 hr. The reaction mixture was diluted with aqueous sodium thiosulfate solution, and the mixture was extracted with ethyl acetate. The organic layer was dried over anhydrous sodium sulfate, and the solvent was evaporated under reduced pressure to give rac-4-chloro-3-hydroxy-2-[trans-2-hydroxycyclohexyl]-6-[4-(1H-pyrazol-1-yl)benzyl]-5-(trifluoromethyl)-2,3-dihydro-1H-isoindol-1-one (0.05 g) as a crude product. This compound was used in the next step without an additional purification.

MS: [M+H]$^+$ 505.9.

To a solution of the above-mentioned compound (0.05 g) in dichloromethane (2.00 mL) was added trifluoroacetic acid (0.30 mL) under ice-cooling. After 15 min, triethylsilane (0.40 mL) was added thereto, and the mixture was stirred at 15° C. for 16 hr. The reaction mixture was poured into saturated aqueous sodium bicarbonate solution, and the mixture was extracted with ethyl acetate (×2). The organic layer was dried over anhydrous sodium sulfate, and the solvent was evaporated under reduced pressure. The residue was purified by prep-HPLC, then lyophilized to give the title compound (0.01 g).

$^1$H NMR (400 MHz, CDCl$_3$) δ 1.36-1.45 (2H, m), 1.54-1.62 (1H, m, overlapped with water signal), 1.83 (2H, d, J=12.0 Hz), 1.92 (1H, d, J=12.0 Hz), 2.13-2.26 (2H, m), 3.64-3.77 (1H, m), 4.03-4.13 (1H, m), 4.33 (2H, s), 4.37-4.55 (2H, m), 6.45 (1H, t, J=2.0 Hz), 7.14 (2H, d, J=8.4 Hz), 7.60 (2H, d, J=8.4 Hz), 7.64 (1H, s), 7.70 (1H, d, J=1.6 Hz), 7.89 (1H, d, J=2.4 Hz).

Example 11 rac-2-(trans-2-hydroxycyclohexyl)-4-methyl-1-oxo-6-(4-(1H-pyrazol-1-yl)benzyl)isoindoline-5-carbonitrile A) 3-hydroxy-2-methylbenzonitrile To a solution of 3-bromo-2-methylphenol (20.0 g) in DMF (250 mL) were added copper(I) cyanide (19.0 g) and tetrakis(triphenylphosphine)palladium(0) (3.70 g), and the mixture was heated with stirring at 120° C. for 16 hr under nitrogen atmosphere. The reaction mixture was poured into water, and the mixture was filtered. The filtrate was extracted with ethyl acetate, and the organic layer was dried over anhydrous sodium sulfate. The solvent was evaporated under reduced pressure, and the residue was washed with tert-butyl methyl ether to give the title compound (7.00 g).

$^1$H NMR (400 MHz, CDCl$_3$) δ 2.28 (3H, s), 7.00-7.15 (1H, m), 7.14-7.24 (2H, m), 10.11 (1H, brs).

B) 4-formyl-3-hydroxy-2-methylbenzonitrile

To a solution of 3-hydroxy-2-methylbenzonitrile (7.00 g) in THF (100 mL) were added triethylamine (13.1 g), magnesium chloride (12.4 g) and paraformaldehyde (6.60 g), and the mixture was heated with reflux for 16 hr under nitrogen atmosphere. The reaction mixture was poured into 1N hydrochloric acid, and the mixture was extracted with ethyl acetate. The organic layer was dried over anhydrous sodium sulfate, and the solvent was evaporated under reduced pressure. The residue was purified by flash silica gel column chromatography (ethyl acetate/petroleum ether) to give the title compound (1.30 g).

$^1$H NMR (400 MHz, CDCl$_3$) δ 2.50 (3H, s), 7.24-7.28 (2H, m, overlapped with CDCl$_3$ signal), 7.53 (1H, d, J=8.0 Hz), 9.98 (1H, s), 11.42 (1H, brs).

C) 4-cyano-2-hydroxy-3-methylbenzoic acid

To a solution of 4-formyl-3-hydroxy-2-methylbenzonitrile (3.90 g) in DMSO (21.0 mL) were added sodium dihydrogenphosphate (7.26 g) and an aqueous solution (16.0 mL) of sodium chlorite (5.46 g) under ice-cooling, and the mixture was stirred at 17° C. for 16 hr. The reaction mixture was poured into saturated aqueous sodium carbonate solution, and the mixture was extracted with tert-butyl methyl ether. The aqueous layer was acidified with 1N hydrochloric acid, and the mixture was extracted with ethyl acetate. The combined organic layers were dried over anhydrous sodium sulfate, and the solvent was evaporated under reduced pressure to give the title compound (4.00 g: containing DMSO).

$^1$H NMR (400 MHz, DMSO-d$_6$) δ 2.36 (3H, s), 7.29 (1H, d, J=8.0 Hz), 7.77 (1H, d, J=8.0 Hz). An active proton was not observed.

D) 5-bromo-4-cyano-2-hydroxy-3-methylbenzoic acid

To a solution of 4-cyano-2-hydroxy-3-methylbenzoic acid (5.50 g) in DMF (50.0 mL) was added N-bromosuccinimide (5.50 g) under ice-cooling, and the mixture was stirred at 15° C. for 16 hr. The reaction mixture was poured into water, and the mixture was extracted with ethyl acetate. The organic layer was dried over anhydrous sodium sulfate, and the solvent was evaporated under reduced pressure to give the title compound (7.40 g: containing DMF).

$^1$H NMR (400 MHz, CDCl$_3$) δ 2.51 (3H, s), 8.10 (1H, s), 11.48 (1H, brs).

E) methyl 5-bromo-4-cyano-2-hydroxy-3-methylbenzoate

To a solution of 5-bromo-4-cyano-2-hydroxy-3-methylbenzoic acid (7.40 g) in dichloromethane (70.0 mL) were added oxalyl chloride (3.91 g) and DMF (0.20 mL) under ice-cooling, and the mixture was stirred for 3 hr. The reaction mixture was concentrated under reduced pressure, and the residue was diluted with THF. To this mixture was added dropwise a solution of triethylamine (5.66 g) in methanol (50.0 mL) under ice-cooling, and the mixture was stirred for 20 min. The reaction mixture was poured into 1N hydrochloric acid, and the mixture was extracted with ethyl acetate. The organic layer was dried over anhydrous sodium sulfate, and the solvent was evaporated under reduced pressure. The residue was purified by silica gel column chromatography (ethyl acetate/petroleum ether) to give the title compound (4.20 g).

$^1$H NMR (400 MHz, CDCl$_3$) δ 2.51 (3H, s), 4.00 (3H, s), 7.97 (1H, s), 10.14 (1H, brs).

F) methyl 4-cyano-2-hydroxy-3-methyl-5-(4,4,5,5-tetramethyl-1,3,2-dioxaborolan-2-yl)benzoate To a solution of methyl 5-bromo-4-cyano-2-hydroxy-3-methylbenzoate (2.00 g) in toluene (30.0 mL) were added bis(pinacolato)diboron (2.82 g), potassium acetate (2.18 g) and trans-dichlorobis(triphenylphosphine)palladium(II) (0.26 g), and the mixture was stirred at 110° C. for 16 hr under argon atmosphere. The reaction mixture was poured into water, and the mixture was extracted with ethyl acetate. The organic layer was washed with saturated brine, and dried over anhydrous sodium sulfate, and the solvent was evaporated under reduced pressure. The residue was purified by flash silica gel column chromatography (ethyl acetate/petroleum ether) to give the title compound (2.50 g: containing bis(pinacolato)diboron).

$^1$H NMR (400 MHz, CDCl$_3$) δ 1.38 (12H, s), 2.49 (3H, s), 3.99 (3H, s), 8.20 (1H, s), 11.43 (1H, brs).

G) methyl 4-cyano-2-hydroxy-3-methyl-5-[4-(1H-pyrazol-1-yl)benzyl]benzoate

To a solution of methyl 4-cyano-2-hydroxy-3-methyl-5-(4,4,5,5-tetramethyl-1,3,2-dioxaborolan-2-yl)benzoate (3.50 g) in 1,4-dioxane (30.0 mL) were added 1-(4-(chloromethyl)phenyl)-1H-pyrazole (2.12 g), tripotassium phosphate trihydrate (5.90 g) and [1,1'-bis(diphenylphosphino)ferrocene]dichloropalladium(II)dichloromethane adduct (0.34 g), and the mixture was stirred at 90° C. for 16 hr under nitrogen atmosphere. The reaction mixture was poured into water, and the mixture was extracted with ethyl acetate. The organic layer was dried over anhydrous sodium sulfate, and the solvent was evaporated under reduced pressure. The residue was purified by flash silica gel column chromatography (ethyl acetate/petroleum ether) to give the title compound (0.86 g).

$^1$H NMR (400 MHz, CDCl$_3$) δ 2.49 (3H, s), 3.95 (3H, s), 4.15 (2H, s), 6.46 (1H, s), 7.30 (2H, d, J=8.4 Hz), 7.59-7.60 (1H, m), 7.64 (2H, d, J=8.4 Hz), 7.71 (1H, s), 7.90 (1H, d, J=2.4 Hz), 11.07 (1H, brs).

H) methyl 4-cyano-3-methyl-5-[4-(1H-pyrazol-1-yl)benzyl]-2-{[(trifluoromethyl)sulfonyl]oxy}benzoate To a solution of methyl 4-cyano-2-hydroxy-3-methyl-5-[4-(1H-pyrazol-1-yl)benzyl]benzoate (0.86 g) in THF (20.0 mL) was added sodium hydride (0.12 g) under ice-cooling, and the mixture was stirred for 20 min. To this reaction mixture was added N-phenylbis(trifluoromethanesulfonimide)(1.77 g), and the mixture was stirred at 15° C. for 16 hr. The reaction mixture was poured into saturated aqueous ammonium chloride solution, and the mixture was extracted with ethyl acetate. The organic layer was dried over anhydrous sodium sulfate, and the solvent was evaporated under reduced pressure to give the title compound (3.00 g) as a crude product. This compound was used in the next step without an additional purification.

MS: [M+H]$^+$ 479.8.

I) methyl 4-cyano-2-ethenyl-3-methyl-5-[4-(1H-pyrazol-1-yl)benzyl]benzoate

To a solution of methyl 4-cyano-3-methyl-5-[4-(1H-pyrazol-1-yl)benzyl]-2-{[(trifluoromethyl)sulfonyl]oxy}benzoate (2.80 g) in THF (25.0 mL)-water (5.00 mL) were added potassium vinyltrifluoroborate (0.85 g), cesium carbonate (6.23 g) and tetrakis(triphenylphosphine)palladium(0) (0.38 g), and the mixture was stirred at 80° C. for 16 hr under nitrogen atmosphere. To the reaction mixture was added water, and the mixture was extracted with ethyl acetate. The organic layer was dried over anhydrous sodium sulfate, and the solvent was evaporated under reduced pressure. The residue was purified by flash silica gel column chromatography (ethyl acetate/petroleum ether) to give the title compound (0.80 g).

$^1$H NMR (400 MHz, CDCl$_3$) δ 2.56 (3H, s), 3.83 (3H, s), 4.23 (2H, s), 5.21 (1H, d, J=17.6 Hz), 5.46-5.60 (1H, m), 6.46 (1H, s), 6.88 (1H, dd, J=17.6, 11.4 Hz), 7.32 (2H, d, J=8.4 Hz), 7.41 (1H, s), 7.64 (2H, d, J=8.4 Hz), 7.71 (1H, s), 7.90 (1H, d, J=2.4 Hz).

J) 4-cyano-2-ethenyl-3-methyl-5-[4-(H-pyrazol-1-yl)benzyl]benzoic acid

To a solution of methyl 4-cyano-2-ethenyl-3-methyl-5-[4-(1H-pyrazol-1-yl)benzyl]benzoate (0.70 g) in THF (5.00 mL)-water (5.00 mL) were added lithium hydroxide monohydrate (0.25 g) and methanol (1.00 mL), and the mixture was stirred at 10° C. for 16 hr. The reaction mixture was diluted with water, and the mixture was extracted with tert-butyl methyl ether. The aqueous layer was acidified with 2N hydrochloric acid, and the mixture was extracted with ethyl acetate. The organic layer was dried over anhydrous sodium sulfate, and the solvent was evaporated under reduced pressure to give the title compound (0.60 g).

$^1$H NMR (400 MHz, CDCl$_3$) δ 2.55 (3H, s), 4.22 (2H, s), 5.25 (1H, dd, J=17.8, 1.4 Hz), 5.55 (1H, dd, J=11.6, 1.2 Hz), 6.47 (1H, t, J=2.0 Hz), 6.93 (1H, dd, J=17.8, 11.4 Hz), 7.34 (2H, d, J=8.4 Hz), 7.58 (1H, s), 7.62 (2H, d, J=8.8 Hz), 7.79 (1H, d, J=1.6 Hz), 7.90 (1H, d, J=2.4 Hz). One active proton was not observed.

K) rac-4-cyano-2-ethenyl-N-(trans-2-hydroxycyclohexyl)-3-methyl-5-[4-(1H-pyrazol-1-yl)benzyl]benzamide To a solution of 4-cyano-2-ethenyl-3-methyl-5-[4-(1H-pyrazol-1-yl)benzyl]benzoic acid (0.10 g), trans-2-aminocyclohexanol hydrochloride (0.06 g), 1-hydroxybenzotriazole (0.06 g) and 1-(3-dimethylaminopropyl)-3-ethylcarbodiimide hydrochloride (0.08 g) in dichloromethane (5.00 mL) was added triethylamine (0.11 g), and the mixture was stirred for 16 hr. The reaction mixture was poured into 1N hydrochloric acid, and the mixture was extracted with ethyl acetate. The organic layer was washed with 1N hydrochloric acid and saturated aqueous sodium bicarbonate solution, and dried over anhydrous sodium sulfate, and the solvent was evaporated under reduced pressure to give the title compound (0.10 g).

$^1$H NMR (400 MHz, CDCl$_3$) δ 1.11-1.41 (6H, m), 1.95-2.10 (2H, m), 2.55 (3H, s), 3.21-3.30 (1H, m), 3.36 (1H, td, J=10.0, 4.4 Hz), 3.68-3.80 (1H, m), 4.20 (2H, s), 5.47 (1H, dd, J=17.8, 1.2 Hz), 5.61 (1H, dd, J=11.6, 1.2 Hz), 5.70 (1H, d, J=7.2 Hz), 6.45 (1H, t, J=2.0 Hz), 6.78 (1H, dd, J=17.8, 11.6 Hz), 7.25-7.26 (1H, m, overlapped with CDCl$_3$ signal), 7.32 (2H, d, J=8.4 Hz), 7.62 (2H, d, J=8.4 Hz), 7.70 (1H, d, J=2.0 Hz), 7.89 (1H, d, J=2.4 Hz).

L) rac-3-hydroxy-2-(trans-2-hydroxycyclohexyl)-4-methyl-1-oxo-6-[4-(1H-pyrazol-1-yl)benzyl]-2,3-dihydro-1H-isoindole-5-carbonitrile To a solution of rac-4-cyano-2-ethenyl-N-(trans-2-hydroxycyclohexyl)-3-methyl-5-[4-(1H-pyrazol-1-yl)benzyl]

benzamide (0.09 g) in a mixed solvent of acetone (2.00 mL)-acetonitrile (2.00 mL)-water (2.00 mL) were added potassium osmate(VI) dihydrate (7.00 mg) and sodium periodate (0.18 g), and the mixture was stirred for 16 hr. The reaction mixture was diluted with saturated aqueous sodium thiosulfate solution, and the mixture was extracted with ethyl acetate. The organic layer was dried over anhydrous sodium sulfate, and the solvent was evaporated under reduced pressure to give the title compound (0.10 g) as a crude product. This compound was used in the next step without an additional purification.

MS: $[M+H]^+$ 443.0.

M) rac-2-(trans-2-hydroxycyclohexyl)-4-methyl-1-oxo-6-(4-(1H-pyrazol-1-yl)benzyl)isoindoline-5-carbonitrile To a solution of rac-3-hydroxy-2-(trans-2-hydroxycyclohexyl)-4-methyl-1-oxo-6-[4-(1H-pyrazol-1-yl)benzyl]-2,3-dihydro-1H-isoindole-5-carbonitrile (0.10 g) in dichloromethane (2.00 mL) was added trifluoroacetic acid (0.31 mL) under ice-cooling. After 15 min, triethylsilane (0.50 mL) was added thereto, and the mixture was stirred at 15° C. for 16 hr. The reaction mixture was poured into saturated aqueous sodium bicarbonate solution, and the mixture was extracted with ethyl acetate (×2). The organic layer was dried over anhydrous sodium sulfate, and the solvent was evaporated under reduced pressure. The residue was purified by prep-HPLC, then lyophilized to give the title compound (0.02 g).

$^1$H NMR (400 MHz, CDCl$_3$) δ 1.35-1.52 (3H, m), 1.85 (2H, d, J=12.4 Hz), 1.94 (1H, d, J=13.6 Hz), 2.10 (1H, d, J=6.8 Hz), 2.20 (1H, d, J=12.0 Hz), 2.57 (3H, s), 3.55-3.65 (1H, m), 4.07-4.16 (1H, m), 4.30-4.48 (4H, m), 6.41-6.51 (1H, m), 7.35 (2H, d, J=8.4 Hz), 7.61-7.69 (3H, m), 7.72 (1H, d, J=1.6 Hz), 7.91 (1H, d, J=2.4 Hz). One active proton was observed.

Example 12 rac-4-chloro-2-(trans-2-hydroxycyclohexyl)-5-methoxy-6-(4-(1H-pyrazol-1-yl)benzyl)isoindolin-1-one A) 2-chloro-3-methoxyphenol To an aqueous solution (100 mL) of potassium hydroxide (11.0 g) was added 2-chlorobenzene-1,3-diol (22.8 g). Then, dimethyl sulfate (19.9 g) was slowly added to the reaction mixture while keeping the reaction mixture at 10° C. to 20° C., and the mixture was stirred at 100° C. for 2 days. The reaction mixture was acidified with 2N hydrochloric acid, and the mixture was extracted with dichloromethane. The organic layer was dried over anhydrous sodium sulfate, and the solvent was evaporated under reduced pressure. The residue was purified by silica gel column chromatography (ethyl acetate/petroleum ether) to give the title compound (18.0 g).

$^1$H NMR (400 MHz, DMSO-d$_6$) δ 3.78 (3H, s), 6.54-6.58 (2H, m), 7.05 (1H, t, J=8.4 Hz), 10.04 (1H, brs).

B) 3-chloro-2-hydroxy-4-methoxybenzaldehyde

To a solution of 2-chloro-3-methoxyphenol (19.3 g) in 1,2-dichloroethane (150 mL) were added triethylamine (73.7 g), magnesium chloride (57.8 g) and paraformaldehyde (36.5 g), and the mixture was stirred at 70° C. for 4 hr under nitrogen atmosphere. The reaction mixture was poured into 1N hydrochloric acid, and the precipitate was removed by filtration, and washed with dichloromethane. The organic layer was washed with 1N hydrochloric acid and saturated brine, and dried over anhydrous sodium sulfate, and the solvent was evaporated under reduced pressure to give the title compound (21.5 g).

$^1$H NMR (400 MHz, DMSO-d$_6$) δ 3.97 (3H, s), 6.92 (1H, d, J=8.8 Hz), 7.76 (1H, d, J=9.2 Hz), 9.95 (1H, s), 11.47 (1H, brs).

C) 3-chloro-2-hydroxy-4-methoxybenzoic acid

To a solution of 3-chloro-2-hydroxy-4-methoxybenzaldehyde (16.6 g) and sodium dihydrogenphosphate (34.7 g) in a mixed solvent of DMSO (180 mL)-water (45.0 mL) was added an aqueous solution (35.0 mL) of sodium chlorite (27.2 g) under ice-cooling, and the mixture was stirred at 15° C. for 16 hr. The reaction mixture was poured into saturated aqueous sodium carbonate solution, the mixture was diluted with water, and filtered, and the filtrate was extracted with petroleum ether/ethyl acetate=5:1. The aqueous layer was acidified with conc. hydrochloric acid to adjusted pH=1, and the mixture was extracted with ethyl acetate. The organic layer was washed with 1N hydrochloric acid, and dried over anhydrous sodium sulfate, and the solvent was evaporated under reduced pressure to give the title compound (11.1 g).

$^1$H NMR (400 MHz, DMSO-d$_6$) δ3.93 (3H, s), 6.77 (1H, d, J=9.2 Hz), 7.78 (1H, d, J=9.2 Hz), 12.11 (1H, brs). One active proton was not observed.

D) 5-bromo-3-chloro-2-hydroxy-4-methoxybenzoic acid

To a solution of 3-chloro-2-hydroxy-4-methoxybenzoic acid (11.1 g) in acetic acid (275 mL) was added bromine (8.79 g) at room temperature, and the mixture was stirred for 16 hr. To the reaction mixture was added water, and the precipitate was collected by filtration. The precipitate was washed with water, and dissolved in ethyl acetate, and the solution was washed with water and saturated brine. The organic layer was dried over anhydrous sodium sulfate, and the solvent was evaporated under reduced pressure to give the title compound (10.4 g).

$^1$H NMR (400 MHz, DMSO-d$_6$) δ3.87 (3H, s), 7.94 (1H, s). Two active protons were not observed.

E) methyl 5-bromo-3-chloro-2-hydroxy-4-methoxybenzoate

To a solution of 5-bromo-3-chloro-2-hydroxy-4-methoxybenzoic acid (10.4 g) in dichloromethane (150 mL) were added a solution of oxalyl chloride (7.05 g) in dichloromethane (10 mL) and DMF (3 drops) under ice-cooling, and the mixture was stirred at 13° C. for 1 hr. The solvent was evaporated under reduced pressure, and the residue was dissolved in THF (50 mL). This solution was added dropwise to a solution of triethylamine (1.20 g) in methanol (150 mL) under ice-cooling, and the mixture was stirred at 13° C. for 16 hr. The solvent was evaporated under reduced pressure from the reaction mixture, and the residue was diluted with ethyl acetate and water. 1N Hydrochloric acid was added thereto, and the mixture was partitioned. The organic layer was washed with water and saturated brine, and dried over anhydrous sodium sulfate, and the solvent was evaporated under reduced pressure to give the title compound (10.9 g).

¹H NMR (400 MHz, DMSO-d₆) δ 3.86 (3H, s), 3.91 (3H, s), 7.94 (1H, s), 11.11 (1H, brs).

F) methyl 5-bromo-3-chloro-4-methoxy-2-(methoxymethoxy)benzoate

To a solution of methyl 5-bromo-3-chloro-2-hydroxy-4-methoxybenzoate (5.00 g) in THF (120 mL) was added sodium hydride (1.01 g) under ice-cooling, and the mixture was stirred for 1 hr under nitrogen atmosphere. To this reaction mixture was added dropwise chloromethyl methyl ether (1.63 g), and the mixture was stirred at 20° C. for 16 hr. To the reaction mixture was added water, and the mixture was extracted with ethyl acetate. The organic layer was washed with saturated brine, and dried over anhydrous sodium sulfate. The solvent was evaporated under reduced pressure, and the residue was purified by flash silica gel column chromatography (ethyl acetate/petroleum ether) to give the title compound (3.08 g).
¹H NMR (400 MHz, CDCl₃) δ 3.65 (3H, s), 3.93 (3H, s), 3.96 (3H, s), 5.15 (2H, s), 8.00 (1H, s).

G) 1-{4-[(4,4,5,5-tetramethyl-1,3,2-dioxaborolan-2-yl)methyl]phenyl}-1H-pyrazole To a solution of 1-[4-(chloromethyl)phenyl]-1H-pyrazole (2.20 g) in 1,4-dioxane (50.0 mL) were added bis(pinacolato)diboron (3.47 g), potassium acetate (3.35 g) and [1,1'-bis(diphenylphosphino)ferrocene]dichloropalladium(II)-dichloromethane adduct (0.47 g), and the mixture was stirred at 90° C. for 16 hr under argon atmosphere. The reaction mixture was allowed to be cooled to room temperature, and filtered, and the solvent was evaporated under reduced pressure from the filtrate. The residue was purified by silica gel column chromatography (ethyl acetate/petroleum ether) to give the title compound (3.10 g).
¹HNMR (400 MHz, CDCl₃) δ 1.22 (12H, s), 2.32 (2H, s), 6.43 (1H, t, J=2.0 Hz), 7.23-7.29 (2H, m, overlap with CDCl₃ signal), 7.54 (2H, d, J=8.4 Hz), 7.69 (1H, d, J=1.2 Hz), 7.87 (1H, d, J=2.8 Hz).

H) methyl 3-chloro-2-hydroxy-4-methoxy-5-[4-(1H-pyrazol-1-yl)benzyl]benzoate

To a solution of methyl 5-bromo-3-chloro-4-methoxy-2-(methoxymethoxy)benzoate (3.00 g) in 1,4-dioxane (50.0 mL)-water (5.00 mL) were added 1-{4-[(4,4,5,5-tetramethyl-1,3,2-dioxaborolan-2-yl)methyl]phenyl}-1H-pyrazole (7.50 g), potassium carbonate (2.44 g) and tetrakis(triphenylphosphine)palladium(0) (1.02 g), and the mixture was stirred at 90° C. for 16 hr under nitrogen atmosphere. The reaction mixture was poured into water, and the mixture was extracted with ethyl acetate. The organic layer was dried over anhydrous sodium sulfate, and the solvent was evaporated under reduced pressure. The residue was purified by flash silica gel column chromatography (ethyl acetate/petroleum ether) to give methyl 3-chloro-4-methoxy-2-(methoxymethoxy)-5-[4-(1H-pyrazol-1-yl)benzyl]benzoate (0.40 g).
To a solution of the above-mentioned compound (0.40 g) in ethyl acetate (5.00 mL) was added 4N hydrogen chloride/ethyl acetate (25.0 mL), and the mixture was stirred at room temperature for 16 hr. The reaction mixture was poured into saturated aqueous sodium bicarbonate solution, and the mixture was extracted with ethyl acetate. The organic layer was dried over anhydrous sodium sulfate, and the solvent was evaporated under reduced pressure. The residue was purified by flash silica gel column chromatography (ethyl acetate/petroleum ether) to give the title compound (0.23 g).
¹H NMR (400 MHz, CDCl₃) δ 3.78 (3H, s), 3.93 (3H, s), 3.97 (2H, s), 6.45 (1H, t, J=2.0 Hz), 7.24 (1H, s), 7.27 (1H, s, overlapped with CDCl₃ signal), 7.58-7.63 (3H, m), 7.71 (1H, d, J=1.6 Hz), 7.89 (1H, d, J=2.4 Hz), 11.36 (1H, brs).

I) methyl 3-chloro-4-methoxy-5-[4-(1H-pyrazol-1-yl)benzyl]-2-{[(trifluoromethyl)sulfonyl]oxy}benzoate To a solution of methyl 3-chloro-2-hydroxy-4-methoxy-5-[4-(1H-pyrazol-1-yl)benzyl]benzoate (0.23 g) in dichloromethane (10.0 mL) were added triethylamine (0.13 g) and trifluoromethanesulfonic anhydride (0.35 g) under ice-cooling, and the mixture was stirred at room temperature for 16 hr. To the reaction mixture was added water, and the mixture was extracted with ethyl acetate. The organic layer was dried over anhydrous sodium sulfate, and the solvent was evaporated under reduced pressure to give the title compound (0.36 g) as a crude product. This compound was used in the next step without an additional purification.
MS: [M+H]⁺ 505.0.

J) methyl 3-chloro-2-ethenyl-4-methoxy-5-[4-(1H-pyrazol-1-yl)benzyl]benzoate

To a solution of methyl 3-chloro-4-methoxy-5-[4-(1H-pyrazol-1-yl)benzyl]-2-{[(trifluoromethyl)sulfonyl]oxy}benzoate (0.36 g) in THF (8.00 mL)-water (3.00 mL) were added potassium vinyltrifluoroborate (0.17 g), cesium carbonate (0.60 g) and tetrakis(triphenylphosphine)palladium(0) (0.04 g), and the mixture was heated with reflux for 16 hr under nitrogen atmosphere. To the reaction mixture was added water, and the mixture was extracted with ethyl acetate. The organic layer was dried over anhydrous sodium sulfate, and the solvent was evaporated under reduced pressure. The residue was purified by thin layer chromatography (ethyl acetate/petroleum ether) to give the title compound (0.08 g).
¹H NMR (400 MHz, CDCl₃) δ 3.76 (3H, s), 3.81 (3H, s), 4.05 (2H, s), 5.33 (1H, d, J=17.6 Hz), 5.52 (1H, dd, J=11.2, 1.2 Hz), 6.45 (1H, t, J=2.0 Hz), 6.93 (1H, dd, J=17.8, 11.2 Hz), 7.28 (2H, d, J=8.4 Hz), 7.43 (1H, s), 7.62 (2H, d, J=8.4 Hz), 7.71 (1H, d, J=1.4 Hz), 7.89 (1H, d, J=2.4 Hz).

K) 3-chloro-2-ethenyl-4-methoxy-5-[4-(1H-pyrazol-1-yl)benzyl]benzoic acid

To a solution of methyl 3-chloro-2-ethenyl-4-methoxy-5-[4-(1H-pyrazol-1-yl)benzyl]benzoate (0.10 g) in THF (3.00 mL)-water (3.00 mL) and methanol (0.50 mL) was added lithium hydroxide monohydrate (0.10 g), and the mixture was stirred at 20° C. for 16 hr. The reaction mixture was poured into 1N hydrochloric acid, and the mixture was extracted with ethyl acetate. The organic layer was dried over anhydrous sodium sulfate, and the solvent was evaporated under reduced pressure to give the title compound (0.08 g).
¹H NMR (400 MHz, CDCl₃) δ 3.78 (3H, s), 4.22 (2H, s), 4.06 (2H, s), 5.42 (1H, d, J=17.6 Hz), 5.58 (1H, d, J=11.2 Hz), 6.46 (1H, t, J=2.0 Hz), 6.94 (1H, dd, J=18.0, 11.6 Hz), 7.25-7.40 (2H, m, overlap with CDCl₃ signal), 7.50-7.65 (3H, m), 7.72 (1H, s), 7.89 (1H, d, J=2.4 Hz). An active proton was not observed.

L) rac-3-chloro-2-ethenyl-N-(trans-2-hydroxycyclohexyl)-4-methoxy-5-[4-(1H-pyrazol-1-yl)benzyl]benzamide To a solution of 3-chloro-2-ethenyl-4-methoxy-5-[4-(1H-pyrazol-1-yl)benzyl]benzoic acid (0.06 g), trans-2-aminocyclohexanol hydrochloride (0.04 g), 1-hydroxybenzotriazole (0.03 g) and 1-(3-dimethylaminopropyl)-3-ethylcarbodiimide hydrochloride (0.05 g) in dichloromethane (10.0 mL) was added triethylamine (0.03 g), and the mixture was stirred at room temperature for 16 hr. The reaction mixture was poured into water, and the mixture was extracted with ethyl acetate. The organic layer was dried over anhydrous sodium sulfate, and the solvent was evaporated under reduced pressure to give the title compound (0.08 g).

$^1$H NMR (400 MHz, CDCl$_3$) δ 1.31-1.39 (3H, m), 1.70-1.76 (2H, m), 1.97-2.12 (3H, m), 3.23 (1H, brs), 3.30-3.40 (1H, m), 3.65-3.75 (4H, m), 4.03 (2H, s), 5.56-5.65 (2H, m), 5.69 (1H, d, J=7.6 Hz), 6.45 (1H, t, J=2.0 Hz), 6.88 (1H, dd, J=18.0, 11.2 Hz), 7.27-7.30 (2H, m, overlapped with CDCl$_3$ signal), 7.61 (2H, d, J=8.4 Hz), 7.70 (1H, d, J=1.6 Hz), 7.89 (1H, d, J=2.0 Hz).

M) rac-4-chloro-3-hydroxy-2-(trans-2-hydroxycyclohexyl)-5-methoxy-6-[4-(1H-pyrazol-1-yl)benzyl]-2,3-dihydro-1H-isoindol-1-one To a solution of rac-3-chloro-2-ethenyl-N-(trans-2-hydroxycyclohexyl)-4-methoxy-5-[4-(1H-pyrazol-1-yl)benzyl]benzamide (0.08 g) in a mixed solvent of acetone (2.00 mL)-acetonitrile (2.00 mL)-water (2.00 mL) were added potassium osmate(VI) dihydrate (5.00 mg) and sodium periodate (0.12 g), and the mixture was stirred at room temperature for 16 hr. The reaction mixture was diluted with saturated aqueous sodium thiosulfate solution, and the mixture was extracted with ethyl acetate. The organic layer was dried over anhydrous sodium sulfate, and the solvent was evaporated under reduced pressure to give the title compound (0.07 g) as a crude product. This compound was used in the next step without an additional purification.

MS: [M+Na]$^+$ 450.1.

N) rac-4-chloro-2-(trans-2-hydroxycyclohexyl)-5-methoxy-6-(4-(1H-pyrazol-1-yl)benzyl)isoindolin-1-one To a solution of rac-4-chloro-3-hydroxy-2-(trans-2-hydroxycyclohexyl)-5-methoxy-6-[4-(1H-pyrazol-1-yl)benzyl]-2,3-dihydro-1H-isoindol-1-one (0.07 g) in dichloromethane (2.00 mL) was added trifluoroacetic acid (0.50 mL) under ice-cooling, and the mixture was stirred for 15 min. Then, triethylsilane (0.40 mL) was added thereto, and the mixture was stirred at room temperature for 1 hr. The reaction mixture was poured into saturated aqueous sodium bicarbonate solution, and the mixture was extracted with ethyl acetate (×2). The organic layer was dried over anhydrous sodium sulfate, and the solvent was evaporated under reduced pressure. The residue was purified by prep-HPLC, then lyophilized to give the title compound (0.02 g).

$^1$H NMR (400 MHz, CDCl$_3$) δ 1.35-1.45 (3H, m), 1.50-1.60 (1H, m, overlapped with water signal), 1.81 (2H, d, J=12.0 Hz), 1.91 (1H, d, J=12.0 Hz), 2.13-2.33 (2H, m), 3.60-3.70 (1H, m), 3.78 (3H, s), 4.03-4.12 (3H, m), 4.37 (2H, q, J=17.2 Hz), 6.44 (1H, t, J=2.0 Hz), 7.20-7.30 (2H, m, overlapped with CDCl$_3$ signal), 7.57-7.62 (3H, m), 7.70 (1H, d, J=1.2 Hz), 7.88 (1H, d, J=2.4 Hz).

Example 13

2-((1S,2S)-2-hydroxycyclopentyl)-4,5-dimethyl-6-(4-(1-methyl-1H-pyrazol-3-yl)benzyl)isoindolin-1-one A) 1-methyl-1H-pyrazol-3-yl trifluoromethanesulfonate To a solution of 1-methyl-1H-pyrazol-3-ol (2.92 g) in pyridine (50.0 mL) was added trifluoromethanesulfonic anhydride (6.03 mL) under ice-cooling, and the mixture was stirred for 1 hr. The reaction mixture was diluted with saturated aqueous sodium bicarbonate solution, and the mixture was extracted with ethyl acetate. The organic layer was washed with saturated brine, and dried over anhydrous sodium sulfate, and the solvent was evaporated under reduced pressure. The residue was purified by silica gel column chromatography (ethyl acetate/hexane) to give the title compound (5.44 g).

$^1$H NMR (300 MHz, CDCl$_3$) δ 3.87 (3H, s), 6.11 (1H, d, J=2.3 Hz), 7.32 (1H, d, J=2.3 Hz).

B) [4-(1-methyl-1H-pyrazol-3-yl)phenyl]methanol

A mixture of [4-(hydroxymethyl)phenyl]boronic acid (4.46 g), 1-methyl-1H-pyrazol-3-yl trifluoromethanesulfonate (4.50 g), cesium carbonate (19.1 g) and [1,1'-bis(diphenylphosphino)ferrocene]dichloropalladium(II)dichloromethane adduct (0.80 g) in toluene (15.0 mL)-ethanol (1.00 mL)-water (1.00 mL) was subjected to microwave irradiation at 150° C. for 1 hr. The reaction mixture was diluted with ethyl acetate, and the insoluble substance was removed by filtration. The filtrate was washed successively with saturated aqueous sodium bicarbonate solution and saturated brine, and dried over anhydrous sodium sulfate, and the solvent was evaporated under reduced pressure. The residue was purified by silica gel column chromatography (ethyl acetate/hexane) to give the title compound (1.00 g).

$^1$H NMR (300 MHz, CDCl$_3$) δ 3.95 (3H, s), 4.71 (2H, d, J=6.0 Hz), 6.54 (1H, d, J=2.3 Hz), 7.33-7.45 (1H, m), 7.73-7.87 (1H, m).

C) 3-[4-(chloromethyl)phenyl]-1-methyl-1H-pyrazole

To a solution of [4-(1-methyl-1H-pyrazol-3-yl)phenyl]methanol (1.00 g) in THF (15.0 mL) was added dropwise thionyl chloride (0.58 mL) under ice-cooling, and the mixture was stirred at 17° C. for 16 hr. The reaction mixture was diluted with water and ethyl acetate, and saturated sodium bicarbonate was added thereto. The organic layer was washed with saturated brine, and dried over anhydrous sodium sulfate, and the solvent was evaporated under reduced pressure. The residue was purified by silica gel column chromatography (ethyl acetate/hexane) to give the title compound (0.65 g).

$^1$H NMR (300 MHz, CDCl$_3$) δ 3.95 (3H, s), 4.61 (2H, s), 6.49-6.57 (1H, m), 7.33-7.44 (3H, m), 7.74-7.82 (2H, m).

D) 2-amino-5-bromo-3,4-dimethylbenzoic acid

To a solution of 2-amino-3,4-dimethylbenzoic acid (50.0 g) in DMSO (500 mL) was added hydrobromic acid (174 mL) while keeping the internal temperature at 25 to 30° C., and the mixture was stirred overnight at room temperature. To the reaction mixture was added water (500 mL), and the mixture was stirred for 30 min. The precipitate was collected by filtration, and washed with water to give the title compound (102 g: containing DMSO).

MS: [M−H]+ 241.9.

E) methyl 2-amino-5-bromo-3,4-dimethylbenzoate

To a solution of 2-amino-5-bromo-3,4-dimethylbenzoic acid (73.9 g) in DMF (750 mL) was added cesium carbonate (148 g), and the mixture was stirred at room temperature for 30 min. To this reaction mixture was added dropwise methyl iodide (22.7 mL) at room temperature, and the mixture was stirred overnight. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (56.8 g).

MS: [M+H]+ 258.1.

F) methyl 5-bromo-2-hydroxy-3,4-dimethylbenzoate

To an aqueous solution (160 mL) of methyl 2-amino-5-bromo-3,4-dimethylbenzoate (28.0 g) in 25% sulfuric acid was added dropwise an aqueous solution (80.0 mL) of sodium nitrite (11.2 g) over 50 min at the internal temperature of 2-3° C. under ice-cooling. Then, 5% aqueous sulfuric acid solution (1600 mL) was added dropwise thereto over 50 min at 0-15° C. The reaction mixture was stirred at 100° C. for 2 hr. The reaction mixture was allowed to be cooled to room temperature, and the precipitate was collected by filtration, and washed with water to give the title compound (25.7 g).

MS: [M−H]+ 256.9.

G) methyl 2-hydroxy-3,4-dimethyl-5-(4,4,5,5-tetramethyl-1,3,2-dioxaborolan-2-yl)benzoate To a solution of methyl 5-bromo-2-hydroxy-3,4-dimethylbenzoate (25.7 g) in toluene (500 mL) were added bis(pinacolato)diboron (37.8 g), potassium acetate (29.2 g) and trans-dichlorobis(triphenylphosphine)palladium(II) (0.70 g), and the mixture was stirred under argon atmosphere at 100° C. for 2 hr. To the reaction mixture was again added trans-dichlorobis(triphenylphosphine)palladium(II) (0.70 g), and the mixture was stirred overnight at 100° C. The reaction mixture was allowed to be cooled to room temperature, water was added thereto, and the mixture was extracted with ethyl acetate. The organic layer was washed with water and saturated brine, and dried over anhydrous magnesium sulfate, and the solvent was evaporated under reduced pressure. The residue was collected by filtration, and washed with ethyl acetate to give the title compound (18.3 g).

MS: [M−H]+ 305.1.

H) methyl 2-hydroxy-3,4-dimethyl-5-(4-(1-methyl-1H-pyrazol-3-yl)benzyl)benzoate

To a solution of methyl 2-hydroxy-3,4-dimethyl-5-(4,4,5,5-tetramethyl-1,3,2-dioxaborolan-2-yl)benzoate (0.97 g), 3-[4-(chloromethyl)phenyl]-1-methyl-1H-pyrazole (0.65 g) and sodium carbonate (0.67 g) in a mixed solvent of 1,2-dimethoxyethane (12.0 mL)-water (4.00 mL) was added tetrakis(triphenylphosphine)palladium(0) (0.18 g) under argon atmosphere, and the mixture was stirred overnight at 80° C. To the reaction mixture was added water, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.65 g).

$^1$H NMR (300 MHz, CDCl$_3$) δ 2.14 (3H, s), 2.20 (3H, s), 3.91 (3H, s), 3.94 (3H, s), 3.97 (2H, s), 6.49 (1H, d, J=2.3 Hz), 7.10 (2H, d, J=8.3 Hz), 7.35 (1H, d, J=2.3 Hz), 7.53 (1H, s), 7.65-7.72 (2H, m), 10.99 (1H, s).

I) methyl 3,4-dimethyl-5-(4-(1-methyl-1H-pyrazol-3-yl)benzyl)-2-(((trifluoromethyl)sulfonyl)oxy)benzoate To a solution of methyl 2-hydroxy-3,4-dimethyl-5-(4-(1-methyl-1H-pyrazol-3-yl)benzyl)benzoate (1.00 g) in DMF (12.0 mL) were added sodium hydride (0.14 g) and N-phenylbis(trifluoromethanesulfonimide) (1.12 g) under ice-cooling, and the mixture was stirred for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (1.30 g).

$^1$H NMR (300 MHz, CDCl$_3$) δ 2.21 (3H, s), 2.30 (3H, s), 3.91 (3H, s), 3.94 (3H, s), 4.05 (2H, s), 6.50 (1H, d, J=2.3 Hz), 7.10 (1H, d, J=8.1 Hz), 7.36 (1H, d, J=2.3 Hz), 7.65-7.74 (1H, m).

J) methyl 3,4-dimethyl-5-(4-(1-methyl-1H-pyrazol-3-yl)benzyl)-2-vinylbenzoate

A solution of methyl 3,4-dimethyl-5-(4-(1-methyl-1H-pyrazol-3-yl)benzyl)-2-(((trifluoromethyl)sulfonyl)oxy)benzoate (1.30 g), tributylvinyltin (1.28 g), trans-dichlorobis(triphenylphosphine)palladium(II) (0.10 g) and lithium chloride (0.80 g) in DMF (12.0 mL) was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.96 g).

$^1$H NMR (300 MHz, CDCl$_3$) δ 2.17 (3H, s), 2.26 (3H, s), 3.81 (3H, s), 3.94 (3H, s), 4.04 (2H, s), 5.11 (1H, dd, J=17.8, 1.9 Hz), 5.44 (1H, dd, J=11.2, 1.8 Hz), 6.49 (1H, d, J=2.3 Hz), 7.04 (1H, dd, J=17.8, 11.3 Hz), 7.12 (2H, d, J=8.5 Hz), 7.32-7.39 (2H, m), 7.44 (1H, s), 7.65-7.72 (1H, m).

K) methyl 2-formyl-3,4-dimethyl-5-(4-(1-methyl-1H-pyrazol-3-yl)benzyl)benzoate

To a solution of methyl 3,4-dimethyl-5-(4-(1-methyl-1H-pyrazol-3-yl)benzyl)-2-vinylbenzoate (0.96 g) in a mixed solvent of acetone (10.0 mL)-acetonitrile (10.0 mL)-water (10.0 mL) were added osmium oxide (fixed catalyst I) (0.34 g) and sodium periodate (2.86 g), and the mixture was stirred overnight at room temperature. The reaction mixture was concentrated under reduced pressure, and the residue was diluted with ethyl acetate and water. The insoluble substance was removed by filtration, and the filtrate was washed with saturated aqueous sodium bicarbonate solution, water and saturated brine, and dried over anhydrous sodium sulfate. The solvent was evaporated under reduced pressure, and the residue was purified by silica gel column chromatography (ethyl acetate/hexane) to give the title compound (0.17 g).
MS: [M+H]$^+$ 363.2.

L) 2-((1S,2S)-2-hydroxycyclopentyl)-4,5-dimethyl-6-(4-(1-methyl-1H-pyrazol-3-yl)benzyl)isoindolin-1-one A solution of methyl 2-formyl-3,4-dimethyl-5-(4-(1-methyl-1H-pyrazol-3-yl)benzyl)benzoate (0.09 g), (1S,2S)-2-aminocyclopentanol hydrochloride (0.03 g), triethylamine (0.03 mL) and anhydrous magnesium sulfate (0.06 g) in THF (1.80 mL) was stirred at room temperature for 46 hr under nitrogen atmosphere. The insoluble substance was removed by filtration, and the filtrate was concentrated under reduced pressure. The residue was diluted with methanol (1.80 mL) and THF (1.80 mL), sodium triacetoxyborohydride (0.10 g) was added thereto, and the mixture was stirred at room temperature for 7.5 hr. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.04 g).
$^1$H NMR (300 MHz, DMSO-d$_6$) δ 1.47-1.77 (4H, m), 1.81-1.97 (2H, m), 2.20 (3H, s), 2.23 (3H, s), 3.86 (3H, s), 4.07-4.30 (4H, m), 4.39 (2H, s), 4.89 (1H, d, J=4.9 Hz), 6.61 (1H, d, J=2.3 Hz), 7.12 (2H, d, J=7.9 Hz), 7.33 (1H, s), 7.65-7.71 (3H, m).

Example 14

4,5-dimethyl-6-(4-(1-methyl-1H-1,2,3-triazol-4-yl)benzyl)-2-((2S)-tetrahydrofuran-2-ylmethyl)isoindolin-1-one A)
[4-(1-methyl-1H-1,2,3-triazol-4-yl)phenyl]methanol A mixture of [4-(hydroxymethyl)phenyl]boronic acid (7.10 g), 4-bromo-1-methyl-1H-1,2-3-triazole (5.00 g), sodium carbonate (6.59 g) and tetrakis(triphenylphosphine)palladium(0) (3.59 g) in a mixed solvent of water (30.0 mL)-1,4-dioxane (100 mL) was heated with reflux for 16 hr under nitrogen atmosphere. The reaction mixture was allowed to be cooled to room temperature, the organic layer was concentrated under reduced pressure, and the residue was extracted with dichloromethane (×3). The combined extracts were dried over anhydrous sodium sulfate, and the solvent was evaporated under reduced pressure. The residue was purified by silica gel column chromatography (ethyl acetate/petroleum ether) to give the title compound (3.40 g).
MS: [M+H]$^+$ 189.9.

B) 4-[4-(bromomethyl)phenyl]-1-methyl-1H-1,2,3-triazole

To a solution of [4-(1-methyl-1H-1,2,3-triazol-4-yl)phenyl]methanol (3.40 g) in dichloromethane (130 mL) was added dropwise phosphorus tribromide (23.0 g) under ice-cooling, and the mixture was stirred at 20° C. for 16 hr. The reaction mixture was concentrated under reduced pressure, the residue was poured into saturated aqueous sodium bicarbonate solution, and the mixture was extracted with dichloromethane (×3). The combined organic layers were washed with water and saturated brine, and dried over anhydrous sodium sulfate, and the solvent was evaporated under reduced pressure. The residue was purified by silica gel column chromatography (ethyl acetate/petroleum ether) to give the title compound (3.50 g) as a mixture with phosphine oxide. This mixture was diluted with tert-butyl methyl ether, and the mixture was stirred at 20° C. for 16 hr. The precipitate was collected by filtration, and dried under reduced pressure to give the title compound (3.40 g).
MS: [M+H]$^+$ 251.8.

C) methyl 2-hydroxy-3,4-dimethyl-5-(4-(1-methyl-1H-1,2,3-triazol-4-yl)benzyl)benzoate To a mixture of methyl 2-hydroxy-3,4-dimethyl-5-(4,4,5,5-tetramethyl-1,3,2-dioxaborolan-2-yl)benzoate (0.76 g), 4-[4-(bromomethyl)phenyl]-1-methyl-1H-1,2,3-triazole (0.63 g) and sodium carbonate (0.53 g) in 1,2-dimethoxyethane (12.0 mL)-water (4.00 mL) was added tetrakis(triphenylphosphine)palladium(0) (0.29 g), and the mixture was stirred overnight at 80° C. under argon atmosphere. To the reaction mixture were added water and ethyl acetate, and the mixture was partitioned. The organic layer was washed with water and saturated brine, and dried over anhydrous sodium sulfate, and the solvent was evaporated under reduced pressure. The residue was purified by silica gel column chromatography (ethyl acetate/hexane) to give the title compound (0.60 g).
MS: [M+H]$^+$ 352.2.

D) methyl 3,4-dimethyl-5-(4-(1-methyl-1H-1,2,3-triazol-4-yl)benzyl)-2-(((trifluoromethyl)sulfonyl)oxy)benzoate To a solution of methyl 2-hydroxy-3,4-dimethyl-5-(4-(1-methyl-1H-1,2,3-triazol-4-yl)benzyl)benzoate (0.60 g) in DMF (12.0 mL) were added sodium hydride (0.08 g) and N-phenylbis(trifluoromethanesulfonimide)(0.67 g) under ice-cooling, and the mixture was stirred for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.60 g).
MS: [M+H]$^+$ 484.1.

E) methyl 3,4-dimethyl-5-(4-(1-methyl-1H-1,2,3-triazol-4-yl)benzyl)-2-vinylbenzoate To a solution of methyl 3,4-dimethyl-5-(4-(1-methyl-1H-1,2,3-triazol-4-yl)benzyl)-2-(((trifluoromethyl)sulfonyl)oxy)benzoate (0.60 g) in DMF (12.0 mL) were added tributylvinyltin (1.28 g), trans-dichlorobis(triphenylphosphine)palladium(II) (0.10 g) and lithium chloride (0.80 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.42 g).

MS: [M+H]$^+$ 362.2.

F) methyl 2-formyl-3,4-dimethyl-5-(4-(1-methyl-1H-1,2,3-triazol-4-yl)benzyl)benzoate To a solution of methyl 3,4-dimethyl-5-(4-(1-methyl-1H-1,2,3-triazol-4-yl)benzyl)-2-vinylbenzoate (0.42 g) in a mixed solvent of acetone (10.0 mL)-acetonitrile (10.0 mL)-water (10.0 mL) were added osmium oxide (fixed catalyst I) (0.15 g) and sodium periodate (1.24 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.26 g) as a crude product.

MS: [M+H]$^+$ 364.2.

G) 3-hydroxy-4,5-dimethyl-6-(4-(1-methyl-1H-1,2,3-triazol-4-yl)benzyl)-2-(((2S)-tetrahydrofuran-2-yl)methyl)isoindolin-1-one To a solution of methyl 2-formyl-3,4-dimethyl-5-(4-(1-methyl-1H-1,2,3-triazol-4-yl)benzyl)benzoate (0.13 g) in THF (3.00 mL) were added 1-((2S)-tetrahydrofuran-2-yl)methanamine (0.04 mL) and anhydrous magnesium sulfate (0.04 g), and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was is purified by silica gel column chromatography (ethyl acetate/hexane) to give the title compound (0.11 g).

MS: [M+H]$^+$ 433.3.

H) 4,5-dimethyl-6-(4-(1-methyl-1H-1,2,3-triazol-4-yl)benzyl)-2-((2S)-tetrahydrofuran-2-ylmethyl)isoindolin-1-one To a solution of 3-hydroxy-4,5-dimethyl-6-(4-(1-methyl-1H-1,2,3-triazol-4-yl)benzyl)-2-(((2S)-tetrahydrofuran-2-yl)methyl)isoindolin-1-one (0.11 g) in trifluoroacetic acid (1.50 mL) was added triethylsilane (0.08 mL), and the mixture was stirred at room temperature for 15 min. The reaction mixture was concentrated under reduced pressure, and the residue was purified by silica gel column chromatography (ethyl acetate/hexane) to give the title compound (0.08 g).

$^1$H NMR (300 MHz, DMSO-d$_6$) δ 1.49-1.62 (1H, m), 1.74-1.98 (3H, m), 2.21 (6H, s), 3.45-3.56 (1H, m), 3.57-3.68 (2H, m), 3.74-3.84 (1H, m), 4.01-4.14 (6H, m), 4.39-4.54 (2H, m), 7.19 (2H, d, J=7.9 Hz), 7.34 (1H, s), 7.73 (2H, d, J=8.3 Hz), 8.44 (1H, s).

Example 15

2-(2-hydroxy-2-methylpropyl)-4,5-dimethyl-6-(4-(1H-pyrazol-1-yl)benzyl)isoindolin-1-one

A) methyl 5-(4-(1H-pyrazol-1-yl)benzyl)-2-hydroxy-3,4-dimethylbenzoate

To a solution of methyl 2-hydroxy-3,4-dimethyl-5-(4,4,5,5-tetramethyl-1,3,2-dioxaborolan-2-yl)benzoate (0.60 g) in DME (12.0 mL) were added 1-(4-(bromomethyl)phenyl)-1H-pyrazole (0.51 g), [1,1'-bis(diphenylphosphino)ferrocene]dichloropalladium(II)dichloromethane adduct (0.08 g) and 2 mol/L aqueous sodium carbonate solution (1.96 mL), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.54 g).

MS: [M+H]$^+$ 337.2.

B) methyl 5-(4-(1H-pyrazol-1-yl)benzyl)-3,4-dimethyl-2-vinylbenzoate

To a solution of methyl 5-(4-(1H-pyrazol-1-yl)benzyl)-2-hydroxy-3,4-dimethylbenzoate (0.54 g) in DMF (10 mL) was added sodium hydride (0.08 g) under ice-cooling, and the mixture was stirred for 30 min. To this reaction mixture was added N-phenylbis(trifluoromethanesulfonimide) (0.63 g), and the mixture was stirred at room temperature for 1 hr. To the reaction mixture was added 1N hydrochloric acid, and the mixture was extracted with ethyl acetate. The organic layer was washed with water and saturated brine, and dried over anhydrous magnesium sulfate, and the solvent was evaporated under reduced pressure. The obtained crude methyl 3,4-dimethyl-5-[4-(1H-pyrazol-1-yl)benzyl]-2-{[(trifluoromethyl)sulfonyl]oxy}benzoate was used in the next step without an additional purification.

MS: [M+H]$^+$ 469.1.

The above-mentioned compound was dissolved in DMF (10 mL), tributylvinyltin (0.71 mL), trans-dichlorobis(triphenylphosphine)palladium(II) (0.06 g) and lithium chloride (0.50 g) were added thereto, and the mixture was stirred overnight at 90° C. under argon atmosphere. To the reaction mixture was again added trans-dichlorobis(triphenylphosphine)palladium(II) (0.11 g), and the mixture was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.19 g).

MS: [M+H]$^+$ 347.2.

C) methyl 5-(4-(1H-pyrazol-1-yl)benzyl)-2-formyl-3,4-dimethylbenzoate

To a solution of methyl 5-(4-(1H-pyrazol-1-yl)benzyl)-3,4-dimethyl-2-vinylbenzoate (0.40 g) in a mixed solvent of acetone (8.00 mL)-acetonitrile (8.00 mL)-water (8.00 mL) were added osmium oxide (fixed catalyst I) (0.15 g) and sodium periodate (1.24 g), and the mixture was stirred overnight at room temperature. The reaction mixture was filtered, and the filtrate was concentrated under reduced pressure. To the residue was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.11 g).

MS: [M+H]$^+$ 349.1.

D) 2-(2-hydroxy-2-methylpropyl)-4,5-dimethyl-6-(4-(1H-pyrazol-1-yl)benzyl)isoindolin-1-one To a solution of methyl 5-(4-(1H-pyrazol-1-yl)benzyl)-2-formyl-3,4-dimethylbenzoate (0.11 g) in THF (4.00 mL) was added 1-amino-2-methylpropan-2-ol (0.03 g), and the mixture was stirred at room temperature for 2 hr. The reaction mixture was concentrated, and the residue was diluted with methanol (4.0 mL). Sodium triacetoxyborohydride (0.11 g) was added thereto under argon atmosphere, and the mixture was stirred overnight at room temperature. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by NH silica gel column chromatography (ethyl acetate/hexane) to give the title compound (0.04 g).

$^1$H NMR (300 MHz, CDCl$_3$) δ 1.31 (6H, s), 2.23 (3H, s), 2.26 (3H, s), 3.27 (1H, s), 3.63 (2H, s), 4.13 (2H, s), 4.51 (2H, s), 6.43-6.47 (1H, m), 7.19 (2H, d, J=8.5 Hz), 7.56-7.62 (3H, m), 7.71 (1H, d, J=1.5 Hz), 7.88 (1H, d, J=2.5 Hz).

Example 16

6-(2-fluoro-4-(1H-pyrazol-1-yl)benzyl)-2-((1S,2S)-2-hydroxycyclopentyl)-4,5-dimethylisoindolin-1-one

A) methyl 2-fluoro-4-(1H-pyrazol-1-yl)benzoate

To a solution of (3-fluoro-4-(methoxycarbonyl)phenyl) boronic acid (2.40 g) and 1H-pyrazole (0.99 g) in methanol (54.0 mL) was added copper(I) oxide (0.10 g), and the mixture was stirred overnight at 50° C. The reaction mixture was concentrated under reduced pressure, and the residue was purified by silica gel column chromatography (ethyl acetate/hexane) to give the title compound (0.89 g).

MS: [M+H]$^+$ 221.1.

B) (2-fluoro-4-(1H-pyrazol-1-yl)phenyl)methanol

To a solution of lithium aluminium hydride (0.16 g) in THF (5.50 mL) was added a solution of methyl 2-fluoro-4-(1H-pyrazol-1-yl)benzoate (0.89 g) in THF (5.50 mL) under ice-cooling, and the mixture was stirred for 1 hr. To the reaction solution was added water, the insoluble substance was removed by filtration, and the filtrate was concentrated under reduced pressure to give the title compound (0.71 g) as a crude product.

MS: [M+H]$^+$ 193.1.

C) 1-(4-(chloromethyl)-3-fluorophenyl)-1H-pyrazole

To a solution of (2-fluoro-4-(1H-pyrazol-1-yl)phenyl) methanol (0.71 g) in THF (15.0 mL) was added thionyl chloride (0.40 mL) under ice-cooling, and the mixture was stirred at room temperature for 16 hr. The reaction mixture was diluted with ethyl acetate, saturated aqueous sodium bicarbonate was added thereto, and the mixture was partitioned. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.50 g).

MS: [M+H]$^+$ 211.1.

D) methyl 5-(2-fluoro-4-(1H-pyrazol-1-yl)benzyl)-2-hydroxy-3,4-dimethylbenzoate To a mixture of methyl 2-hydroxy-3,4-dimethyl-5-(4,4,5,5-tetramethyl-1,3,2-dioxaborolan-2-yl)benzoate (0.51 g), 1-(4-(chloromethyl)-3-fluorophenyl)-1H-pyrazole (0.35 g) and sodium carbonate (0.35 g) in 1,2-dimethoxyethane (7.80 mL)-water (2.60 mL) was added tetrakis(triphenylphosphine)palladium(0) (0.10 g), and the mixture was stirred overnight at 80° C. under argon atmosphere. To the reaction mixture were added water and ethyl acetate, and the mixture was partitioned. The organic layer was washed with water and saturated brine, and dried over anhydrous sodium sulfate, and the solvent was evaporated under reduced pressure. The residue was purified by silica gel column chromatography (ethyl acetate/hexane) to give the title compound (0.54 g).

MS: [M+H]$^+$ 355.2.

E) methyl 5-(2-fluoro-4-(1H-pyrazol-1-yl)benzyl)-3,4-dimethyl-2-(((trifluoromethyl)sulfonyl)oxy)benzoate To a solution of methyl 5-(2-fluoro-4-(1H-pyrazol-1-yl) benzyl)-2-hydroxy-3,4-dimethylbenzoate (0.54 g) in DMF (11.0 mL) were added sodium hydride (0.07 g) and N-phenylbis(trifluoromethanesulfonimide) (0.60 g) under ice-cooling, and the mixture was stirred for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.50 g).

MS: [M+H]$^+$ 487.1.

F) methyl 5-(2-fluoro-4-(1H-pyrazol-1-yl)benzyl)-3,4-dimethyl-2-vinylbenzoate To a solution of methyl 5-(2-fluoro-4-(1H-pyrazol-1-yl) benzyl)-3,4-dimethyl-2-(((trifluoromethyl)sulfonyl)oxy) benzoate (0.50 g) in DMF (10.0 mL) were added tributylvinyltin (0.50 g), trans-dichlorobis(triphenylphosphine) palladium(II) (0.04 g) and lithium chloride (0.32 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.40 g).

MS: [M+H]$^+$ 365.2.

G) methyl 5-(2-fluoro-4-(1H-pyrazol-1-yl)benzyl)-2-formyl-3,4-dimethylbenzoate To a solution of methyl 5-(2-fluoro-4-(1H-pyrazol-1-yl) benzyl)-3,4-dimethyl-2-vinylbenzoate (0.40 g) in a mixed solvent of acetone (5.00 mL)-acetonitrile (5.00 mL)-water (5.00 mL) were added osmium oxide (fixed catalyst I) (0.14 g) and sodium periodate (1.17 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure to give the title compound (0.40 g) as a crude product. This compound was used in the next step without an additional purification.

H) 6-(2-fluoro-4-(1H-pyrazol-1-yl)benzyl)-2-((1S, 2S)-2-hydroxycyclopentyl)-4,5-dimethylisoindolin-1-one A solution of methyl 5-(2-fluoro-4-(1H-pyrazol-1-yl)benzyl)-2-formyl-3,4-dimethylbenzoate (0.17 g), (1S,2S)-2-aminocyclopentanol hydrochloride (0.06 g), triethylamine (0.06 mL) and anhydrous magnesium sulfate (0.10 g) in THF (3.40 mL) was stirred at room temperature for 10 hr. The insoluble substance was removed by filtration, and the filtrate was concentrated under reduced pressure. The residue was diluted with methanol (3.40 mL) and THF (3.40 mL), sodium triacetoxyborohydride (0.19 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.07 g).
$^1$H NMR (300 MHz, DMSO-d$_6$) δ 1.45-1.60 (1H, m), 1.62-1.79 (3H, m), 1.80-1.98 (2H, m), 2.24 (3H, s), 2.25 (3H, s), 4.08-4.29 (4H, m), 4.39 (2H, s), 4.88 (1H, d, J=4.9 Hz), 6.52-6.58 (1H, m), 7.15 (1H, t, J=8.4 Hz), 7.23 (1H, s), 7.63 (1H, dd, J=8.3, 2.1 Hz), 7.68-7.77 (2H, m), 8.52 (1H, d, J=2.5 Hz).

Example 17

1,5-anhydro-2-(6-(4-chlorobenzyl)-4,5-dimethyl-1-oxo-1,3-dihydro-2H-isoindol-2-yl)-2,4-dideoxy-L-threo-pentitol A) methyl 5-(4-chlorobenzyl)-2-hydroxy-3,4-dimethylbenzoate To a solution of methyl 2-hydroxy-3,4-dimethyl-5-(4,4,5,5-tetramethyl-1,3,2-dioxaborolan-2-yl)benzoate (0.70 g) in DME (14.0 mL) were added 1-(bromomethyl)-4-chlorobenzene (0.49 g), [1,1'-bis(diphenylphosphino)ferrocene]dichloropalladium(II)dichloromethane adduct (0.09 g) and 2 mol/L aqueous sodium carbonate solution (2.29 mL), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.50 g).
MS: [M+H]$^+$ 305.1.

B) methyl 5-(4-chlorobenzyl)-3,4-dimethyl-2-vinylbenzoate

To a solution of methyl 5-(4-chlorobenzyl)-2-hydroxy-3,4-dimethylbenzoate (0.50 g) in DMF (10.0 mL) was added sodium hydride (0.08 g) under ice-cooling, and the mixture was stirred at room temperature for 30 min. To this reaction mixture was added N-phenylbis(trifluoromethanesulfonimide)(0.65 g) under ice-cooling, and the mixture was stirred at room temperature for 1 hr. To the reaction mixture was added 1N hydrochloric acid, and the mixture was extracted with ethyl acetate. The organic layer was washed with water and saturated brine, and dried over anhydrous magnesium sulfate, and the solvent was evaporated under reduced pressure. The obtained crude methyl 5-(4-chlorobenzyl)-3,4-dimethyl-2-{[(trifluoromethyl)sulfonyl]oxy}benzoate was used in the next step without an additional purification.

The above-mentioned compound was dissolved in DMF (10.0 mL), to the solution were added tributylvinyltin (0.72 mL), trans-dichlorobis(triphenylphosphine)palladium(II) (0.23 g) and lithium chloride (0.52 g), and the mixture was stirred overnight at 90° C. under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.17 g).
MS: [M+H]$^+$ 315.2.

C) methyl 5-(4-chlorobenzyl)-2-formyl-3,4-dimethylbenzoate

To a solution of methyl 5-(4-chlorobenzyl)-3,4-dimethyl-2-vinylbenzoate (0.17 g) in a mixed solvent of acetone (4.00 mL)-acetonitrile (4.00 mL)-water (4.00 mL) were added osmium oxide (fixed catalyst I) (0.07 g) and sodium periodate (0.58 g), and the mixture was stirred overnight at room temperature under argon atmosphere. The reaction mixture was filtered, the filtrate was concentrated under reduced pressure, and the residue was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.02 g).
MS: [M+H]$^+$ 317.1.

D) 1,5-anhydro-2-(6-(4-chlorobenzyl)-4,5-dimethyl-1-oxo-1,3-dihydro-2H-isoindol-2-yl)-2,4-dideoxy-L-threo-pentitol To a solution of methyl 5-(4-chlorobenzyl)-2-formyl-3,4-dimethylbenzoate (0.02 g) in THF (1.00 mL) was added (3S,4S)-3-aminotetrahydro-2H-pyran-4-ol (8.14 mg), and the mixture was stirred at room temperature for 2 hr. The reaction mixture was concentrated, and the residue was diluted with methanol (1.00 mL). Sodium triacetoxyborohydride (0.02 g) was added thereto under argon atmosphere, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by reverse-phase HPLC. The fractions were combined, saturated aqueous sodium hydrogencarbonate solution was added thereto, and the mixture was extracted with ethyl acetate. The organic layer was dried over anhydrous magnesium sulfate, and the solvent was evaporated under reduced pressure to give the title compound (5.60 mg).

¹H NMR (300 MHz, CDCl₃) δ 1.72-1.88 (1H, m), 2.09-2.17 (1H, m), 2.20 (3H, s), 2.25 (3H, s), 3.45-3.62 (2H, m), 4.01-4.20 (6H, m), 4.26-4.50 (2H, m), 7.02 (2H, d, J=8.5 Hz), 7.19-7.25 (2H, m), 7.51 (1H, s). 1H undetected.

Example 18-1

2-[(3S,4S)-4-hydroxytetrahydro-2H-pyran-3-yl]-6-(4-methoxybenzyl)-4,5-dimethyl-2,3-dihydro-1H-isoindol-1-one Alias; 1,5-anhydro-2,4-dideoxy-2-(6-(4-methoxybenzyl)-4,5-dimethyl-1-oxo-1,3-dihydro-2H-isoindol-2-yl)-L-threo-pentitol A) methyl 2-hydroxy-5-(4-methoxybenzyl)-3,4-dimethylbenzoate To a mixture of methyl 2-hydroxy-3,4-dimethyl-5-(4,4,5,5-tetramethyl-1,3,2-dioxaborolan-2-yl)benzoate (18.3 g), 1-(chloromethyl)-4-methoxybenzene (9.38 g) and sodium carbonate (12.7 g) in 1,2-dimethoxyethane (255 mL)-water (85.0 mL) was added tetrakis(triphenylphosphine)palladium (0) (3.46 g), and the mixture was stirred overnight at 80° C. under argon atmosphere. To the reaction mixture were added water and ethyl acetate, and the organic layer was separated, washed with saturated brine. The organic layer was dried over anhydrous sodium sulfate, and the solvent was evaporated under reduced pressure. To the residue was added a mixed solvent of ethyl acetate-diisopropyl ether, and the solid was collected by filtration to give the title compound (11.12 g). The filtrate was concentrated, and the residue was purified by silica gel column chromatography (ethyl acetate/hexane) to give the title compound (4.99 g).

MS: [M+H]⁺ 301.1.

B) methyl 5-(4-methoxybenzyl)-3,4-dimethyl-2-(((trifluoromethyl)sulfonyl)oxy)benzoate To a solution of methyl 2-hydroxy-5-(4-methoxybenzyl)-3,4-dimethylbenzoate (16.1 g) in DMF (300 mL) were added sodium hydride (2.57 g) and N-phenylbis(trifluoromethanesulfonimide)(21.1 g) under ice-cooling, and the mixture was stirred at room temperature for 2.5 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (26.1 g).

¹H NMR (300 MHz, CDCl₃) δ 2.22 (3H, s), 2.31 (3H, s), 3.79 (3H, s), 3.92 (3H, s), 3.99 (2H, s), 6.83 (2H, d, J=8.7 Hz), 7.01 (2H, d, J=8.7 Hz), 7.64 (1H, s).

C) methyl 5-(4-methoxybenzyl)-3,4-dimethyl-2-vinylbenzoate

To a solution of methyl 5-(4-methoxybenzyl)-3,4-dimethyl-2-(((trifluoromethyl)sulfonyl)oxy)benzoate (23.2 g) in DMF (360 mL) were added tributylvinyltin (25.5 g), trans-dichlorobis(triphenylphosphine)palladium(II) (1.88 g) and lithium chloride (16.8 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (13.6 g).

MS: [M+H]⁺ 311.2.

D) methyl 2-formyl-5-(4-methoxybenzyl)-3,4-dimethylbenzoate

To a solution of methyl 5-(4-methoxybenzyl)-3,4-dimethyl-2-vinylbenzoate (13.6 g) in a mixed solvent of acetone (135 mL)-acetonitrile (135 mL)-water (135 mL) were added osmium oxide (fixed catalyst I) (5.57 g) and sodium periodate (46.9 g), and the mixture was stirred overnight at room temperature. The reaction mixture was filtered, and the filtrate was extracted with ethyl acetate. The organic layer was washed with water and saturated brine, and dried over anhydrous magnesium sulfate, and the solvent was evaporated under reduced pressure to give the title compound (13.5 g) as a crude product. This compound was used in the next step without an additional purification.

MS: [M+H]⁺ 313.2.

E) 2-[(3S,4S)-4-hydroxytetrahydro-2H-pyran-3-yl]-6-(4-methoxybenzyl)-4,5-dimethyl-2,3-dihydro-1H-isoindol-1-one Alias; 1,5-anhydro-2,4-dideoxy-2-(6-(4-methoxybenzyl)-4,5-dimethyl-1-oxo-1,3-dihydro-2H-isoindol-2-yl)-L-threo-pentitol To a solution of methyl 2-formyl-5-(4-methoxybenzyl)-3,4-dimethylbenzoate (13.5 g) in THF (270 mL) were added (3S,4S)-3-aminotetrahydro-2H-pyran-4-ol (5.06 g) and anhydrous magnesium sulfate (9.99 g), and the mixture was stirred at room temperature for 5 hr. The insoluble substance was removed by filtration, and the filtrate was concentrated. The residue was diluted with methanol (220 mL)-THF (250 mL), sodium triacetoxyborohydride (18.3 g) was added thereto, and the mixture was stirred at room temperature for 15 hr. The reaction mixture was diluted with ethyl acetate, the mixture was washed with water and saturated brine, and the organic layer was dried over anhydrous magnesium sulfate. The organic layer was concentrated under reduced pressure. The resulting solid was washed with ethyl acetate to give the crude title compound (6.4 g). The filtrate was concentrated under reduced pressure, and the residue was purified by silica gel column chromatography (ethyl acetate/hexane) to give the title compound (0.85 g). The crude title compound and the title compound purified by column were combined, and recrystallized from ethanol to give the title compound (6.48 g).

¹H NMR (300 MHz, DMSO-d₆) δ 1.44-1.65 (1H, m), 1.95 (1H, d, J=11.3 Hz), 2.19 (3H, s), 2.21 (3H, s), 3.33-3.49 (2H, m), 3.71 (4H, s), 3.82-3.96 (3H, m), 4.00 (2H, s), 4.33-4.50 (2H, m), 5.05 (1H, d, J=4.9 Hz), 6.84 (2H, d, J=8.7 Hz), 7.03 (2H, d, J=8.7 Hz), 7.28 (1H, s).

X-ray powder diffraction pattern with specific peaks at d value (or d-spacing)=18.3, 9.8, 9.2, 6.8, 6.1, 5.2, 4.6, 4.2 and 3.8 Å.

Example 18-2

2-[(3S,4S)-4-hydroxytetrahydro-2H-pyran-3-yl]-6-(4-methoxybenzyl)-4,5-dimethyl-2,3-dihydro-1H-isoindol-1-one Alias; 1,5-anhydro-2,4-dideoxy-2-(6-(4-methoxybenzyl)-4,5-dimethyl-1-oxo-1,3-dihydro-2H-isoindol-2-yl)-L-threo-pentitol This compound was also synthesized by the following method.

A) methyl 2-hydroxy-5-(4-methoxybenzyl)-3,4-dimethylbenzoate

To a mixture of methyl 2-hydroxy-3,4-dimethyl-5-(4,4,5,5-tetramethyl-1,3,2-dioxaborolan-2-yl)benzoate (0.40 g), 1-(chloromethyl)-4-methoxybenzene (0.21 g) and sodium carbonate (0.28 g) in 1,2-dimethoxyethane (6.00 mL)-water (2.00 mL) was added tetrakis(triphenylphosphine)palladium (0) (0.08 g), and the mixture was stirred overnight at 80° C. under argon atmosphere. To the reaction mixture was added water, and the mixture was extracted with ethyl acetate. The organic layer was separated, washed with saturated brine, and dried over anhydrous magnesium sulfate, and the solvent was evaporated under reduced pressure. The residue was purified by silica gel column chromatography (ethyl acetate/hexane) to give the title compound (0.30 g).

$^1$H NMR (300 MHz, CDCl$_3$) δ 2.13 (3H, s), 2.19 (3H, s), 3.77 (3H, s), 3.90 (2H, s), 3.91 (3H, s), 6.80 (2H, d, J=8.7 Hz), 6.99 (2H, d, J=8.7 Hz), 7.50 (1H, s), 10.97 (1H, s).

B) methyl 5-(4-methoxybenzyl)-3,4-dimethyl-2-(((trifluoromethyl)sulfonyl)oxy)benzoate To a mixture of methyl 2-hydroxy-5-(4-methoxybenzyl)-3,4-dimethylbenzoate (0.30 g), sodium hydride (0.05 g) and DMF (6.00 mL) was added N-phenylbis(trifluoromethanesulfonimide) (0.39 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.34 g).

$^1$H NMR (300 MHz, CDCl$_3$) δ 2.21 (3H, s), 2.30 (3H, s), 3.78 (3H, s), 3.91 (3H, s), 3.98 (2H, s), 6.78-6.87 (2H, m), 7.00 (2H, d, J=8.7 Hz), 7.63 (1H, s).

C) methyl 5-(4-methoxybenzyl)-3,4-dimethyl-2-vinylbenzoate

To a solution of methyl 5-(4-methoxybenzyl)-3,4-dimethyl-2-(((trifluoromethyl)sulfonyl)oxy)benzoate (0.34 g) in DMF (7.00 mL) were added tributylvinyltin (0.37 g), trans-dichlorobis(triphenylphosphine)palladium(II) (0.03 g) and lithium chloride (0.25 g), and the mixture was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with saturated brine. The organic layer was dried over anhydrous magnesium sulfate, and the solvent was evaporated under reduced pressure. The residue was purified by silica gel column chromatography (ethyl acetate/hexane) to give the title compound (0.20 g).

$^1$H NMR (300 MHz, CDCl$_3$) δ 2.17 (3H, s), 2.26 (3H, s), 3.77 (3H, s), 3.80 (3H, s), 3.97 (2H, s), 5.10 (1H, dd, J=17.7, 1.9 Hz), 5.43 (1H, dd, J=11.3, 1.9 Hz), 6.76-6.86 (2H, m), 6.96-7.09 (3H, m), 7.41 (1H, s).

D) methyl 2-formyl-5-(4-methoxybenzyl)-3,4-dimethylbenzoate

To a solution of methyl 5-(4-methoxybenzyl)-3,4-dimethyl-2-vinylbenzoate (0.19 g) in a mixed solvent of acetone (2.30 mL)-acetonitrile (2.30 mL)-water (2.30 mL) were added osmium oxide (fixed catalyst I) (0.08 g) and sodium periodate (0.67 g), and the mixture was stirred overnight at room temperature. The reaction mixture was filtered, and the filtrate was extracted with ethyl acetate. The organic layer was washed with water and saturated brine, and dried over anhydrous magnesium sulfate, and the solvent was evaporated under reduced pressure to give the title compound (0.19 g) as a crude product. This compound was used in the next step without an additional purification.

MS: [M+H]$^+$ 313.2.

E) 2-[(3S,4S)-4-hydroxytetrahydro-2H-pyran-3-yl]-6-(4-methoxybenzyl)-4,5-dimethyl-2,3-dihydro-1H-isoindol-1-one Alias; 1,5-anhydro-2,4-dideoxy-2-(6-(4-methoxybenzyl)-4,5-dimethyl-1-oxo-1,3-dihydro-2H-isoindol-2-yl)-L-threo-pentitol To a solution of methyl 2-formyl-5-(4-methoxybenzyl)-3,4-dimethylbenzoate (0.10 g) in THF (1.90 mL) were added (3S,4S)-3-aminotetrahydro-2H-pyran-4-ol (0.04 g) and anhydrous magnesium sulfate (0.07 g), and the mixture was stirred at room temperature for 5 hr. The insoluble substance was removed by filtration, and the filtrate was concentrated. The residue was diluted with methanol (1.90 mL)-THF (1.90 mL), sodium triacetoxyborohydride (0.13 g) was added thereto, and the mixture was stirred at room temperature for 2.5 days. The reaction mixture was diluted with ethyl acetate, and the mixture was washed with water and saturated brine. The organic layer was concentrated under reduced pressure, and the residue was purified by silica gel column chromatography (ethyl acetate/hexane) to give the title compound (0.04 g).

$^1$H NMR (300 MHz, DMSO-d$_6$) δ 1.48-1.64 (1H, m), 1.94 (1H, d, J=14.7 Hz), 2.19 (3H, s), 2.21 (3H, s), 3.35-3.44 (2H, m), 3.65-3.74 (4H, m), 3.82-3.95 (3H, m), 4.00 (2H, s), 4.34-4.49 (2H, m), 5.04 (1H, d, J=5.3 Hz), 6.84 (2H, d, J=8.7 Hz), 7.03 (2H, d, J=8.3 Hz), 7.28 (1H, s).

Example 19

1,5-anhydro-2,4-dideoxy-2-(6-(3-fluoro-4-(methylcarbamoyl)benzyl)-4,5-dimethyl-1-oxo-1,3-dihydro-2H-isoindol-2-yl)-L-threo-pentitol

A) 2-fluoro-N-methyl-4-vinylbenzamide

A mixture of 4-bromo-2-fluoro-N-methylbenzamide (0.80 g), vinylboronic acid pinacol cyclic ester (0.80 g) and 2M aqueous sodium carbonate solution (3.45 mL) in DME (17.3 mL) was argon-purged. Bis(triphenylphosphine)palladium (II) dichloride (0.12 g) was added thereto, and the mixture was stirred overnight at 80° C. The reaction solution was diluted with ethyl acetate, and the mixture was washed with water and saturated brine. The organic layer was dried over anhydrous magnesium sulfate, and the solvent was evaporated under reduced pressure. The residue was subjected to short silica gel column chromatography, and the solvent was evaporated under reduced pressure to give the title compound (0.74 g).

MS: [M+H]$^+$ 180.1.

B) 2-fluoro-4-formyl-N-methylbenzamide

To a solution of 2-fluoro-N-methyl-4-vinylbenzamide (0.62 g) in a mixed solvent of acetone (23 mL)-acetonitrile (23 mL)-water (23 mL) were added osmium oxide (fixed catalyst I) (0.44 g) and sodium periodate (3.69 g), and the mixture was stirred overnight at room temperature. The insoluble substance was removed by filtration, and the filtrate was diluted with ethyl acetate and water. The insoluble substance was removed by filtration, the filtrate was concentrated under reduced pressure, and the residue was diluted with ethyl acetate. The mixture was washed with water and saturated brine, the organic layer was dried over anhydrous magnesium sulfate, and the solvent was evaporated under reduced pressure. The residue was subjected to short silica gel column chromatography, and the solvent was evaporated under reduced pressure to give the title compound (0.62 g).

MS: [M+H]$^+$ 182.1.

C) 2-fluoro-4-(hydroxymethyl)-N-methylbenzamide

To a solution of 2-fluoro-4-formyl-N-methylbenzamide (0.62 g) in methanol (17 mL) was added sodium borohydride (0.16 g) in small portions, and the mixture was stirred at room temperature for 3 days. To the reaction mixture was added aqueous ammonium chloride, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.44 g).

MS: [M+H]$^+$ 184.1.

D) 4-(chloromethyl)-2-fluoro-N-methylbenzamide

To a solution of 2-fluoro-4-(hydroxymethyl)-N-methylbenzamide (2.11 g) in THF (46.1 mL) was added dropwise thionyl chloride (1.01 mL) under ice-cooling, and the mixture was stirred overnight at room temperature. To the reaction solution was added saturated aqueous sodium bicarbonate, and the mixture was extracted with ethyl acetate. The organic layer was washed with saturated brine, and dried over anhydrous magnesium sulfate, and the solvent was evaporated under reduced pressure. The residue was subjected to silica gel column chromatography (ethyl acetate/hexane). The objective fractions were collected, and washed with diisopropyl ether, and the precipitate was collected by filtration. The filtrate was concentrated, and the residue was washed with diisopropyl ether. This procedure was repeated three times to give the title compound (0.96 g).

MS: [M+H]$^+$ 202.1.

E) methyl 5-(3-fluoro-4-(methylcarbamoyl)benzyl)-2-hydroxy-3,4-dimethylbenzoate

To a mixture of methyl 2-hydroxy-3,4-dimethyl-5-(4,4,5,5-tetramethyl-1,3,2-dioxaborolan-2-yl)benzoate (0.35 g), 4-(chloromethyl)-2-fluoro-N-methylbenzamide (0.23 g) and sodium carbonate (0.24 g) in 1,2-dimethoxyethane (5.40 mL)-water (1.80 mL) was added tetrakis(triphenylphosphine)palladium(0) (0.07 g), and the mixture was stirred overnight at 80° C. under argon atmosphere. To the reaction mixture were added water and ethyl acetate, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.37 g).

MS: [M+H]$^+$ 346.2.

F) methyl 5-(3-fluoro-4-(methylcarbamoyl)benzyl)-3,4-dimethyl-2-(((trifluoromethyl)sulfonyl)oxy)benzoate To a solution of methyl 5-(3-fluoro-4-(methylcarbamoyl)benzyl)-2-hydroxy-3,4-dimethylbenzoate (0.36 g) in DMF (7.00 mL) were added sodium hydride (0.05 g) and N-phenylbis(trifluoromethanesulfonimide)(0.41 g) under ice-cooling, and the mixture was stirred for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.29 g).

MS: [M+H]$^+$ 478.0.

G) methyl 5-(3-fluoro-4-(methylcarbamoyl)benzyl)-3,4-dimethyl-2-vinylbenzoate

To a solution of methyl 5-(3-fluoro-4-(methylcarbamoyl)benzyl)-3,4-dimethyl-2-(((trifluoromethyl)sulfonyl)oxy)benzoate (0.28 g) in DMF (6.00 mL) were added tributylvinyltin (0.29 g), trans-dichlorobis(triphenylphosphine)palladium(II) (0.02 g) and lithium chloride (0.19 g), and the mixture was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.19 g).

MS: [M+H]$^+$ 356.1.

H) methyl 5-(3-fluoro-4-(methylcarbamoyl)benzyl)-2-formyl-3,4-dimethylbenzoate

To a solution of methyl 5-(3-fluoro-4-(methylcarbamoyl)benzyl)-3,4-dimethyl-2-vinylbenzoate (0.19 g) in a mixed solvent of acetone (2.20 mL)-acetonitrile (2.20 mL)-water (2.20 mL) were added osmium oxide (fixed catalyst I) (0.07 g) and sodium periodate (0.56 g), and the mixture was stirred overnight at room temperature. The reaction mixture was filtered, and the filtrate was extracted with ethyl acetate. The organic layer was washed with water and saturated brine, and dried over anhydrous magnesium sulfate, and the solvent was evaporated under reduced pressure to give the title compound (0.19 g) as a crude product. This compound was used in the next step without an additional purification.
MS: [M+H]+ 358.2.

I) 1,5-anhydro-2,4-dideoxy-2-(6-(3-fluoro-4-(methylcarbamoyl)benzyl)-4,5-dimethyl-1-oxo-1,3-dihydro-2H-isoindol-2-yl)-L-threo-pentitol To a solution of methyl 5-(3-fluoro-4-(methylcarbamoyl)benzyl)-2-formyl-3,4-dimethylbenzoate (0.09 g) in THF (2.00 mL) were added (3S,4S)-3-aminotetrahydro-2H-pyran-4-ol (0.03 g) and anhydrous magnesium sulfate (0.06 g), and the mixture was stirred at room temperature for 5 hr. The reaction mixture was concentrated, and the residue was diluted with methanol (2.00 mL)-THF (2.00 mL). Sodium triacetoxyborohydride (0.11 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (methanol/ethyl acetate) to give the title compound (0.04 g).
$^1$H NMR (300 MHz, DMSO-$d_6$) δ 1.47-1.63 (1H, m), 1.89-1.99 (1H, m), 2.18 (3H, s), 2.22 (3H, s), 2.75 (3H, d, J=4.5 Hz), 3.40 (2H, d, J=10.5 Hz), 3.70 (1H, dd, J=10.9, 3.4 Hz), 3.81-3.97 (3H, m), 4.14 (2H, s), 4.35-4.51 (2H, m), 5.05 (1H, d, J=5.3 Hz), 6.96-7.05 (2H, m), 7.36 (1H, s), 7.54 (1H, t, J=7.9 Hz), 8.14 (1H, brs).

Example 20-1

4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one Alias; 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol A) 3-fluoro-2-hydroxy-4-methylbenzoic acid To an aqueous solution (50.0 mL) of sodium chlorite (22.2 g) was added a mixture of 3-fluoro-2-hydroxy-4-methylbenzaldehyde (9.47 g), sodium dihydrogenphosphate (33.2 g) and 2-methyl-2-butene (32.5 mL) in tert-butanol (200 mL)-water (100 mL) under ice-cooling, and the mixture was stirred at the same temperature for 3 hr. The pH of the reaction mixture was adjusted to 2-3 with 2N hydrochloric acid. To the reaction mixture was added water, and the mixture was extracted with ethyl acetate. The organic layer was washed with water and saturated brine, and dried over anhydrous magnesium sulfate, and the solvent was evaporated under reduced pressure to give the title compound (10.5 g) as a crude product. This compound was used in the next step without an additional purification.

B) methyl 3-fluoro-2-hydroxy-4-methylbenzoate

To a solution of 3-fluoro-2-hydroxy-4-methylbenzoic acid (10.5 g) in methanol (50.0 mL) was added sulfuric acid (5.00 mL) at room temperature, and the mixture was stirred at 60° C. for 24 hr. The solvent was evaporated under reduced pressure, to the residue were added water and ethyl acetate, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (6.40 g).
MS: [M+H]+ 185.0.

C) methyl 5-bromo-3-fluoro-2-hydroxy-4-methylbenzoate

To a solution of methyl 3-fluoro-2-hydroxy-4-methylbenzoate (6.40 g) in acetic acid (120 mL) was added bromine (1.87 mL) at room temperature, and the mixture was stirred at the same temperature for 2 hr. To the reaction mixture was added 10% aqueous sodium thiosulfate solution, and the mixture was extracted with ethyl acetate. The organic layer was washed with water and saturated brine, and dried over anhydrous magnesium sulfate, and the solvent was evaporated under reduced pressure to give a mixture (7.99 g) of the title compound and the raw material (about 2:1). The obtained product was used in the next step without an additional purification.
$^1$H NMR (300 MHz, CDCl$_3$) δ 2.38 (3H, d, J=2.8 Hz), 3.98 (3H, s), 7.82 (1H, d, J=2.1 Hz), 10.67 (1H, s).

D) methyl 3-fluoro-2-hydroxy-4-methyl-5-(4,4,5,5-tetramethyl-1,3,2-dioxaborolan-2-yl)benzoate trans-Dichlorobis(triphenylphosphine)palladium (II) (1.07 g) was added to a mixture of the 2:1 mixture (7.99 g) of methyl 5-bromo-3-fluoro-2-hydroxy-4-methylbenzoate and methyl 3-fluoro-2-hydroxy-4-methylbenzoate, bis(pinacolato)diboron (11.6 g), potassium acetate (8.94 g) and toluene (160 mL) at room temperature under argon atmosphere, and the mixture was stirred at 100° C. for 2 hr. To the reaction mixture was again added trans-dichlorobis(triphenylphosphine)palladium(II) (1.07 g), and the mixture was stirred at 100° C. for 3 days. To the reaction mixture was again added trans-dichlorobis(triphenylphosphine)palladium(II) (1.07 g), and the mixture was stirred overnight at 100° C. The reaction mixture was allowed to be cooled to room temperature, water was added thereto, and the precipitate was removed by filtration. The filtrate was extracted with ethyl acetate, the organic layer was washed with water and saturated brine, and dried over anhydrous magnesium sulfate, and the solvent was evaporated under reduced pressure. The residue was purified by silica gel column chromatography (ethyl acetate/hexane) to give the title compound (2.20 g). In addition, the title compound (4.03 g) was obtained from second fraction of column chromatography.
MS: [M+H]+ 311.1.

E) methyl 5-(4-(1H-pyrazol-1-yl)benzyl)-3-fluoro-2-hydroxy-4-methylbenzoate

Tetrakis(triphenylphosphine)palladium(0) (0.40 g) was added to a mixture of methyl 3-fluoro-2-hydroxy-4-methyl-5-(4,4,5,5-tetramethyl-1,3,2-dioxaborolan-2-yl)benzoate (2.13 g), 1-(4-(chloromethyl)phenyl)-1H-pyrazole (1.32 g), sodium carbonate (1.46 g), DME (30.0 mL) and water (10.0 mL) under argon atmosphere, and the mixture was stirred overnight at 80° C. The reaction mixture was allowed to be cooled to room temperature, water was added thereto, and the mixture was extracted with ethyl acetate. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.33 g).
MS: [M+H]+ 341.1.

F) methyl 5-(4-(1H-pyrazol-1-yl)benzyl)-3-fluoro-4-methyl-2-(((trifluoromethyl)sulfonyl)oxy)benzoate To a solution of methyl 5-(4-(1H-pyrazol-1-yl)benzyl)-3-fluoro-2-hydroxy-4-methylbenzoate (0.33 g) in DMF (7.0 mL) were added sodium hydride (0.047 g) and N-phenylbis(trifluoromethanesulfonimide)(0.38 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.36 g).
MS: [M+H]$^+$ 473.1.

G) methyl 5-(4-(1H-pyrazol-1-yl)benzyl)-3-fluoro-4-methyl-2-vinylbenzoate

A mixture of methyl 5-(4-(1H-pyrazol-1-yl)benzyl)-3-fluoro-4-methyl-2-(((trifluoromethyl)sulfonyl)oxy)benzoate (0.36 g), tributylvinyltin (0.33 mL), trans-dichlorobis(triphenylphosphine)palladium(II) (0.03 g), lithium chloride (0.24 g) and DMF (7.2 mL) was stirred at 90° C. for 1 hr under argon atmosphere. To the reaction mixture was added aqueous potassium fluoride solution, and the insoluble substance was removed by filtration through Celite. The filtrate was diluted with ethyl acetate, and the mixture was washed with saturated brine. The organic layer was dried over anhydrous magnesium sulfate, and the solvent was evaporated under reduced pressure. The residue was purified by silica gel column chromatography (ethyl acetate/hexane) to give the title compound (0.21 g).
MS: [M+H]$^+$ 351.2.

H) methyl 5-(4-(1H-pyrazol-1-yl)benzyl)-3-fluoro-2-formyl-4-methylbenzoate

To a mixture of methyl 5-(4-(1H-pyrazol-1-yl)benzyl)-3-fluoro-4-methyl-2-vinylbenzoate (0.21 g), acetone (2.3 mL), acetonitrile (2.3 mL) and water (2.3 mL) were added osmium oxide (fixed catalyst I) (0.08 g) and sodium periodate (0.63 g) at room temperature, and the mixture was stirred overnight at the same temperature. The insoluble substance was removed by filtration, and the filtrate was diluted with ethyl acetate. The solution was washed with saturated brine, and dried over anhydrous magnesium sulfate, and the solvent was evaporated under reduced pressure to give the title compound (0.21 g) as a crude product. This compound was used in the next step without an additional purification.
MS: [M+H]$^+$ 353.1.

I) 4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one Alias; 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol A mixture of methyl 5-(4-(1H-pyrazol-1-yl)benzyl)-3-fluoro-2-formyl-4-methylbenzoate (0.21 g), (3S,4S)-3-aminotetrahydro-2H-pyran-4-ol (0.07 g), anhydrous magnesium sulfate (0.14 g) and THF (4.00 mL) was stirred at room temperature for 6 hr under nitrogen atmosphere. The insoluble substance was removed by filtration, and the filtrate was concentrated. The residue was dissolved in a mixed solvent of methanol (4.00 mL)-THF (4.00 mL), sodium triacetoxyborohydride (0.25 g) was added thereto, and the mixture was stirred at room temperature for 16 hr. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.11 g).
$^1$H NMR (300 MHz, DMSO-d$_6$) δ 1.45-1.64 (1H, m), 1.88-1.99 (1H, m), 2.23 (3H, d, J=2.1 Hz), 3.33-3.47 (2H, m), 3.64-3.95 (4H, m), 4.15 (2H, s), 4.55 (2H, s), 5.08 (1H, d, J=5.1 Hz), 6.49-6.56 (1H, m), 7.27 (2H, d, J=8.7 Hz), 7.38 (1H, s), 7.68-7.81 (3H, m), 8.44 (1H, d, J=2.1 Hz).

Example 20-2

4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one Alias; 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol This compound was also synthesized by the following method.

A) 3-fluoro-2-hydroxy-4-methylbenzoic acid

A mixture of 2,3-difluoro-4-methylbenzoic acid (25.0 g), sodium hydroxide (23.2 g) and DMSO (250 mL) was stirred at 140° C. for 12 hr, and then overnight at room temperature, under argon atmosphere. To the reaction mixture was added 6M hydrochloric acid (100 mL) under ice-cooling. Ethyl acetate and water were added thereto at room temperature, the organic layer was separated, and the aqueous layer was extracted with ethyl acetate. The organic layers were combined, washed with water and saturated brine, and dried over anhydrous magnesium sulfate, and the solvent was evaporated under reduced pressure to give the title compound (24.3 g). This compound was used in the next step without an additional purification.
$^1$H NMR (300 MHz, CDCl$_3$) δ 2.35 (3H, d, J=2.3 Hz), 6.74 (1H, dd, J=7.9, 6.8 Hz), 7.58 (1H, dd, J=8.3, 1.5 Hz), 10.37 (1H, s), 1H undetected.

B) methyl 3-fluoro-2-hydroxy-4-methylbenzoate

To a solution of 3-fluoro-2-hydroxy-4-methylbenzoic acid (24.3 g) in methanol (500 mL) was added sulfuric acid (7.60 mL) at room temperature, and the mixture was stirred at 60° C. for 3 days. The solvent was evaporated under reduced pressure, and ethyl acetate and saturated brine were added thereto. The organic layer was separated, and the aqueous layer was extracted with ethyl acetate. The combined organic layers were washed with water and saturated brine, and dried over anhydrous magnesium sulfate, and the solvent was evaporated under reduced pressure. To the residue was added diisopropyl ether (50 mL), and the insoluble substance was removed by filtration. The filtrate was concentrated under reduced pressure to give the title compound (25.4 g).

¹H NMR (300 MHz, CDCl₃) δ 2.32 (3H, d, J=2.5 Hz), 3.95 (3H, s), 6.68 (1H, dd, J=7.9, 6.8 Hz), 7.49 (1H, dd, J=8.3, 1.7 Hz), 10.74 (1H, s).

C) methyl 5-bromo-3-fluoro-2-hydroxy-4-methylbenzoate

To a solution of methyl 3-fluoro-2-hydroxy-4-methylbenzoate (25.4 g) in acetic acid (250 mL) was added bromine (7.78 mL), and the mixture was stirred at room temperature for 3 hr. To the reaction mixture was added 5% aqueous sodium thiosulfate solution (250 mL) at room temperature, and the precipitate was collected by filtration, and washed with water to give the title compound (21.1 g).
¹H NMR (300 MHz, CDCl₃) δ 2.37 (3H, d, J=2.6 Hz), 3.97 (3H, s), 7.81 (1H, d, J=1.7 Hz), 10.65 (1H, s).

D) methyl 3-fluoro-2-hydroxy-4-methyl-5-(4,4,5,5-tetramethyl-1,3,2-dioxaborolan-2-yl)benzoate trans-Dichlorobis(triphenylphosphine)palladium(II) (2.0 g) was added to a mixture of methyl 5-bromo-3-fluoro-2-hydroxy-4-methylbenzoate (15.0 g), bis(pinacolato)diboron (21.7 g), potassium acetate (16.8 g) and toluene (290 mL) under argon atmosphere, and the mixture was stirred at 110° C. for 15 hr. To the reaction mixture was added water, and the mixture was extracted with ethyl acetate. The organic layer was washed with water and saturated brine, and dried over anhydrous magnesium sulfate, and the solvent was evaporated under reduced pressure. The residue was washed with diisopropyl ether to give the title compound (12.3 g). The filtrate was purified by silica gel column chromatography (ethyl acetate/hexane) to give the title compound (1.99 g).
MS: [M+H]⁺ 311.2.

E) methyl 5-(4-(1H-pyrazol-1-yl)benzyl)-3-fluoro-2-hydroxy-4-methylbenzoate

Tetrakis(triphenylphosphine)palladium(0) (2.52 g) was added to a mixture of methyl 3-fluoro-2-hydroxy-4-methyl-5-(4,4,5,5-tetramethyl-1,3,2-dioxaborolan-2-yl)benzoate (13.5 g), 1-(4-(chloromethyl)phenyl)-1H-pyrazole (8.39 g), sodium carbonate (9.23 g), DME (195 mL) and water (65.0 mL) under argon atmosphere, and the mixture was stirred overnight at 80° C. To the reaction mixture was added water, and the mixture was extracted with ethyl acetate. The organic layer was washed with saturated brine, and dried over anhydrous magnesium sulfate, and the solvent was evaporated under reduced pressure. The residue was washed with a mixed solvent of diisopropyl ether-ethyl acetate to give a crude product. The filtrate was concentrated under reduced pressure, and the residue was purified by silica gel column chromatography (ethyl acetate/methanol). The obtained crude products are combined, and washed with diisopropyl ether-ethyl acetate to give the title compound (12.4 g).
MS: [M+H]⁺ 341.1.

F) methyl 5-(4-(1H-pyrazol-1-yl)benzyl)-3-fluoro-4-methyl-2-(((trifluoromethyl)sulfonyl)oxy)benzoate To a solution of methyl 5-(4-(1H-pyrazol-1-yl)benzyl)-3-fluoro-2-hydroxy-4-methylbenzoate (12.4 g) in DMF (250 mL) were added sodium hydride (1.74 g) and N-phenylbis(trifluoromethanesulfonimide) (14.3 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (12.5 g).
MS: [M+H]⁺ 473.1.

G) methyl 5-(4-(1H-pyrazol-1-yl)benzyl)-3-fluoro-4-methyl-2-vinylbenzoate

A mixture of methyl 5-(4-(1H-pyrazol-1-yl)benzyl)-3-fluoro-4-methyl-2-(((trifluoromethyl)sulfonyl)oxy)benzoate (11.8 g), tributylvinyltin (11.9 g), trans-dichlorobis(triphenylphosphine)palladium(II) (0.88 g), lithium chloride (7.84 g) and DMF (240 mL) was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with saturated brine. The organic layer was dried over anhydrous magnesium sulfate, and the solvent was evaporated under reduced pressure. The residue was purified by silica gel column chromatography (ethyl acetate/hexane) to give the title compound (7.98 g).
MS: [M+H]⁺ 351.2.

H) methyl 5-(4-(1H-pyrazol-1-yl)benzyl)-3-fluoro-2-formyl-4-methylbenzoate

To a mixture of methyl 5-(4-(1H-pyrazol-1-yl)benzyl)-3-fluoro-4-methyl-2-vinylbenzoate (7.97 g), acetone (93.0 mL), acetonitrile (93.0 mL) and water (93.0 mL) were added osmium oxide (fixed catalyst I) (2.89 g) and sodium periodate (24.3 g) at room temperature, and the mixture was stirred overnight at the same temperature. The insoluble substance was removed by filtration, and the filtrate was diluted with ethyl acetate. The solution was washed with saturated brine, the organic layer was and dried over anhydrous magnesium sulfate, and the solvent was evaporated under reduced pressure to give the title compound (7.97 g) as a crude product. This compound was used in the next step without an additional purification.
MS: [M+H]⁺ 353.2.

I) 4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one Alias; 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-pentitol A mixture of methyl 5-(4-(1H-pyrazol-1-yl)benzyl)-3-fluoro-2-formyl-4-methylbenzoate (7.97 g), (3S,4S)-3-aminotetrahydro-2H-pyran-4-ol (2.65 g), anhydrous magnesium sulfate (5.23 g) and THF (160 mL) was stirred at room temperature for 5 hr under nitrogen atmosphere. The insoluble substance was removed by filtration, and the filtrate was concentrated. The residue was dissolved in a mixed solvent of methanol (120 mL)-THF (150 mL), sodium triacetoxyborohydride (9.59 g) was added thereto, and the mixture was stirred at room temperature for 15 hr. Sodium triacetoxyborohydride (9.59 g) was again added thereto, and the mixture was stirred for 3 hr. The reaction mixture was diluted with ethyl acetate, and the mixture was washed with water and saturated brine. The organic layer was dried over anhydrous magnesium sulfate, and the solvent was evaporated under reduced pressure. The residue was dissolved in DMSO-toluene, and the solution was purified by NH silica gel column chromatography (ethyl acetate/hexane). The obtained crude product was dissolved in THF, the solution was washed with water and saturated brine, and the solvent was evaporated under reduced pressure. The residue was washed with a mixed solvent of diisopropyl ether-ethyl acetate to give a crude product. The crude product (5.28 g) was dissolved in hot ethanol (60 mL), and recrystallized over 4 hr under ice-cooling to give the title compound (4.88 g).

$^1$H NMR (300 MHz, CDCl$_3$) δ 1.71-1.87 (1H, m), 2.08-2.17 (1H, m), 2.22 (3H, d, J=2.3 Hz), 2.47-2.57 (1H, m), 3.42-3.62 (2H, m), 3.97-4.15 (6H, m), 4.31-4.63 (2H, m), 6.39-6.50 (1H, m), 7.17 (2H, d, J=8.7 Hz), 7.47 (1H, s), 7.59 (2H, d, J=8.7 Hz), 7.70 (1H, d, J=1.5 Hz), 0.7.88 (1H, d, J=2.3 Hz).

X-ray powder diffraction pattern with specific peaks at d value (or d-spacing)=12.8, 8.0, 7.5, 6.2, 6.0, 5.6, 5.0, 4.6, 4.5 and 4.2 Å.

Example 21

1,5-anhydro-2,4-dideoxy-2-(5-methyl-1-oxo-6-(4-(H-pyrazol-1-yl)benzyl)-1,3-dihydro-2H-isoindol-2-yl)-L-threo-pentitol To a solution of methyl 5-(4-(1H-pyrazol-1-yl)benzyl)-2-formyl-4-methylbenzoate (0.20 g) in THF (4.00 mL) was added (3S,4S)-3-aminotetrahydro-2H-pyran-4-ol (0.07 g), and the mixture was stirred at room temperature for 4 hr under argon atmosphere. The reaction mixture was concentrated, and the residue was diluted with acetic acid (4.00 mL). Sodium triacetoxyborohydride (0.19 g) was added thereto, and the mixture was stirred overnight at room temperature. The reaction mixture was diluted with saturated aqueous sodium bicarbonate solution and extracted with ethyl acetate, the organic layer was washed with water and saturated brine, and dried over anhydrous magnesium sulfate, and the solvent was evaporated under reduced pressure. The residue was purified by NH silica gel column chromatography (ethyl acetate/hexane) to give the title compound (0.11 g).

$^1$H NMR (300 MHz, CDCl$_3$) δ 1.71-1.90 (1H, m), 2.07-2.18 (1H, m), 2.31 (3H, s), 2.69 (1H, d, J=5.5 Hz), 3.43-3.59 (2H, m), 3.98-4.15 (6H, m), 4.29-4.55 (2H, m), 6.45 (1H, t, J=2.1 Hz), 7.18 (2H, d, J=8.5 Hz), 7.24 (1H, s), 7.55-7.61 (2H, m), 7.63 (1H, s), 7.70 (1H, d, J=1.7 Hz), 7.88 (1H, d, J=2.5 Hz).

Example 22

1,5-anhydro-2,4-dideoxy-2-(6-(4-(difluoromethoxy)benzyl)-4,5-dimethyl-1-oxo-1,3-dihydro-2H-isoindol-2-yl)-L-threo-pentitol A) methyl 5-(4-(difluoromethoxy)benzyl)-2-hydroxy-3,4-dimethylbenzoate To a solution of methyl 2-hydroxy-3,4-dimethyl-5-(4,4,5,5-tetramethyl-1,3,2-dioxaborolan-2-yl)benzoate (0.60 g) in DME (12.0 mL) were added 1-(bromomethyl)-4-(difluoromethoxy)benzene (0.47 g), [1,1'-bis(diphenylphosphino)ferrocene]dichloropalladium(II)dichloromethane adduct (0.16 g) and 2 mol/L aqueous sodium carbonate solution (1.96 mL), and the mixture was stirred overnight at 80° C. under argon atmosphere. Water and ethyl acetate were added thereto, the mixture was allowed to be cooled to room temperature, and the precipitate was removed by filtration. The filtrate was extracted with ethyl acetate, the organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.60 g).

MS: [M+H]$^+$ 337.0.

B) methyl 5-(4-(difluoromethoxy)benzyl)-3,4-dimethyl-2-vinylbenzoate

To a solution of methyl 5-(4-(difluoromethoxy)benzyl)-2-hydroxy-3,4-dimethylbenzoate (0.60 g) in DMF (12.0 mL) was added sodium hydride (0.08 g) under ice-cooling, and the mixture was stirred at room temperature for 30 min. To this reaction mixture was added N-phenylbis(trifluoromethanesulfonimide) (0.77 g) under ice-cooling, and the mixture was stirred at room temperature for 1 hr. To the reaction mixture was added 1N hydrochloric acid under ice-cooling, and the mixture was extracted with ethyl acetate. The organic layer was washed with water and saturated brine, and dried over anhydrous magnesium sulfate, and the solvent was evaporated under reduced pressure. The obtained crude methyl 5-[4-(difluoromethoxy)benzyl]-3,4-dimethyl-2-{[(trifluoromethyl)sulfonyl]oxy}benzoate was used in the next step without an additional purification.

The above-mentioned compound was dissolved in DMF (12.0 mL), tributylvinyltin (0.78 mL), trans-dichlorobis(triphenylphosphine)palladium(II) (0.13 g) and lithium chloride (0.53 g) were added thereto, and the mixture was stirred overnight at 90° C. under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.16 g).

MS: [M+H]$^+$ 347.2.

C) methyl 5-(4-(difluoromethoxy)benzyl)-2-formyl-3,4-dimethylbenzoate

To a solution of methyl 5-(4-(difluoromethoxy)benzyl)-3,4-dimethyl-2-vinylbenzoate (0.16 g) in a mixed solvent of acetone (3.00 mL)-acetonitrile (3.00 mL)-water (3.00 mL) were added osmium oxide (fixed catalyst I) (0.06 g) and sodium periodate (0.49 g), and the mixture was stirred overnight at room temperature. The reaction mixture was filtered, and the filtrate was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (0.04 g).

MS: [M+H]$^+$ 349.1.

D) 1,5-anhydro-2,4-dideoxy-2-(6-(4-(difluoromethoxy)benzyl)-4,5-dimethyl-1-oxo-1,3-dihydro-2H-isoindol-2-yl)-L-threo-pentitol To a solution of methyl 5-(4-(difluoromethoxy)benzyl)-2-formyl-3,4-dimethylbenzoate (0.04 g) in THF (2.00 mL)

was added (3S,4S)-3-aminotetrahydro-2H-pyran-4-ol (0.01 g) under argon atmosphere, and the mixture was stirred at room temperature for 3 hr. The reaction mixture was concentrated, and the residue was diluted with acetic acid (2.00 mL). Sodium triacetoxyborohydride (0.03 g) was added thereto under argon atmosphere, and the mixture was stirred overnight at room temperature. The reaction mixture was diluted with saturated aqueous sodium bicarbonate solution, and extracted with ethyl acetate. The organic layer was washed with water and saturated brine, and dried over anhydrous magnesium sulfate, and the solvent was evaporated under reduced pressure. The residue was purified by NH silica gel column chromatography (ethyl acetate/hexane) to give the title compound (0.02 g).

$^1$H NMR (300 MHz, CDCl$_3$) δ 1.73-1.88 (1H, m), 2.09-2.18 (1H, m), 2.21 (3H, s), 2.25 (3H, s), 2.52 (1H, d, J=5.3 Hz), 3.45-3.63 (2H, m), 4.00-4.18 (6H, m), 4.26-4.50 (2H, m), 6.19-6.75 (1H, m), 6.99-7.04 (2H, m), 7.06-7.11 (2H, m), 7.51 (1H, s).

Example 23

1,5-anhydro-2,4-dideoxy-2-(6-(4-fluoro-3-methoxybenzyl)-4,5-dimethyl-1-oxo-1,3-dihydro-2H-isoindol-2-yl)-L-threo-pentitol A) methyl 5-(4-fluoro-3-methoxybenzyl)-2-hydroxy-3,4-dimethylbenzoate To a solution of methyl 2-hydroxy-3,4-dimethyl-5-(4,4,5,5-tetramethyl-1,3,2-dioxaborolan-2-yl)benzoate (0.50 g) in DME (12.0 mL) were added 4-(bromomethyl)-1-fluoro-2-methoxybenzene (0.39 g), [1,1'-bis(diphenylphosphino)ferrocene]dichloropalladium(II)dichloromethane adduct (0.07 g) and 2 mol/L aqueous sodium carbonate solution (1.63 mL), and the mixture was stirred overnight at 80° C. under argon atmosphere. The reaction mixture was allowed to be cooled to room temperature, and diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (0.45 g).

$^1$H NMR (300 MHz, DMSO-d$_6$) δ 2.13 (6H, s), 3.78 (3H, s), 3.88 (3H, s), 3.94 (2H, s), 6.53 (1H, ddd, J=8.3, 4.4, 2.1 Hz), 6.97 (1H, dd, J=8.5, 1.9 Hz), 7.07 (1H, dd, J=11.5, 8.3 Hz), 7.49 (1H, s), 10.90 (1H, s).

B) methyl 5-(4-fluoro-3-methoxybenzyl)-3,4-dimethyl-2-(((trifluoromethyl)sulfonyl)oxy)benzoate To a solution of methyl 5-(4-fluoro-3-methoxybenzyl)-2-hydroxy-3,4-dimethylbenzoate (0.45 g) in DMF (5.0 mL) were added sodium hydride (0.07 g) and N-phenylbis(trifluoromethanesulfonimide) (0.55 g) under ice-cooling, and the mixture was stirred at room temperature for 2 hr under argon atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (0.63 g).

$^1$H NMR (300 MHz, DMSO-d$_6$) δ 2.19-2.32 (6H, m), 3.76-3.85 (6H, m), 4.08 (2H, s), 6.59 (1H, ddd, J=8.3, 4.3, 2.1 Hz), 6.99-7.16 (2H, m), 7.61 (1H, s).

C) methyl 5-(4-fluoro-3-methoxybenzyl)-3,4-dimethyl-2-vinylbenzoate

To a solution of methyl 5-(4-fluoro-3-methoxybenzyl)-3,4-dimethyl-2-(((trifluoromethyl)sulfonyl)oxy)benzoate (0.63 g) in DMF (7.00 mL) were added tributylvinyltin (0.61 mL), trans-dichlorobis(triphenylphosphine)palladium(II) (0.05 g) and lithium chloride (0.44 g), and the mixture was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with saturated brine. The organic layer was dried over anhydrous magnesium sulfate, and the solvent was evaporated under reduced pressure. The residue was purified by silica gel column chromatography (ethyl acetate/hexane) to give the title compound (0.39 g).

MS: [M+H]$^+$ 329.1.

D) methyl 5-(4-fluoro-3-methoxybenzyl)-2-formyl-3,4-dimethylbenzoate

To a solution of methyl 5-(4-fluoro-3-methoxybenzyl)-3,4-dimethyl-2-vinylbenzoate (0.39 g) in a mixed solvent of acetone (9.00 mL)-acetonitrile (9.00 mL)-water (9.00 mL) were added osmium oxide (fixed catalyst I) (0.15 g) and sodium periodate (1.27 g), and the mixture was stirred at room temperature for 2.5 days. The reaction mixture was filtered, and the filtrate was extracted with ethyl acetate. The organic layer was washed with saturated brine, and dried over anhydrous magnesium sulfate to give the title compound (0.39 g). This compound was used in the next step without an additional purification.

MS: [M+H]$^+$ 331.1.

E) 1,5-anhydro-2,4-dideoxy-2-(6-(4-fluoro-3-methoxybenzyl)-4,5-dimethyl-1-oxo-1,3-dihydro-2H-isoindol-2-yl)-L-threo-pentitol To a solution of methyl 5-(4-fluoro-3-methoxybenzyl)-2-formyl-3,4-dimethylbenzoate (0.35 g) in THF (4.00 mL) were added (3S,4S)-3-aminotetrahydro-2H-pyran-4-ol (0.12 g) and anhydrous magnesium sulfate (0.26 g), and the mixture was stirred at room temperature for 5 hr under nitrogen atmosphere. The insoluble substance was removed by filtration, the filtrate was concentrated, and the residue was diluted with methanol (2.00 mL)-THF (4.00 mL). Sodium triacetoxyborohydride (0.45 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.13 g).

$^1$H NMR (300 MHz, DMSO-d$_6$) δ 1.47-1.66 (1H, m), 1.89-2.00 (1H, m), 2.18-2.26 (6H, m), 3.34-3.45 (2H, m), 3.69 (1H, dd, J=10.9, 3.4 Hz), 3.78 (3H, s), 3.82-3.96 (3H, m), 4.05 (2H, s), 4.34-4.50 (2H, m), 5.05 (1H, d, J=4.5 Hz), 6.49-6.61 (1H, m), 6.97-7.13 (2H, m), 7.30 (1H, s).

Example 24

1,5-anhydro-2-(4-chloro-6-(4-methoxybenzyl)-5-methyl-1-oxo-1,3-dihydro-2H-isoindol-2-yl)-2,4-dideoxy-L-threo-pentitol

A) methyl 5-bromo-3-chloro-2-hydroxy-4-methylbenzoate

To a solution of methyl 5-bromo-2-hydroxy-4-methylbenzoate (4.54 g) in DMF (34.0 mL) was added N-chlorosuccinimide (2.47 g), and the mixture was stirred overnight at room temperature. To the reaction mixture was added water, and the mixture was extracted with ethyl acetate. The organic layer was washed with water and saturated brine, and dried over anhydrous magnesium sulfate, and the solvent was evaporated under reduced pressure to give the title compound (5.20 g).

MS: [M–H]$^+$ 276.7.

B) methyl 3-chloro-2-hydroxy-4-methyl-5-(4,4,5,5-tetramethyl-1,3,2-dioxaborolan-2-yl)benzoate To a solution of methyl 5-bromo-3-chloro-2-hydroxy-4-methylbenzoate (5.20 g) in toluene (140 mL) were added bis(pinacolato)diboron (7.09 g), potassium acetate (5.48 g) and trans-dichlorobis(triphenylphosphine)palladium(II) (0.65 g), and the mixture was stirred at 110° C. for 15 hr under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (3.54 g).

MS: [M+H]$^+$ 327.1.

C) methyl 3-chloro-2-hydroxy-5-(4-methoxybenzyl)-4-methylbenzoate

To a solution of methyl 3-chloro-2-hydroxy-4-methyl-5-(4,4,5,5-tetramethyl-1,3,2-dioxaborolan-2-yl)benzoate (0.90 g) in a mixed solvent of DME (13.5 mL)-water (4.50 mL) were added 1-(chloromethyl)-4-methoxybenzene (0.43 g), tetrakis(triphenylphosphine)palladium(0) (0.16 g) and sodium carbonate (0.58 g), and the mixture was stirred at 80° C. overnight under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.37 g).

MS: [M–H]$^+$ 318.9.

D) methyl 3-chloro-5-(4-methoxybenzyl)-4-methyl-2-(((trifluoromethyl)sulfonyl)oxy)benzoate To a solution of methyl 3-chloro-2-hydroxy-5-(4-methoxybenzyl)-4-methylbenzoate (0.36 g) in DMF (7.50 mL) were added sodium hydride (0.05 g) and N-phenylbis(trifluoromethanesulfonimide) (0.36 g) under ice-cooling, and the mixture was stirred at room temperature for 2.5 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.51 g).

MS: [M–H]$^+$ 451.8.

E) methyl 3-chloro-5-(4-methoxybenzyl)-4-methyl-2-vinylbenzoate

To a solution of methyl 3-chloro-5-(4-methoxybenzyl)-4-methyl-2-(((trifluoromethyl)sulfonyl)oxy)benzoate (0.51 g) in DMF (10.0 mL) were added tributylvinyltin (0.54 g), trans-dichlorobis(triphenylphosphine)palladium(II) (0.04 g) and lithium chloride (0.36 g), and the mixture was stirred at 90° C. for 1 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.31 g).

MS: [M+H]$^+$ 331.1.

F) methyl 3-chloro-2-formyl-5-(4-methoxybenzyl)-4-methylbenzoate

To a solution of methyl 3-chloro-5-(4-methoxybenzyl)-4-methyl-2-vinylbenzoate (0.31 g) in a mixed solvent of acetone (3.60 mL)-acetonitrile (3.60 mL)-water (3.60 mL) were added osmium oxide (fixed catalyst I) (0.12 g) and sodium periodate (1.00 g), and the mixture was stirred overnight at room temperature. The reaction mixture was filtered, and the filtrate was extracted with ethyl acetate. The organic layer was washed with water and saturated brine, and dried over anhydrous magnesium sulfate, and the solvent was evaporated under reduced pressure to give the title compound (0.31 g) as a crude product. This compound was used in the next step without an additional purification.

G) 1,5-anhydro-2-(4-chloro-6-(4-methoxybenzyl)-5-methyl-1-oxo-1,3-dihydro-2H-isoindol-2-yl)-2,4-dideoxy-L-threo-pentitol To a solution of methyl 3-chloro-2-formyl-5-(4-methoxybenzyl)-4-methylbenzoate (0.10 g) in THF (2.00 mL) were added (3S,4S)-3-aminotetrahydro-2H-pyran-4-ol (0.04 g) and anhydrous magnesium sulfate (0.07 g), and the mixture was stirred at room temperature for 6 hr. The insoluble substance was removed by filtration, the filtrate was concentrated, and the residue was diluted with methanol (2.00 mL)-THF (2.00 mL). Sodium triacetoxyborohydride (0.19 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.05 g).

$^1$H NMR (300 MHz, DMSO-d$_6$) δ 1.47-1.62 (1H, m), 1.89-1.99 (1H, m), 2.35 (3H, s), 3.34-3.48 (2H, m), 3.64-

3.74 (4H, m), 3.80-3.97 (3H, m), 4.07 (2H, s), 4.39-4.54 (2H, m), 5.11 (1H, d, J=5.3 Hz), 6.82-6.90 (2H, m), 7.05 (2H, d, J=8.7 Hz), 7.42 (1H, s).

Example 25-1

2-((1S,2S)-2-hydroxycyclohexyl)-4,5-dimethyl-6-((6-methylpyridin-3-yl)methyl)isoindolin-1-one A) 5-(chloromethyl)-2-methylpyridine To a solution of (6-methylpyridin-3-yl)methanol (1.08 g) in THF (15.0 mL) was added thionyl chloride (1.57 g) under ice-cooling, and the mixture was stirred overnight at room temperature. The reaction mixture was diluted with water and ethyl acetate, saturated aqueous sodium bicarbonate was added thereto, and the mixture was partitioned. The organic layer was washed with saturated brine, and dried over anhydrous magnesium sulfate, and the solvent was evaporated under reduced pressure. The residue was purified by silica gel column chromatography (ethyl acetate/hexane) to give the title compound (0.81 g).
$^1$H NMR (300 MHz, CDCl$_3$) δ 2.57 (3H, s), 4.57 (2H, s), 7.17 (1H, d, J=7.9 Hz), 7.63 (1H, dd, J=7.9, 2.3 Hz), 8.50 (1H, d, J=2.3 Hz).

B) methyl 2-hydroxy-3,4-dimethyl-5-((6-methylpyridin-3-yl)methyl)benzoate

To a solution of methyl 2-hydroxy-3,4-dimethyl-5-(4,4,5,5-tetramethyl-1,3,2-dioxaborolan-2-yl)benzoate (0.80 g) in a mixed solvent of DME (12.0 mL)-water (4.00 mL) were added 5-(chloromethyl)-2-methylpyridine (0.41 g), tetrakis(triphenylphosphine)palladium(0) (0.15 g) and sodium carbonate (0.55 g), and the mixture was stirred overnight at 80° C. under argon atmosphere. The reaction mixture was allowed to be cooled to room temperature, water and ethyl acetate were added thereto, and the mixture was partitioned. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.48 g).
MS: [M−H]$^+$ 286.1.

C) methyl 3,4-dimethyl-5-((6-methylpyridin-3-yl)methyl)-2-(((trifluoromethyl)sulfonyl)oxy)benzoate To a solution of methyl 2-hydroxy-3,4-dimethyl-5-((6-methylpyridin-3-yl)methyl)benzoate (0.48 g) in DMF (9.50 mL) were added sodium hydride (0.08 g) and N-phenylbis(trifluoromethanesulfonimide)(0.66 g) under ice-cooling, and the mixture was stirred at room temperature for 2.5 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.70 g).
MS: [M+H]$^+$ 418.1.

D) methyl 3,4-dimethyl-5-((6-methylpyridin-3-yl)methyl)-2-vinylbenzoate

To a solution of methyl 3,4-dimethyl-5-((6-methylpyridin-3-yl)methyl)-2-(((trifluoromethyl)sulfonyl)oxy)benzoate (0.70 g) in DMF (14.0 mL) were added tributylvinyltin (0.80 g), trans-dichlorobis(triphenylphosphine)palladium (II) (0.06 g) and lithium chloride (0.53 g), and the mixture was stirred at 90° C. for 1 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous magnesium sulfate, and the solvent was evaporated under reduced pressure. The residue was purified by silica gel column chromatography (ethyl acetate/hexane) to give the title compound (0.44 g).
MS: [M+H]$^+$ 296.1.

E) methyl 2-formyl-3,4-dimethyl-5-((6-methylpyridin-3-yl)methyl)benzoate

To a solution of methyl 3,4-dimethyl-5-((6-methylpyridin-3-yl)methyl)-2-vinylbenzoate (0.44 g) in a mixed solvent of acetone (5.40 mL)-acetonitrile (5.40 mL)-water (5.40 mL) were added osmium oxide (fixed catalyst I) (0.19 g) and sodium periodate (1.59 g), and the mixture was stirred overnight at room temperature. The reaction mixture was filtered, and the filtrate was extracted with ethyl acetate. The organic layer was washed with water and saturated brine, and dried over anhydrous magnesium sulfate, and the solvent was evaporated under reduced pressure to give the title compound (0.44 g) as a crude product. This compound was used in the next step without an additional purification.
MS: [M+H]$^+$ 298.1.

F) 2-((1S,2S)-2-hydroxycyclohexyl)-4,5-dimethyl-6-((6-methylpyridin-3-yl)methyl)isoindolin-1-one To a solution of methyl 2-formyl-3,4-dimethyl-5-((6-methylpyridin-3-yl)methyl)benzoate (0.15 g) in THF (2.90 mL) were added (1S,2S)-aminocyclohexanol (0.06 g) and anhydrous magnesium sulfate (0.11 g), and the mixture was stirred at room temperature for 6 hr. The insoluble substance was removed by filtration, the filtrate was concentrated, and the residue was diluted with methanol (2.90 mL)-THF (2.90 mL). Sodium triacetoxyborohydride (0.21 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (methanol/ethyl acetate) to give the title compound (0.05 g).
$^1$H NMR (300 MHz, DMSO-d$_6$) δ 1.22-1.38 (3H, m), 1.48-1.72 (4H, m), 1.90-2.01 (1H, m), 2.19 (3H, s), 2.22 (3H, s), 2.41 (3H, s), 3.55-3.66 (1H, m), 3.81 (1H, td, J=10.7, 4.1 Hz), 4.05 (2H, s), 4.35 (2H, s), 4.71 (1H, d, J=5.7 Hz), 7.14 (1H, d, J=7.9 Hz), 7.27-7.38 (2H, m), 8.29 (1H, d, J=1.9 Hz).

Example 25-2

2-((1S,2S)-2-Hydroxycyclohexyl)-4,5-dimethyl-6-((6-methylpyridin-3-yl)methyl)isoindolin-1-one was also synthesized by the following method.

A) 5-(chloromethyl)-2-methylpyridine hydrochloride

To a solution of (6-methylpyridin-3-yl)methanol (1.24 g) in THF (12.4 mL) was added thionyl chloride (1.10 mL)

under ice-cooling, and the mixture was stirred overnight at room temperature. The reaction mixture was concentrated under reduced pressure, and the obtained residue was suspended in ethyl acetate. The precipitate was collected by filtration, and washed with ethyl acetate-hexane to give the title compound (1.64 g).

$^1$H NMR (300 MHz, DMSO-d$_6$) δ 2.72 (3H, s), 4.93 (2H, s), 7.86 (1H, d, J=8.1 Hz), 8.44 (1H, dd, J=8.2, 2.0 Hz), 8.85 (1H, d, J=1.9 Hz).

B) methyl 2-hydroxy-3,4-dimethyl-5-((6-methylpyridin-3-yl)methyl)benzoate

To a solution of methyl 2-hydroxy-3,4-dimethyl-5-(4,4,5,5-tetramethyl-1,3,2-dioxaborolan-2-yl)benzoate (2.00 g) in a mixed solvent of DME (30.0 mL)-water (10.0 mL) were added 5-(chloromethyl)-2-methylpyridine hydrochloride (1.22 g), tetrakis(triphenylphosphine)palladium(0) (0.38 g) and sodium carbonate (2.11 g), and the mixture was stirred overnight at 80° C. under argon atmosphere. The reaction mixture was allowed to be cooled to room temperature, water and ethyl acetate were added thereto, and the mixture was partitioned. The organic layer was washed with saturated brine, and dried over anhydrous magnesium sulfate, and the solvent was evaporated under reduced pressure. The residue was purified by silica gel column chromatography (ethyl acetate/hexane) to give the title compound (1.57 g).
MS: [M−H]$^+$ 286.1.

C) methyl 3,4-dimethyl-5-((6-methylpyridin-3-yl)methyl)-2-(((trifluoromethyl)sulfonyl)oxy)benzoate To a mixture of methyl 2-hydroxy-3,4-dimethyl-5-((6-methylpyridin-3-yl)methyl)benzoate (1.57 g), sodium hydride (0.26 g) and DMF (32.0 mL) was added N-phenyl-bis(trifluoromethanesulfonimide)(2.16 g) under ice-cooling, and the mixture was stirred at room temperature for 2 hr. To the reaction mixture was added 1N hydrochloric acid, and the mixture was extracted with ethyl acetate. The organic layer was washed with saturated aqueous sodium bicarbonate solution and saturated brine, and dried over anhydrous magnesium sulfate, and the solvent was evaporated under reduced pressure. The residue was purified by silica gel column chromatography (ethyl acetate/hexane) to give the title compound (0.76 g).
MS: [M+H]$^+$ 418.1.

D) methyl 3,4-dimethyl-5-((6-methylpyridin-3-yl)methyl)-2-vinylbenzoate

To a solution of methyl 3,4-dimethyl-5-((6-methylpyridin-3-yl)methyl)-2-(((trifluoromethyl)sulfonyl)oxy)benzoate (0.76 g) in DMF (16.0 mL) were added tributylvinyltin (0.87 g), bis(triphenylphosphine)palladium(II) dichloride (0.06 g) and lithium chloride (0.57 g), and the mixture was stirred at 90° C. for 1.5 hr under argon atmosphere. To the reaction mixture was added aqueous potassium fluoride solution, and the precipitated insoluble substance was removed by filtration through Celite. The filtrate was diluted with ethyl acetate, and the mixture was washed with saturated brine. The organic layer was dried over anhydrous magnesium sulfate, and the solvent was evaporated under reduced pressure. The residue was purified by silica gel column chromatography (ethyl acetate/hexane) to give the title compound (0.50 g).
MS: [M+H]$^+$ 296.2.

E) methyl 2-formyl-3,4-dimethyl-5-((6-methylpyridin-3-yl)methyl)benzoate

To a solution of methyl 3,4-dimethyl-5-((6-methylpyridin-3-yl)methyl)-2-vinylbenzoate (0.49 g) in a mixed solvent of acetone (6.10 mL)-acetonitrile (6.10 mL)-water (6.10 mL) were added osmium oxide (fixed catalyst I) (0.21 g) and sodium periodate (1.79 g), and the mixture was stirred overnight at room temperature. The reaction mixture was filtered, and the filtrate was extracted with ethyl acetate. The organic layer was washed with saturated brine, and dried over anhydrous magnesium sulfate, and the solvent was evaporated under reduced pressure to give the title compound (0.47 g) as a crude product. This compound was used in the next step without an additional purification.
MS: [M+H]$^+$ 298.1.

F) 2-((1S,2S)-2-hydroxycyclohexyl)-4,5-dimethyl-6-((6-methylpyridin-3-yl)methyl)isoindolin-1-one To a solution of methyl 2-formyl-3,4-dimethyl-5-((6-methylpyridin-3-yl)methyl)benzoate (0.47 g) in THF (9.40 mL) were added (1S,2S)-aminocyclohexanol (0.18 g) and anhydrous magnesium sulfate (0.37 g), and the mixture was stirred at room temperature for 6 hr. The insoluble substance was removed by filtration, the filtrate was concentrated, and the residue was diluted with methanol (9.40 mL)-THF (9.40 mL). Sodium triacetoxyborohydride (0.67 g) was added thereto, and the mixture was stirred overnight at room temperature. The reaction mixture was diluted with ethyl acetate, and the mixture was washed with water and saturated brine. The organic layer was dried over anhydrous magnesium sulfate, and the solvent was evaporated under reduced pressure. The residue was purified by silica gel column chromatography (methanol/ethyl acetate) to give the title compound (0.20 g).

$^1$H NMR (300 MHz, DMSO-d$_6$) δ 1.22-1.39 (3H, m), 1.47-1.75 (4H, m), 1.89-2.02 (1H, m), 2.20 (3H, s), 2.22 (3H, s), 2.41 (3H, s), 3.61 (1H, dd, J=10.0, 5.1 Hz), 3.74-3.88 (1H, m), 4.05 (2H, s), 4.35 (2H, s), 4.69 (1H, d, J=5.5 Hz), 7.14 (1H, d, J=7.9 Hz), 7.29 (1H, s), 7.35 (1H, dd, J=7.9, 2.3 Hz), 8.29 (1H, d, J=1.9 Hz).

X-ray powder diffraction pattern with specific peaks at d value (or d-spacing)=18.5, 10.3, 9.2, 7.0, 5.3, 5.1, 4.7, 4.4, 4.3 and 4.2 Å.

Example 26

1,5-anhydro-2-(6-(4-cyano-3-fluorobenzyl)-4,5-dimethyl-1-oxo-1,3-dihydro-2H-isoindol-2-yl)-2,4-dideoxy-L-threo-pentitol A) methyl 5-(4-cyano-3-fluorobenzyl)-2-hydroxy-3,4-dimethylbenzoate To a mixture of methyl 2-hydroxy-3,4-dimethyl-5-(4,4,5,5-tetramethyl-1,3,2-dioxaborolan-2-yl)benzoate (1.07 g), 4-(chloromethyl)-2-fluorobenzonitrile (0.89 g), 2 mol/L aqueous sodium carbonate solution (3.50 mL) and DME (20.0 mL) was added [1,1'-bis(diphenylphosphino)ferrocene]dichloropalladium(II)dichloromethane adduct (0.14 g) under argon atmosphere, and the mixture was stirred overnight at 80° C., and then at room temperature for weekend. To the reaction mixture was added water at room temperature, and the mixture was extracted with ethyl acetate. The organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (1.10 g).
MS: [M+H]$^+$ 312.0.

B) methyl 5-(4-cyano-3-fluorobenzyl)-3,4-dimethyl-2-vinylbenzoate

A solution of methyl 5-(4-cyano-3-fluorobenzyl)-2-hydroxy-3,4-dimethylbenzoate (1.10 g) in DMF (20.0 mL) was ice-cooled under argon atmosphere, sodium hydride (0.15 g) was added thereto, and the mixture was stirred at room temperature for 30 min. To this reaction mixture was added N-phenylbis(trifluoromethanesulfonimide)(1.51 g) under ice-cooling, and the mixture was stirred at room temperature for 1.5 hr. To the reaction mixture was added 1N hydrochloric acid under ice-cooling, and the mixture was extracted with ethyl acetate. The organic layer was separated, washed with water and saturated brine, and dried over anhydrous magnesium sulfate, and the solvent was evaporated under reduced pressure. The obtained crude methyl 5-(4-cyano-3-fluorobenzyl)-3,4-dimethyl-2-{[(trifluoromethyl)sulfonyl]oxy}benzoate was used in the next step without an additional purification.

To a mixture of the above-mentioned compound, lithium chloride (1.04 g), tributylvinyltin (1.54 mL) and DMF (20.0 mL) was added trans-dichlorobis(triphenylphosphine)palladium(II) (0.12 g) under argon atmosphere, and the mixture was stirred at 90° C. for 2 hr, and then overnight at room temperature. To the reaction mixture was added tributylvinyltin (1.54 mL) under argon atmosphere, and the mixture was stirred at 90° C. for 2 hr. To the reaction mixture were added ethyl acetate and 10% aqueous potassium fluoride solution, and the precipitated insoluble substance was removed by filtration through Celite. The filtrate was extracted with ethyl acetate, the organic layer was separated, washed with water and saturated brine, and dried over anhydrous magnesium sulfate, and the solvent was evaporated under reduced pressure. The residue was purified by silica gel column chromatography (ethyl acetate/hexane) to give the title compound (0.67 g).

MS: [M+H]$^+$ 322.1.

C) methyl 5-(4-cyano-3-fluorobenzyl)-2-formyl-3,4-dimethylbenzoate

To a mixture of methyl 5-(4-cyano-3-fluorobenzyl)-3,4-dimethyl-2-vinylbenzoate (0.67 g) and sodium periodate (2.22 g) in acetone (15.0 mL)-acetonitrile (15.0 mL)-water (15.0 mL) was added osmium oxide (fixed catalyst I) (0.26 g), and the mixture was stirred overnight at room temperature under argon atmosphere. The reaction mixture was filtered, and the filtrate was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.25 g).

MS: [M+H]$^+$ 326.1.

D) 1,5-anhydro-2-(6-(4-cyano-3-fluorobenzyl)-4,5-dimethyl-1-oxo-1,3-dihydro-2H-isoindol-2-yl)-2,4-dideoxy-L-threo-pentitol To a solution of methyl 5-(4-cyano-3-fluorobenzyl)-2-formyl-3,4-dimethylbenzoate (0.25 g) in THF (5.00 mL) was added (3S,4S)-3-aminotetrahydro-2H-pyran-4-ol (0.09 g), and the mixture was stirred overnight at room temperature under argon atmosphere. The reaction mixture was concentrated, and the residue was diluted with acetic acid (5.00 mL). Then, sodium triacetoxyborohydride (0.24 g) was added thereto and the mixture was stirred at room temperature for 2 hr under argon atmosphere. To the reaction mixture was added saturated aqueous sodium bicarbonate, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane, methanol/ethyl acetate) to give the title compound (0.16 g).

$^1$H NMR (300 MHz, CDCl$_3$) δ 1.73-1.89 (1H, m), 2.08-2.18 (4H, m), 2.26 (3H, s), 2.56 (1H, d, J=5.7 Hz), 3.45-3.63 (2H, m), 3.99-4.19 (6H, m), 4.27-4.53 (2H, m), 6.89 (1H, d, J=10.0 Hz), 7.00 (1H, d, J=7.9 Hz), 7.47-7.55 (2H, m).

Example 38 rac-2-(trans-2-methoxycyclohexyl)-5-methyl-6-(4-(1H-pyrazol-1-yl)benzyl)isoindolin-1-one To a solution of rac-2-(trans-2-hydroxycyclohexyl)-5-methyl-6-(4-(1H-pyrazol-1-yl)benzyl)isoindolin-1-one (0.06 g) (obtained in the same manner as in Example 8) in DMF (1.20 mL) was added sodium hydride (9.0 mg) under ice-cooling, and the mixture was stirred for 20 min. Methyl iodide (0.05 mL) was added thereto at the same temperature, and the mixture was stirred at room temperature for two nights under nitrogen atmosphere. To this reaction mixture was added sodium hydride (9.0 mg) under ice-cooling, and the mixture was stirred at room temperature for 7 hr. The reaction mixture was poured into water under ice-cooling, and the mixture was extracted with ethyl acetate. The organic layer was separated, washed with saturated brine, and dried over anhydrous magnesium sulfate, and the solvent was evaporated under reduced pressure. The residue was purified by silica gel column chromatography (ethyl acetate/hexane) and then HPLC (water/acetonitrile) to give the title compound (0.004 g).

$^1$H NMR (300 MHz, DMSO-d$_6$) δ 1.29-1.46 (3H, m), 1.63-1.96 (4H, m), 2.19-2.30 (1H, m), 2.31 (3H, s), 3.27 (3H, s), 3.38-3.51 (1H, m), 4.04-4.17 (3H, m), 4.34 (2H, s), 6.44 (1H, t, J=2.1 Hz), 7.17-7.25 (3H, m), 7.58 (2H, d, J=8.7 Hz), 7.66-7.74 (2H, m), 7.88 (1H, d, J=2.4 Hz).

Example 57

5-ethyl-6-(4-(1-methyl-H-pyrazol-3-yl)benzyl)-2-(tetrahydrofuran-2-ylmethyl)isoindolin-1-one A) methyl 4-bromo-2-hydroxybenzoate To a solution of 4-bromo-2-hydroxybenzoic acid (15.0 g) in methanol (150 mL) was added dropwise thionyl chloride (10.1 mL) under ice-cooling. The reaction solution was stirred at 70° C. overnight under argon atmosphere. The reaction solution was concentrated under reduced pressure, and the residue was purified by silica gel column chromatography (ethyl acetate/hexane) to give the title compound (14.2 g).

$^1$H NMR (300 MHz, DMSO-d$_6$) δ 3.88 (3H, s), 7.10-7.18 (1H, m), 7.21-7.28 (1H, m), 7.69 (1H, d, J=8.3 Hz), 10.65 (1H, s).

B) methyl 2-hydroxy-4-vinylbenzoate

To a solution of methyl 4-bromo-2-hydroxybenzoate (3.0 g) in DMF (50.0 mL) were added tributylvinyltin (6.18 g), bis(triphenylphosphine)palladium(II) chloride (0.46 g) and lithium chloride (4.07 g), and the mixture was stirred at 90° C. for 2 hr under argon atmosphere. To the reaction mixture was added aqueous potassium fluoride solution, and the precipitated insoluble substance was removed by filtration through Celite. The filtrate was diluted with ethyl acetate, and the mixture was washed with water and saturated brine. The organic layer was dried over anhydrous sodium sulfate, and the solvent was evaporated under reduced pressure. The residue was purified by silica gel column chromatography (ethyl acetate/hexane) to give the title compound. This compound was used in the next step without an additional purification.

C) methyl 4-ethyl-2-hydroxybenzoate

To a solution of methyl 2-hydroxy-4-vinylbenzoate (2.31 g) in ethanol (25.0 mL) was added palladium-carbon (1.38 g), and the mixture was stirred overnight at room temperature under hydrogen atmosphere. The insoluble substance was removed by filtration, and the filtrate was concentrated under reduced pressure. The obtained residue was purified by NH silica gel column chromatography (ethyl acetate/hexane) to give the title compound (1.43 g).
MS: [M+H]$^+$ 181.1.

D) methyl 5-bromo-4-ethyl-2-hydroxybenzoate

To a solution of methyl 4-ethyl-2-hydroxybenzoate (1.43 g) in acetic acid (15.0 mL) was added bromine (1.40 g) under ice-cooling, and the mixture was stirred at room temperature for 2 hr under argon atmosphere. To the reaction mixture was added water, the resulting solid was collected by filtration, and dried under reduced pressure to give the title compound (2.21 g) as a mixture with methyl 3,5-dibromo-4-ethyl-2-hydroxybenzoate (2:1). This compound was used in the next step without an additional purification.

E) methyl 4-ethyl-2-hydroxy-5-(4,4,5,5-tetramethyl-1,3,2-dioxaborolan-2-yl)benzoate A mixture of the mixture (1.00 g) of methyl 5-bromo-4-ethyl-2-hydroxybenzoate and methyl 3,5-dibromo-4-ethyl-2-hydroxybenzoate, bis(pinacolato)diboron (1.47 g), potassium acetate (1.14 g), trans-dichlorobis(triphenylphosphine)palladium(II) (0.14 g) and toluene (20.0 mL) was stirred overnight at 100° C. under argon atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (0.82 g). This compound was used in the next step without an additional purification.
MS: [M+H]$^+$ 307.2.

F) methyl 4-ethyl-2-hydroxy-5-(4-(1-methyl-1H-pyrazol-3-yl)benzyl)benzoate

A mixture of methyl 4-ethyl-2-hydroxy-5-(4,4,5,5-tetramethyl-1,3,2-dioxaborolan-2-yl)benzoate (0.41 g), 3-(4-(bromomethyl)phenyl)-1-methyl-1H-pyrazole (0.44 g), sodium carbonate (0.28 g), tetrakis(triphenylphosphine)palladium (0) (0.15 g), DME (15.0 mL) and water (5.0 mL) was stirred overnight at 90° C. under argon atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (0.26 g).
MS: [M+H]$^+$ 351.1.

G) methyl 4-ethyl-5-(4-(1-methyl-1H-pyrazol-3-yl)benzyl)-2-(((trifluoromethyl)sulfonyl)oxy)benzoate To a solution of methyl 4-ethyl-2-hydroxy-5-(4-(1-methyl-1H-pyrazol-3-yl)benzyl)benzoate (0.26 g) and N-phenylbis(trifluoromethanesulfonimide) (0.29 g) in DMF (3.00 mL) was added sodium hydride (0.04 g) under ice-cooling, and the mixture was stirred at room temperature for 1 hr under argon atmosphere. The reaction mixture was diluted with ethyl acetate, and the mixture was washed with saturated brine. The organic layer was dried over anhydrous sodium sulfate, and the solvent was evaporated under reduced pressure. The residue was purified by silica gel column chromatography (ethyl acetate/hexane) to give the title compound (0.32 g).
MS: [M+H]$^+$ 483.1.

H) methyl 4-ethyl-5-(4-(1-methyl-1H-pyrazol-3-yl)benzyl)-2-vinylbenzoate

A mixture of methyl 4-ethyl-5-(4-(1-methyl-1H-pyrazol-3-yl)benzyl)-2-(((trifluoromethyl)sulfonyl)oxy)benzoate (0.32 g), tributylvinyltin (0.32 g), trans-dichlorobis(triphenylphosphine)palladium(II) (0.02 g), lithium chloride (0.21 g) and DMF (6.00 mL) was stirred at 90° C. for 2 hr under argon atmosphere. To the reaction mixture was added aqueous potassium fluoride solution, and the precipitated insoluble substance was removed by filtration. The filtrate was diluted with ethyl acetate, and the mixture was washed with saturated brine. The organic layer was dried over anhydrous sodium sulfate, and the solvent was evaporated under reduced pressure. The residue was purified by NH silica gel column chromatography (ethyl acetate/hexane) to give the title compound (0.21 g). This compound was used in the next step without an additional purification.

I) methyl 4-ethyl-2-formyl-5-(4-(1-methyl-1H-pyrazol-3-yl)benzyl)benzoate

A mixture of methyl 4-ethyl-5-(4-(1-methyl-1H-pyrazol-3-yl)benzyl)-2-vinylbenzoate (0.21 g), osmium oxide (fixed catalyst I) (0.08 g) and sodium periodate (0.64 g) in acetone (4.00 mL)-acetonitrile (4.00 mL)-water (4.00 mL) was stirred overnight at room temperature. The insoluble substance was removed by filtration, the filtrate was diluted with ethyl acetate, and the mixture was washed with saturated brine. The organic layer was dried over anhydrous sodium sulfate, and the solvent was evaporated under reduced pressure to give the title compound (0.21 g) as a crude product. This compound was used in the next step without an additional purification.

J) 5-ethyl-6-(4-(1-methyl-1H-pyrazol-3-yl)benzyl)-2-((tetrahydrofuran-2-yl)methyl)isoindolin-1-one A mixture of methyl 4-ethyl-2-formyl-5-(4-(1-methyl-1H-pyrazol-3-yl)benzyl)benzoate (0.11 g), (tetrahydrofuran-2-yl)methanamine (0.03 g) and anhydrous magnesium sulfate (0.07 g) in THF (3.00 mL) was stirred overnight at room temperature. The insoluble substance was removed by filtration, and the filtrate was concentrated under reduced pressure. The residue was diluted with acetic acid (3.00 mL), sodium triacetoxyborohydride (0.09 g) was added thereto, and the mixture was stirred overnight at room temperature. The reaction mixture was neutralized with saturated aqueous sodium bicarbonate solution, and the mixture was extracted with ethyl acetate. The organic layer was washed with water and saturated brine, and dried over anhydrous sodium sulfate, and the solvent was evaporated under reduced pressure. The residue was purified by NH silica gel column chromatography (ethyl acetate/hexane), and crystallized from ethyl acetate/hexane to give the title compound (0.03 g).

¹H NMR (300 MHz, DMSO-d₆) δ 1.11 (3H, t, J=7.6 Hz), 1.47-1.63 (1H, m), 1.74-2.00 (3H, m), 2.69 (2H, q, J=7.7 Hz), 3.44-3.67 (3H, m), 3.72-3.82 (1H, m), 3.86 (3H, s), 3.98-4.06 (1H, m), 4.09 (2H, s), 4.50 (2H, d, J=4.5 Hz), 6.62 (1H, d, J=2.3 Hz), 7.15 (2H, d, J=8.3 Hz), 7.42 (2H, s), 7.63-7.75 (3H, m).

Example 96

4-fluoro-5-methoxy-6-(4-(1H-pyrazol-1-yl)benzyl)-2-(tetrahydrofuran-2-ylmethyl)isoindolin-1-one A) 2-fluoro-3-methoxyphenol To a solution of 2-fluoro-3-methoxyphenylboronic acid (30.4 g) in THF (300 mL) was added dropwise aqueous hydrogen peroxide (100 mL, 30% wt in water), and the mixture was heated with reflux for 1 hr. The reaction mixture was allowed to be cooled to room temperature, saturated aqueous sodium sulfite was added thereto, and the mixture was extracted with ethyl acetate. The organic layer was dried over anhydrous sodium sulfate, and the solvent was evaporated under reduced pressure. The residue was purified by combi flash (petroleum ether/ethyl acetate) to give the title compound (24.8 g).
¹H NMR (400 MHz, CDCl₃) δ 3.88 (3H, s), 5.23 (1H, brs), 6.53 (1H, t, J=8.4 Hz), 6.62 (1H, t, J=8.4 Hz), 6.93 (1H, td, J=8.4, 2.0 Hz).

B) 3-fluoro-2-hydroxy-4-methoxybenzaldehyde

To a solution of 2-fluoro-3-methoxyphenol (22.0 g) and triethylamine (93.9 g) in dichloroethane (250 mL) was added magnesium chloride (71.7 g), and the mixture was stirred at 40° C. for 1 hr. To this mixture was added paraformaldehyde (46.5 g), and the mixture was stirred for 16 hr. The reaction solution was allowed to be cooled to room temperature, 1N hydrochloric acid was added thereto, and the mixture was extracted with dichloromethane. The organic layer was dried over anhydrous sodium sulfate, and the solvent was evaporated under reduced pressure. The residue was purified by combi flash (petroleum ether/ethyl acetate) to give the title compound (26.0 g).
¹H NMR (400 MHz, DMSO-d₆) δ 3.98 (3H, s), 6.64 (1H, dd, J=8.8, 6.8 Hz), 7.32 (1H, dd, J=8.8, 1.6 Hz), 9.77 (1H, d, J=2.0 Hz). One active proton was not observed.

C) 3-fluoro-2-hydroxy-4-methoxybenzoic acid

To a mixture of 3-fluoro-2-hydroxy-4-methoxybenzaldehyde (10.0 g) and sodium dihydrogenphosphate (22.9 g) in DMSO (100 mL) and water (25.0 mL) was added dropwise an aqueous solution (30.0 mL) of sodium chlorite (14.5 g), and the mixture was stirred at 20° C. for 16 hr. The solvent was evaporated under reduced pressure, the residue was diluted with water, and the mixture was extracted with ethyl acetate (×6). The organic layer was washed with saturated brine, and dried over anhydrous sodium sulfate, and the solvent was evaporated under reduced pressure to give the title compound (7.42 g).
¹H NMR (400 MHz, DMSO-d₆) δ 3.89 (3H, s), 6.75 (1H, t, J=8.4 Hz), 7.59 (1H, dd, J=9.2, 2.0 Hz). Two active protons were not observed.

D) 5-bromo-3-fluoro-2-hydroxy-4-methoxybenzoic acid

To a solution of 3-fluoro-2-hydroxy-4-methoxybenzoic acid (7.30 g) in DMF (70.0 mL) was added NBS, and the mixture was stirred at 25° C. for 2 hr. The solvent was evaporated under reduced pressure, and the residue was diluted with ethyl acetate. The mixture was washed with water and saturated brine, and dried over anhydrous sodium sulfate, and the solvent was evaporated under reduced pressure to give the title compound (8.86 g).
¹H NMR (400 MHz, DMSO-d₆) δ 4.00 (3H, s), 7.74 (1H, d, J=2.0 Hz). Two active protons were not observed and it contained some impurity.

E) methyl 5-bromo-3-fluoro-2-hydroxy-4-methoxybenzoate

To a solution of 5-bromo-3-fluoro-2-hydroxy-4-methoxybenzoic acid (0.70 g) in methanol (15.0 mL) was added dropwise thionyl chloride (0.39 mL) under ice-cooling. The reaction solution was stirred at 70° C. for 15 hr under argon atmosphere, and then overnight at room temperature. To the reaction mixture was added water, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.52 g).
¹H NMR (300 MHz, CDCl₃) δ 3.97 (3H, s), 4.12 (3H, d, J=3.0 Hz), 7.82 (1H, d, J=2.3 Hz), 10.84 (1H, s).

F) methyl 3-fluoro-2-hydroxy-4-methoxy-5-[4-(1H-pyrazol-1-yl)benzyl]benzoate

To a solution of methyl 5-bromo-3-fluoro-2-hydroxy-4-methoxybenzoate (0.52 g) in DME (10.0 mL) were added bis(pinacolato)diboron (0.71 g), potassium acetate (0.55 g) and [1,1'-bis(diphenylphosphino)ferrocene]palladium(II) dichloride dichloromethane adduct (0.08 g), and the mixture was stirred at 80° C. for 5 hr under argon atmosphere. The reaction mixture was allowed to be cooled to room temperature, water was added thereto, and the mixture was diluted with ethyl acetate. The organic layer was washed with water and saturated brine, and dried over anhydrous magnesium sulfate, and the solvent was evaporated under reduced pressure to give methyl 3-fluoro-2-hydroxy-4-methoxy-5-(4,4,5,5-tetramethyl-1,3,2-dioxaborolan-2-yl)benzoate as a crude product. To a solution of the above-mentioned crude product in DME (10.0 mL) were added 1-(4-(bromomethyl)phenyl)-1H-pyrazole (0.44 g), [1,1'-bis(diphenylphosphino)ferrocene]palladium(II) dichloride dichloromethane adduct (0.08 g) and 2M aqueous sodium carbonate solution (1.86 mL), and the mixture was stirred at 80° C. overnight under argon atmosphere. The reaction mixture was allowed to be cooled to room temperature, water was added thereto, and the mixture was extracted with ethyl acetate. The organic layer was washed with water and saturated brine, and dried over anhydrous magnesium sulfate, and the solvent was evaporated under reduced pressure. The residue was purified by silica gel column chromatography (ethyl acetate/hexane) to give the title compound (0.21 g).
¹H NMR (300 MHz, CDCl₃) δ 3.92 (2H, s), 3.93 (3H, s), 3.94-3.97 (3H, m), 6.46 (1H, t, J=2.2 Hz), 7.24 (2H, s), 7.41 (1H, d, J=2.1 Hz), 7.61 (2H, d, J=8.5 Hz), 7.72 (1H, d, J=1.5 Hz), 7.88-7.92 (1H, m), 10.81 (1H, s).

G) methyl 2-ethenyl-3-fluoro-4-methoxy-5-[4-(1H-pyrazol-1-yl)benzyl]benzoate

To a solution of methyl 3-fluoro-2-hydroxy-4-methoxy-5-[4-(1H-pyrazol-1-yl)benzyl]benzoate (0.21 g) in DMF (5.00 mL) was added sodium hydride (0.03 g) under ice-cooling, and the mixture was stirred at room temperature for 0.5 hr under argon atmosphere. To the reaction mixture was added N-phenylbis(trifluoromethanesulfonimide) (0.23 g), and the mixture was stirred at room temperature for 0.5 hr under argon atmosphere. To the reaction mixture was added 1N hydrochloric acid, and the mixture was extracted with ethyl acetate. The organic layer was washed with water and saturated brine, and dried over anhydrous magnesium sulfate, and the solvent was evaporated under reduced pressure to give methyl 3-fluoro-4-methoxy-5-[4-(1H-pyrazol-1-yl) benzyl]-2-{[(trifluoromethyl)sulfonyl]oxy}benzoate as a crude product. To a mixture of the obtained crude product, tributylvinyltin (0.26 mL) and lithium chloride (0.19 g) in DMF (5.00 mL) was added bis(triphenylphosphine)palladium(II) dichloride (0.02 g), and the mixture was stirred at 90° C. for 2 hr under argon atmosphere. To the reaction mixture was added 10% aqueous potassium fluoride solution, and the precipitated insoluble substance was removed by filtration through Celite. To the filtrate was added water, and the mixture was extracted with ethyl acetate. The organic layer was washed with water and saturated brine, and dried over anhydrous sodium sulfate, and the solvent was evaporated under reduced pressure. The residue was purified by silica gel column chromatography (ethyl acetate/hexane) to give the title compound (0.12 g).

MS: $[M+H]^+$ 367.2.

H) 4-fluoro-5-methoxy-6-(4-(1H-pyrazol-1-yl)benzyl)-2-(tetrahydrofuran-2-ylmethyl)isoindolin-1-one To a solution of methyl 2-ethenyl-3-fluoro-4-methoxy-5-[4-(1H-pyrazol-1-yl)benzyl]benzoate (0.12 g) in a mixed solvent of acetone (2.00 mL)-acetonitrile (2.00 mL)-water (2.00 mL) were added osmium oxide (fixed catalyst I) (0.04 g) and sodium periodate (0.35 g), and the mixture was stirred at room temperature for 3 hr under argon atmosphere. The reaction mixture was filtered, and the filtrate was concentrated under reduced pressure. To the residue was added water, and the mixture was extracted with ethyl acetate. The organic layer was washed with saturated brine, and dried over anhydrous sodium sulfate, and the solvent was evaporated under reduced pressure to give methyl 3-fluoro-2-formyl-4-methoxy-5-[4-(1H-pyrazol-1-yl)benzyl]benzoate as a crude product. The obtained crude product (20% v/v) was dissolved in THF (2.00 mL), (tetrahydrofuran-2-yl) methanamine (0.006 g) was added thereto, and the mixture was stirred at room temperature for 1 hr. The reaction solution was concentrated under reduced pressure, and the residue was diluted with acetic acid (1.00 mL). Sodium triacetoxyborohydride (0.03 g) was added thereto, and the mixture was stirred overnight at room temperature. The reaction mixture was neutralized with saturated aqueous sodium hydrogencarbonate solution, and the mixture was extracted with ethyl acetate. The organic layer was washed with water and saturated brine, and dried over anhydrous magnesium sulfate, and the solvent was evaporated under reduced pressure. The residue was purified by HPLC (water/acetonitrile, containing 0.1% TFA). The fractions were combined, saturated aqueous sodium hydrogencarbonate solution was added thereto, and the mixture was extracted with ethyl acetate. The organic layer was dried over anhydrous magnesium sulfate, and the solvent was evaporated under reduced pressure to give the title compound (2.90 mg).

MS: $[M+H]^+$ 422.2.

Example 113 rac-3-fluoro-4-((2-(trans-4-hydroxytetrahydro-2H-pyran-3-yl)-6,7-dimethyl-3-oxoisoindolin-5-yl) methyl)benzamide To a mixture of rac-3-fluoro-4-((2-(trans-4-hydroxytetrahydro-2H-pyran-3-yl)-6,7-dimethyl-3-oxoisoindolin-5-yl) methyl)benzonitrile (0.08 g) and potassium carbonate (0.08 g) in DMSO (2.00 mL) was added 35% aqueous hydrogen peroxide (0.17 mL) under ice-cooling, and the mixture was stirred at room temperature for 3 hr. The reaction solution was diluted with water, and the mixture was extracted with ethyl acetate-THF. The organic layer was washed with saturated brine, and dried over anhydrous magnesium sulfate, and the solvent was evaporated under reduced pressure. The residue was washed with ethyl acetate to give the title compound (0.07 g).

MS: $[M+H]^+$ 413.2.

The compounds of Examples 27 to 37, 39 to 56, 58 to 95, 97 to 112 and 114 to 168 in Table 1 were synthesized according to the method shown in the above-mentioned Examples or a method analogous thereto. The Example compounds are shown in Table 1. MS in the tables means actual measured value.

TABLE 1

| Ex. No. | IUPAC Name | structure formula | MS |
|---|---|---|---|
| 1 | rac-2-(trans-2-hydroxycyclohexyl)-6-((6-(1-methyl-1H-pyrazol-4-yl)pyridin-3-yl)methyl)isoindolin-1-one | | 403.2 |

TABLE 1-continued

| Ex. No. | IUPAC Name | structure formula | MS |
|---|---|---|---|
| 2 | rac-5-chloro-2-(trans-2-hydroxycyclohexyl)-6-(4-(1H-pyrazol-1-yl)benzyl)isoindolin-1-one | | 422.1 |
| 3 | rac-2-(trans-2-hydroxycyclohexyl)-5-methoxy-6-(4-(1H-pyrazol-1-yl)benzyl)isoindolin-1-one | | 418.2 |
| 4 | 2-((1S,2S)-2-hydroxycyclopentyl)-5-methyl-6-(4-(1H-pyrazol-1-yl)benzyl)isoindolin-1-one | | 388.2 |

TABLE 1-continued

| Ex. No. | IUPAC Name | structure formula | MS |
|---|---|---|---|
| 5 | rac-6-((6-(1,3-dimethyl-1H-pyrazol-4-yl)pyridin-3-yl)methyl)-2-(trans-2-hydroxycyclohexyl)-5-methylisoindolin-1-one | | 431.2 |
| 6 | rac-2-(trans-2-hydroxycyclohexyl)-5-methyl-6-((2'-methyl-2,4'-bipyridin-5-yl)methyl)isoindolin-1-one | | 428.2 |
| 7 | 3-fluoro-2-(5-methyl-1-oxo-6-(4-(1H-pyrazol-1-yl)benzyl)-1,3-dihydro-2H-isoindol-2-yl)benzonitrile | | 423.1 |

TABLE 1-continued

| Ex. No. | IUPAC Name | structure formula | MS |
|---|---|---|---|
| 8 | 5-methyl-6-(4-(1H-pyrazol-1-yl)benzyl)-2-(tetrahydro-2H-pyran-4-yl)isoindolin-1-one | | 388.2 |
| 9 | rac-5-cyclopropyl-2-(trans-2-hydroxycyclopentyl)-6-(4-(1H-pyrazol-1-yl)benzyl)isoindolin-1-one | | 414.2 |
| 10 | rac-4-chloro-2-(trans-2-hydroxycyclohexyl)-6-(4-(1H-pyrazol-1-yl)benzyl)-5-(trifluoromethyl)isoindolin-1-one | | 490.1 |

| Ex. No. | IUPAC Name | structure formula | MS |
|---|---|---|---|
| 11 | rac-2-(trans-2-hydroxycyclohexyl)-4-methyl-1-oxo-6-(4-(1H-pyrazol-1-yl)benzyl)isoindoline-5-carbonitrile | 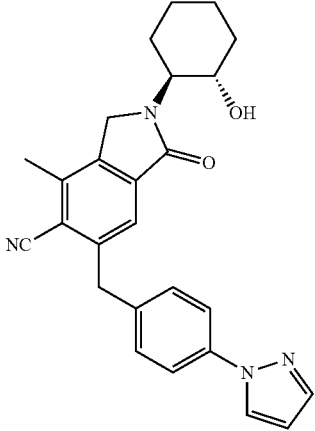 [SMILES: Cc1c(C#N)c(Cc2ccc(-n3cccn3)cc2)cc2c1CN([C@H]1CCCC[C@@H]1O)C2=O] | 427.2 |
| 12 | rac-4-chloro-2-(trans-2-hydroxycyclohexyl)-5-methoxy-6-(4-(1H-pyrazol-1-yl)benzyl)isoindolin-1-one | 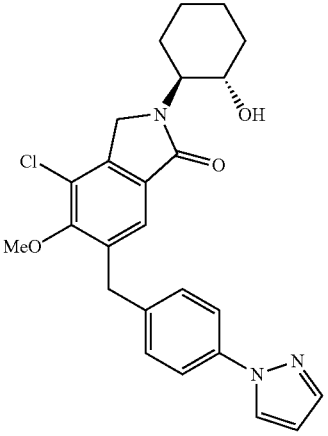 [SMILES: COc1c(Cc2ccc(-n3cccn3)cc2)cc2c(c1Cl)CN([C@H]1CCCC[C@@H]1O)C2=O] | 452.1 |
| 13 | 2-((1S,2S)-2-hydroxycyclopentyl)-4,5-dimethyl-6-(4-(1-methyl-1H-pyrazol-3-yl)benzyl)isoindolin-1-one | 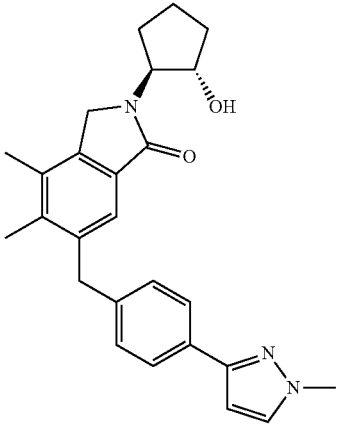 | 416.2 |

TABLE 1-continued

| Ex. No. | IUPAC Name | structure formula | MS |
|---|---|---|---|
| 14 | 4,5-dimethyl-6-(4-(1-methyl-1H-1,2,3--triazol-4-yl)benzyl)-2-((2S)-tetrahydrofuran-2-ylmethyl)isoindolin-1-one | | 417.1 |
| 15 | 2-(2-hydroxy-2-methylpropyl)-4,5-dimethyl-6-(4-(1H-pyrazol-1-yl)benzyl)isoindolin-1-one | | 390.1 |
| 16 | 6-(2-fluoro-4-(1H-pyrazol-1-yl)benzyl)-2-((1S,2S)-2-hydroxycyclopentyl)-4,5-dimethylisoindolin-1-one | | 420.1 |

TABLE 1-continued

| Ex. No. | IUPAC Name | structure formula | MS |
|---|---|---|---|
| 17 | 1,5-anhydro-2-(6-(4-chlorobenzyl)-4,5-dimethyl-1-oxo-1,3-dihydro-2H-isoindol-2-yl)-2,4-dideoxy-L-threo-pentitol | | 386.0 |
| 18 | 2-[(3S,4S)-4-hydroxytetrahydro-2H-pyran-3-yl]-6-(4-methoxybenzyl)-4,5-dimethyl-2,3-dihydro-1H-isoindol-1-one Alias; 1,5-anhydro-2,4-dideoxy-2-(6-(4-methoxybenzyl)-4,5-dimethyl-1-oxo-1,3-dihydro-2H-isoindol-2-yl)-L-threo-pentitol | | 382.2 |
| 19 | 1,5-anhydro-2,4-dideoxy-2-(6-(3-fluoro-4-(methylcarbamoyl)benzyl)-4,5-dimethyl-1-oxo-1,3-dihydro-2H-isoindol-2-yl)-L-threo-pentitol | | 427.1 |

TABLE 1-continued

| Ex. No. | IUPAC Name | structure formula | MS |
|---|---|---|---|
| 20 | 4-fluoro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one Alias; 1,5-anhydro-2,4-dideoxy-2-(4-fluoro-5-methyl-1-oxo-6-(4-(1H-pyrazol-1-yl)benzyl)-1,3-dihydro-2H-isoindol-2-yl)-L-threo-penitol | | 422.1 |
| 21 | 1,5-anhydro-2,4-dideoxy-2-(5-methyl-1-oxo-6-(4-(1H-pyrazol-1-yl)benzyl)-1,3-dihydro-2H-isoindol-2-yl)-L-threo-pentitol | | 404.1 |
| 22 | 1,5-anhydro-2,4-dideoxy-2-(6-(4-(difluoromethoxy)benzyl)-4,5-dimethyl-1-oxo-1,3-dihydro-2H-isoindol-2-yl)-L-threo-pentitol | | 418.0 |

TABLE 1-continued

| Ex. No. | IUPAC Name | structure formula | MS |
|---|---|---|---|
| 23 | 1,5-anhydro-2,4-dideoxy-2-(6-(4-fluoro-3-methoxybenzyl)-4,5-dimethyl-1-oxo-1,3-dihydro-2H-isoindol-2-yl)-L-threo-pentitol | | 400.1 |
| 24 | 1,5-anhydro-2-(4-chloro-6-(4-methoxybenzyl)-5-methyl-1-oxo-1,3-dihydro-2H-isoindol-2-yl)-2,4-dideoxy-L-threo-pentitol | | 402.1 |
| 25 | 2-((1S,2S)-2-hydroxycyclohexyl)-4,5-dimethyl-6-((6-methylpyridin-3-yl)methyl)isoindolin-1-one | | 365.2 |
| 26 | 1,5-anhydro-2-(6-(4-cyano-3-fluorobenzyl)-4,5-dimethyl-1-oxo-1,3-dihydro-2H-isoindol-2-yl)-2,4-dideoxy-L-threo-pentitol | | 395.1 |

| Ex. No. | IUPAC Name | structure formula | MS |
|---|---|---|---|
| 27 | 2-(2-fluorophenyl)-6-((6-(1-methyl-1H-pyrazol-4-yl)pyridin-3-yl)methyl)isoindolin-1-one | | 399.1 |
| 28 | rac-2-(trans-2-hydroxycyclohexyl)-4,5-dimethyl-6-((6-(L-methyl-1H-pyrazol-4-yl)pyridin-3-yl)methyl)isoindolin-1-one | | 431.2 |
| 29 | rac-2-(trans-2-hydroxycyclohexyl)-4,5-dimethyl-6-(4-(1H-pyrazol-1-yl)benzyl)isoindolin-1-one | | 416.2 |

TABLE 1-continued

| Ex. No. | IUPAC Name | structure formula | MS |
|---|---|---|---|
| 30 | rac-2-(trans-2-hydroxycyclohexyl)-4-methyl-6-(4-(1H-pyrazol-1-yl)benzyl)isoindolin-1-one | | 402.2 |
| 31 | rac-2-(trans-2-hydroxycyclopentyl)-4-methyl-6-(4-(1H-pyrazol-1-yl)benzyl)isoindolin-1-one | | 388.1 |
| 32 | rac-2-(trans-2-hydroxycyclohexyl)-5-methyl-6-(4-(1H-pyrazol-1-yl)benzyl)isoindolin-1-one | | 402.2 |

TABLE 1-continued

| Ex. No. | IUPAC Name | structure formula | MS |
|---|---|---|---|
| 33 | rac-2-(trans-2-hydroxycyclopentyl)-5-methyl-6-(4-(1H-pyrazol-1-yl)benzyl)isoindolin-1-one | | 388.2 |
| 34 | rac-2-(trans-2-hydroxycyclopentyl)-4,5-dimethyl-6-(4-(1H-pyrazol-1-yl)benzyl)isoindolin-1-one | | 402.1 |
| 35 | rac-2-(trans-4-hydroxytetrahydro-2H-pyran-3-yl)-4,5-dimethyl-6-(4-(1H-pyrazol-1-yl)benzyl)-2,3-dihydro-1H-isoindol-1-one | | 418.2 |

TABLE 1-continued
| Ex. No. | IUPAC Name | structure formula | MS |
|---|---|---|---|
| 36 | 5-methyl-6-(4-(1H-pyrazol-1-yl)benzyl)-2-(tetrahydrofuran-2-ylmethyl)isoindolin-1-one | 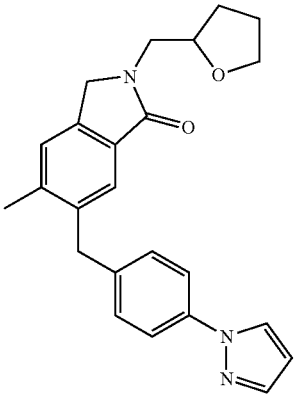 | 388.2 |
| 37 | 2-(1-(hydroxymethyl)cyclopentyl)-5-methyl-6-(4-(1H-pyrazol-1-yl)benzyl)isoindolin-1-one | 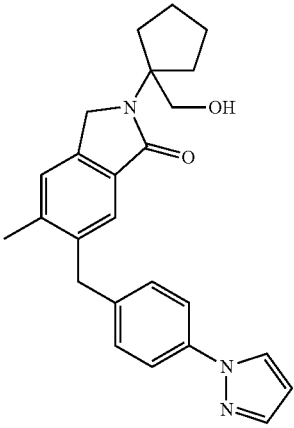 [SMILES: Cc1cc2c(cc1Cc1ccc(-n3cccn3)cc1)C(=O)N(C1(CO)CCCC1)C2] | 402.2 |
| 38 | rac-2-(trans-2-methoxycyclohexyl)-5-methyl-6-(4-(1H-pyrazol-1-yl)benzyl)isoindolin-1-one | 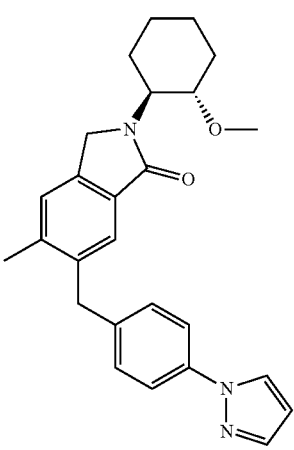 [SMILES: CO[C@H]1CCCC[C@@H]1N1Cc2cc(C)c(Cc3ccc(-n4cccn4)cc3)cc2C1=O] | 416.2 |

TABLE 1-continued

| Ex. No. | IUPAC Name | structure formula | MS |
|---|---|---|---|
| 39 | 2-((1R,2R)-2-hydroxycyclopentyl)-5-methyl-6-(4-(1H-pyrazol-1-yl)benzyl)isoindolin-1-one | | 388.2 |
| 40 | rac-6-((6-(1,3-dimethyl-1H-pyrazol-4-yl)pyridin-3-yl)methyl)-2-(trans-2-hydroxycyclopentyl)-5-methylisoindolin-1-one | | 417.1 |
| 41 | rac-2-(trans-2-hydroxycyclopentyl)-5-methyl-6-((2'-methyl-2,4'-bipyridin-5-yl)methyl)isoindolin-1-one | | 414.2 |

TABLE 1-continued

| Ex. No. | IUPAC Name | structure formula | MS |
|---|---|---|---|
| 42 | rac-2-(trans-2-hydroxycyclohexyl)-5-methyl-6-((6-(1-methyl-1H-pyrazol-3-yl)pyridin-3-yl)methyl)isoindolin-1-one | | 417.1 |
| 43 | rac-2-(trans-2-hydroxycyclopentyl)-5-methyl-6-((6-(1-methyl-1H-pyrazol-3-yl)pyridin-3-yl)methyl)isoindolin-1-one | | 403.2 |
| 44 | rac-6-(2,4-difluorobenzyl)-2-(trans-2-hydroxycyclohexyl)-5-methylisoindolin-1-one | | 372.2 |

TABLE 1-continued
| Ex. No. | IUPAC Name | structure formula | MS |
|---|---|---|---|
| 45 | rac-6-(2,4-difluorobenzyl)-2-(trans-2-hydroxycyclopentyl)-5-methylisoindolin-1-one | 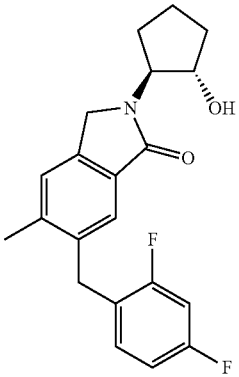 [SMILES: Cc1cc2c(cc1Cc1ccc(F)cc1F)C(=O)N([C@H]1CCC[C@@H]1O)C2] | 358.1 |
| 46 | 2-((1R,2S)-2-hydroxycyclopentyl)-5-methyl-6-(4-(1H-pyrazol-1-yl)benzyl)isoindolin-1-one | 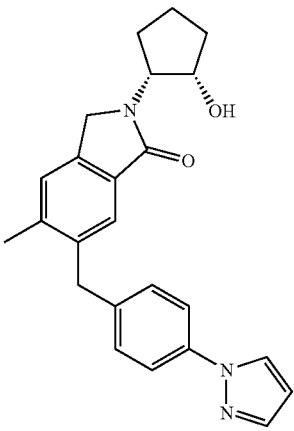 [SMILES: Cc1cc2c(cc1Cc1ccc(-n3cccn3)cc1)C(=O)N([C@@H]1CCC[C@@H]1O)C2] | 388.2 |
| 47 | rac-2-(trans-2-hydroxycyclohexyl)-5-methyl-6-(4-(1-methyl-1H-1,2,3-triazol-4-yl)benzyl)isoindolin-1-one | 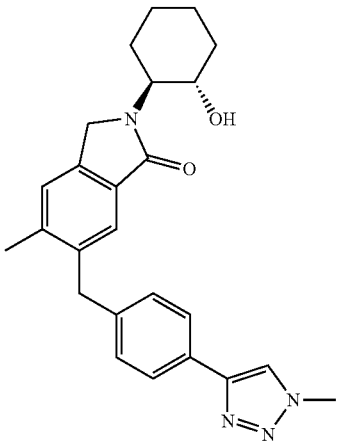 | 417.1 |

TABLE 1-continued

| Ex. No. | IUPAC Name | structure formula | MS |
|---|---|---|---|
| 48 | rac-2-(trans-2-hydroxycyclopentyl)-5-methyl-6-(4-(1-methyl-1H-1,2,3-triazol-4-yl)benzyl)isoindolin-1-one | | 403.2 |
| 49 | 5-methyl-6-(4-(1-methyl-1H-1,2,3-triazol-4-yl)benzyl)-2-(tetrahydrofuran-2-ylmethyl)isoindolin-1-one | | 403.2 |
| 50 | 5-methyl-6-(4-(1H-pyrazol-1-yl)benzyl)-2-(tetrahydro-2H-pyran-3-yl)isoindolin-1-one | | 388.2 |

TABLE 1-continued

| Ex. No. | IUPAC Name | structure formula | MS |
|---|---|---|---|
| 51 | rac-2-(trans-2-hydroxycyclopentyl)-5-methyl-6-(4-(1-methyl-1H-pyrazol-3-yl)benzyl)isoindolin-1-one | | 402.1 |
| 52 | 5-methyl-6-(4-(1-methyl-1H-pyrazol-3-yl)benzyl)-2-(tetrahydrofuran-2-ylmethyl)isoindolin-1-one | | 402.1 |
| 53 | rac-6-(2-fluoro-4-(1-methyl-1H-1,2,3-triazol-4-yl)benzyl)-2-(trans-2-hydroxycyclopentyl)-5-methylisoindolin-1-one | | 421.1 |

TABLE 1-continued

| Ex. No. | IUPAC Name | structure formula | MS |
|---|---|---|---|
| 54 | 6-(2-fluoro-4-(1-methyl-1H-1,2,3-triazol-4-yl)benzyl)-5-methyl-2-(tetrahydrofuran-2-ylmethyl)isoindolin-1-one | | 421.2 |
| 55 | rac-6-(4-(1,3-dimethyl-1H-pyrazol-4-yl)benzyl)-2-(trans-2-hydroxycyclopentyl)-5-methylisoindolin-1-one | | 416.2 |
| 56 | 6-(4-(1,3-dimethyl-1H-pyrazol-4-yl)benzyl)-5-methyl-2-(tetrahydrofuran-2-ylmethyl)isoindolin-1-one | | 416.2 |

TABLE 1-continued

| Ex. No. | IUPAC Name | structure formula | MS |
|---|---|---|---|
| 57 | 5-ethyl-6-(4-(1-methyl-1H-pyrazol-3-yl)benzyl)-2-(tetrahydrofuran-2-ylmethyl)isoindolin-1-one | | 416.1 |
| 58 | 5-ethyl-6-(4-(1H-pyrazol-1-yl)benzyl)-2-(tetrahydrofuran-2-ylmethyl)isoindolin-1-one | | 402.1 |
| 59 | rac-5-ethyl-2-(trans-2-hydroxycyclopentyl)-6-(4-(1H-pyrazol-1-yl)benzyl)isoindolin-1-one | | 402.1 |

TABLE 1-continued

| Ex. No. | IUPAC Name | structure formula | MS |
|---|---|---|---|
| 60 | 5-chloro-6-(4-(1-methyl-1H-1,2,3-triazol-4-yl)benzyl)-2-(tetrahydrofuran-2-ylmethyl)isoindolin-1-one | | 423.1 |
| 61 | 5-cyclopropyl-6-(4-(1-methyl-1H-1,2,3-triazol-4-yl)benzyl)-2-(tetrahydrofuran-2-ylmethyl)isoindolin-1-one | | 429.2 |
| 62 | 5-cyclopropyl-6-(4-(1H-pyrazol-1-yl)benzyl)-2-(tetrahydrofuran-2-ylmethyl)isoindolin-1-one | | 414.1 |

TABLE 1-continued

| Ex. No. | IUPAC Name | structure formula | MS |
|---|---|---|---|
| 63 | rac-5-ethyl-2-(trans-2-hydroxycyclopentyl)-6-(4-(1-methyl-1H-pyrazol-3-yl)benzyl)isoindolin-1-one | | 416.2 |
| 64 | rac-5-cyclopropyl-2-(trans-2-hydroxycyclopentyl)-6-(4-(1-methyl-1H-1,2,3-triazol-4-yl)benzyl)isoindolin-1-one | | 429.2 |
| 65 | rac-6-(2-fluoro-4-(1-methyl-1H-pyrazol-3-yl)benzyl)-2-(trans-2-hydroxycyclopentyl)-5-methylisoindolin-1-one | | 420.1 |

TABLE 1-continued

| Ex. No. | IUPAC Name | structure formula | MS |
|---|---|---|---|
| 66 | 6-(2-fluoro-4-(1-methyl-1H-pyrazol-3-yl)benzyl)-5-methyl-2-(tetrahydrofuran-2-ylmethyl)isoindolin-1-one | | 420.1 |
| 67 | rac-2-(trans-2-hydroxycyclopentyl)-5-methyl-6-(4-(1-methyl-1H-pyrazol-4-yl)benzyl)isoindolin-1-one | | 402.1 |
| 68 | 5-methyl-6-(4-(1-methyl-1H-pyrazol-4-yl)benzyl)-2-(tetrahydrofuran-2-ylmethyl)isoindolin-1-one | | 402.1 |

TABLE 1-continued
| Ex. No. | IUPAC Name | structure formula | MS |
|---|---|---|---|
| 69 | rac-2-(trans-2-hydroxycyclopentyl)-4,5-dimethyl-6-(4-(1-methyl-1H-pyrazol-4-yl)benzyl)isoindolin-1-one | 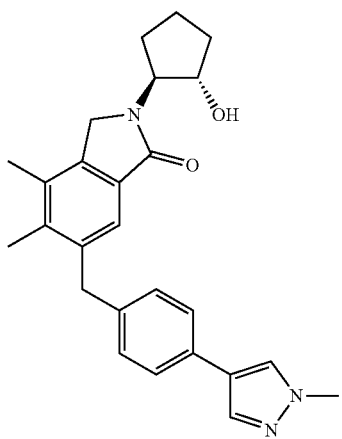 | 416.2 |
| 70 | 6-(2-fluoro-4-(1-methyl-1H-pyrazol-3-yl)benzyl)-4,5-dimethyl-2-(tetrahydrofuran-2-ylmethyl)isoindolin-1-one | 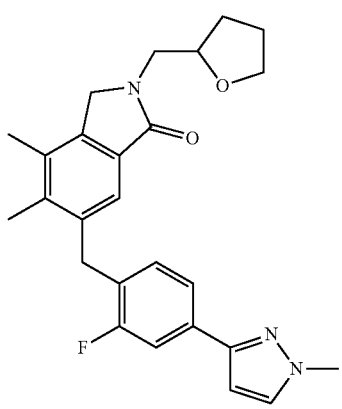 | 434.2 |
| 71 | rac-6-(2-fluoro-4-(1-methyl-1H-pyrazol-3-yl)benzyl)-2-(trans-2-hydroxycyclopentyl)-4,5-dimethylisoindolin-1-one | 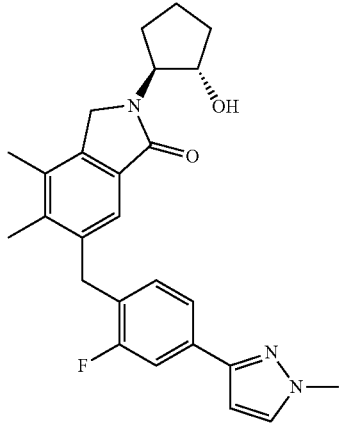 | 434.2 |

TABLE 1-continued

| Ex. No. | IUPAC Name | structure formula | MS |
|---|---|---|---|
| 72 | 4-fluoro-5-methyl-6-(4-(1H-pyrazol-1-yl)benzyl)-2-(tetrahydrofuran-2-ylmethyl)isoindolin-1-one | | 406.1 |
| 73 | rac-5-chloro-2-(trans-2-hydroxycyclopentyl)-6-(4-(1H-pyrazol-1-yl)benzyl)isoindolin-1-one | | 408.1 |
| 74 | 5-chloro-6-(4-(1H-pyrazol-1-yl)benzyl)-2-(tetrahydrofuran-2-ylmethyl)isoindolin-1-one | | 408.1 |

TABLE 1-continued

| Ex. No. | IUPAC Name | structure formula | MS |
|---|---|---|---|
| 75 | rac-5-chloro-2-(trans-2-hydroxycyclohexyl)-6-(4-(1-methyl-1H-pyrazol-4-yl)benzyl)isoindolin-1-one | | 436.1 |
| 76 | rac-5-chloro-2-(trans-2-hydroxycyclopentyl)-6-(4-(1-methyl-1H-pyrazol-4-yl)benzyl)isoindolin-1-one | | 422.0 |
| 77 | 5-chloro-6-(4-(1-methyl-1H-pyrazol-4-yl)benzyl)-2-(tetrahydrofuran-2-ylmethyl)isoindolin-1-one | | 422.0 |

TABLE 1-continued

| Ex. No. | IUPAC Name | structure formula | MS |
|---|---|---|---|
| 78 | rac-4-fluoro-2-(trans-2-hydroxycyclohexyl)-5-methyl-6-(4-(1H-pyrazol-1-yl)benzyl)isoindolin-1-one | | 420.1 |
| 79 | rac-4-fluoro-2-(trans-2-hydroxycyclopentyl)-5-methyl-6-(4-(1H-pyrazol-1-yl)benzyl)isoindolin-1-one | | 406.1 |
| 80 | 4,5-dimethyl-6-(4-(1H-pyrazol-1-yl)benzyl)-2-(tetrahydrofuran-2-ylmethyl)isoindolin-1-one | | 402.1 |

TABLE 1-continued

| Ex. No. | IUPAC Name | structure formula | MS |
|---|---|---|---|
| 81 | 4-methyl-1-oxo-6-(4-(1H-pyrazol-1-yl)benzyl)-2-(tetrahydrofuran-2-ylmethyl)isoindoline-5-carbonitrile | | 413.2 |
| 82 | rac-2-(trans-2-hydroxycyclohexyl)-4,5-dimethyl-6-(4-(1-methyl-1H-pyrazol-3-yl)benzyl)isoindolin-1-one | | 430.2 |
| 83 | rac-2-(trans-2-hydroxycyclopentyl)-4,5-dimethyl-6-(4-(1-methyl-1H-pyrazol-3-yl)benzyl)isoindolin-1-one | | 416.2 |

TABLE 1-continued

| Ex. No. | IUPAC Name | structure formula | MS |
|---|---|---|---|
| 84 | 4,5-dimethyl-6-(4-(1-methyl-1H-pyrazol-4-yl)benzyl)-2-(tetrahydrofuran-2-ylmethyl)isoindolin-1-one | | 416.2 |
| 85 | 4,5-dimethyl-6-(4-(1-nethyl-1H-pyrazol-3-yl)benzyl)-2-(tetrahydrofuran-2-ylmethyl)isoindolin-1-one | | 416.2 |
| 86 | 4-chloro-6-(4-(1H-pyrazol-1-yl)benzyl)-2-(tetrahyarofuran-2-ylmethyl)-5-(trifluoromethyl)isoindolin-1-one | | 476.1 |

TABLE 1-continued

| Ex. No. | IUPAC Name | structure formula | MS |
|---|---|---|---|
| 87 | rac-2-(trans-2-hydroxycyclopentyl)-4-methyl-1-oxo-6-(4-(1H-pyrazol-1-yl)benzyl)isoindoline-5-carbonitrile | | 413.2 |
| 88 | rac-4-chloro-2-(trans-2-hydroxycyclopentyl)-6-(4-(1H-pyrazol-1-yl)benzyl)-5-(trifluoromethyl)isoindolin-1-one | | 476.2 |
| 89 | rac-2-(trans-2-hydroxycyclohexyl)-4,5-dimethyl-6-(4-(1-methyl-1H-pyrazol-4-yl)benzyl)isoindolin-1-one | | 430.2 |

TABLE 1-continued

| Ex. No. | IUPAC Name | structure formula | MS |
|---|---|---|---|
| 90 | 4-chloro-5-methoxy-6-(4-(1H-pyrazol-1-yl)benzyl)-2-(tetrahydrofuran-2-ylmethyl)isoindolin-1-one | | 438.1 |
| 91 | rac-2-(trans-2-hydroxycyclopentyl)-5-methyl-6-(4-(6-methylpyridazin-4-yl)benzyl)isoindolin-1-one | | 414.2 |
| 92 | rac-4-chloro-2-(trans-2-hydroxycyclopentyl)-5-methoxy-6-(4-(1H-pyrazol-1-yl)benzyl)isoindolin-1-one | | 438.1 |

TABLE 1-continued

| Ex. No. | IUPAC Name | structure formula | MS |
|---|---|---|---|
| 93 | rac-4-chloro-2-(trans-2-hydroxycyclohexyl)-5-methyl-6-(4-(1H-pyrazol-1-yl)benzyl)isoindolin-1-one | | 436.1 |
| 94 | rac-6-(4-(1,3-dimethyl-1H-pyrazol-4-yl)-2-fluorobenzyl)-2-(trans-2-hydroxycyclohexyl)-4,5-dimethylisoindolin-1-one | | 462.2 |
| 95 | rac-6-(4-(1,3-dimethyl-1H-pyrazol-4-yl)-2-fluorobenzyl)-2-(trans-2-hydroxycyclopentyl)-4,5-dimethylisoindolin-1-one | | 448.1 |

TABLE 1-continued

| Ex. No. | IUPAC Name | structure formula | MS |
|---|---|---|---|
| 96 | 4-fluoro-5-methoxy-6-(4-(1H-pyrazol-1-yl)benzyl)-2-(tetrahydrofuran-2-ylmethyl)isoindolin-1-one | | 422.1 |
| 97 | rac-4-fluoro-2-(trans-2-hydroxycyclohexyl)-5-methoxy-6-(4-(1H-pyrazol-1-yl)benzyl)isoindolin-1-one | | 436.2 |
| 98 | rac-4-fluoro-2-(trans-2-hydroxycyclopentyl)-5-methoxy-6-(4-(1H-pyrazol-1-yl)benzyl)isoindolin-1-one | | 422.1 |

TABLE 1-continued

| Ex. No. | IUPAC Name | structure formula | MS |
|---|---|---|---|
| 99 | rac-2-(trans-2-hydroxycyclohexyl)-5-methyl-6-(4-(2-methylpyridin-4-yl)benzyl)isoindolin-1-one | | 427.2 |
| 100 | rac-2-(trans-2-hydroxycyclopentyl)-5-methyl-6-(4-(2-methylpyridin-4-yl)benzyl)isoindolin-1-one | | 413.2 |
| 101 | 5-methyl-6-(4-(2-methylpyridin-4-yl)benzyl)-2-(tetrahydrofuran-2-ylmethyl)isoindolin-1-one | | 413.2 |

TABLE 1-continued

| Ex. No. | IUPAC Name | structure formula | MS |
|---|---|---|---|
| 102 | rac-4-chloro-2-(trans-2-hydroxycyclopentyl)-5-methyl-6-(4-(1H-pyrazol-1-yl)benzyl)isoindolin-1-one | | 422.1 |
| 103 | 6-(2-fluoro-4-(1-methyl-1H-1,2,3-triazol-4-yl)benzyl)-4,5-dimethyl-2-(tetrahydrofuran-2-ylmethyl)isoindolin-1-one | | 435.1 |
| 104 | 2-(2-hydroxy-2-methylpropyl)-5-methyl-6-(4-(1H-pyrazol-1-yl)benzyl)isoindolin-1-one | | 376.1 |

TABLE 1-continued

| Ex. No. | IUPAC Name | structure formula | MS |
|---|---|---|---|
| 105 | 5-ethyl-6-(4-(1-methyl-1H-1,2,3-triazol-4-yl)benzyl)-2-(tetrahydrofuran-2-ylmethyl)isoindolin-1-one | | 417.1 |
| 106 | rac-5-ethyl-2-(trans-2-hydroxycyclopentyl)-6-(4-(1-methyl-1H-1,2,3-triazol-4-yl)benzyl)isoindolin-1-one | | 417.1 |
| 107 | 4-fluoro-2-((1S,2S)-2-hydroxycyclopentyl)-5-methyl-6-(4-(1H-pyrazol-1-yl)benzyl)isoindolin-1-one | | 406.1 |

TABLE 1-continued

| Ex. No. | IUPAC Name | structure formula | MS |
|---|---|---|---|
| 108 | 4,5-dimethyl-6-(4-(1-methyl-1H-pyrazol-3-yl)benzyl)-2-((2R)-tetrahydrofuran-2-ylmethyl)isoindolin-1-one | | 416.2 |
| 109 | 4,5-dimethyl-6-(4-(1-methyl-1H-pyrazol-3-yl)benzyl)-2-((2S)-tetrahydrofuran-2-ylmethyl)isoindolin-1-one | | 416.2 |
| 110 | 4,5-dimethyl-6-(4-(1-methyl-1H-1,2,3-triazol-4-yl)benzyl)-2-((2R)-tetrahydrofuran-2-ylmethyl)isoindolin-1-one | | 417.1 |

TABLE 1-continued

| Ex. No. | IUPAC Name | structure formula | MS |
|---|---|---|---|
| 111 | 4-fluoro-2-((1S,2S)-2-hydroxycyclopentyl)-5-methyl-6-(4-(1-methyl-1H-pyrazol-3-yl)benzyl)isoindolin-1-one | | 420.2 |
| 112 | rac-3-fluoro-4-((2-(trans-4-hydroxytetrahydro-2H-pyran-3-yl)-6,7-dimethyl-3-oxo-2,3-dihydro-1H-isoindol-5-yl)methyl)benzonitrile | | 395.2 |
| 113 | rac-3-fluoro-4-((2-(trans-4-hydroxytetrahydro-2H-pyran-3-yl)-6,7-dimethyl-3-oxo-2,3-dihydro-1H-isoindol-5-yl)methyl)benzamide | | 413.2 |

TABLE 1-continued

| Ex. No. | IUPAC Name | structure formula | MS |
|---|---|---|---|
| 114 | 2-(2-hydroxy-2-methylpropyl)-4,5-dimethyl-6-(4-(1-methyl-1H-pyrazol-3-yl)benzyl)isoindolin-1-one | | 404.2 |
| 115 | 6-(2-fluoro-4-(1H-pyrazol-1-yl)benzyl)-4,5-dimethyl-2-((2S)-tetrahydrofuran-2-ylmethyl)isoindolin-1-one | | 420.2 |
| 116 | 5-ethyl-2-[(3S,4S)-4-hydroxytetrahydro-2H-pyran-3-yl]-6-[4-(1-methyl-1H-pyrazol-3-yl)benzyl]-2,3-dihydro-1H-isoindol-1-one<br>Alias; 1,5-anhydro-2,4-dideoxy-2-(5-ethyl-6-(4-(1-methyl-1H-pyrazol-3-yl)benzyl)-1-oxo-1,3-dihydro-2H-isoindol-2-yl)-L-threo-pentitol | | 432.1 |

TABLE 1-continued

| Ex. No. | IUPAC Name | structure formula | MS |
|---|---|---|---|
| 117 | 5-ethyl-2-[(3R,4R)-4-hydroxytetrahydro-2H-pyran-3-yl]-6-[4-(1-methyl-1H-pyrazol-3-yl)benzyl]-2,3-dihydro-1H-isoindol-1-one<br>Alias; 1,5-anhydro-2,4-dideoxy-2-(5-ethyl-6-(4-(1-methyl-1H-pyrazol-3-yl)benzyl)-1-oxo-1,3-dihydro-2H-isoindol-2-yl)-D-threo-pentitol | | 432.1 |
| 118 | 5-ethyl-2-(2-hydroxy-2-methylpropyl)-6-(4-(1-methyl-1H-1,2,3-triazol-4-yl)benzyl)isoindolin-1-one | | 405.1 |
| 119 | 5-ethyl-2-((1S,2S)-2-hydroxycyclopentyl)-6-(4-(1-methyl-1H-1,2,3-triazol-4-yl)benzyl)isoindolin-1-one | | 417.0 |

TABLE 1-continued

| Ex. No. | IUPAC Name | structure formula | MS |
|---|---|---|---|
| 120 | 5-ethyl-2-((1S,2S)-2-hydroxycyclopentyl)-6-(4-(1-methyl-1H-pyrazol-3-yl)benzyl)isoindolin-1-one | | 416.1 |
| 121 | 6-(2-fluoro-4-(1H-pyrazol-1-yl)benzyl)-2-(2-hydroxy-2-methylpropyl)-4,5-dimethylisoindolin-1-one | | 408.1 |
| 122 | 2-((1S,2S)-2-hydroxycyclopentyl)-6-(4-methoxybenzyl)-4,5-dimethylisoindolin-1-one | | 366.1 |

TABLE 1-continued

| Ex. No. | IUPAC Name | structure formula | MS |
|---|---|---|---|
| 123 | 2-fluoro-4-((2-((1S,2S)-2-hydroxycyclopentyl)-6,7-dimethyl-3-oxo-2,3-dihydro-1H-isoindol-5-yl)methyl)-N-methylbenzamide | | 411.1 |
| 124 | 3-fluoro-4-({2-[(3S,4S)-4-hydroxytetrahydro-2H-pyran-3-yl]-6,7-dimethyl-3-oxo-2,3-dihydro-1H-isoindol-5-yl}methyl)benzonitrile Alias; 1,5-anhydro-2-(6-(4-cyano-2-fluorobenzyl)-4,5-dimethyl-1-oxo-1,3-dihydro-2H-isoindol-2-yl)-2,4-dideoxy-L-threo-pentitol | | 395.1 |
| 125 | 3-fluoro-4-((2-((1S,23)-2-hydroxycyclopentyl)-6,7-dimethyl-3-oxo-2,3-dihydro-1H-isoindol-5-yl)methyl)benzonitrile | | 379.2 |

TABLE 1-continued

| Ex. No. | IUPAC Name | structure formula | MS |
|---|---|---|---|
| 126 | 3-fluoro-4-((2-(2-hydroxy-2-methylpropyl)-6,7-dimethyl-3-oxo-2,3-dihydro-1H-isoindol-5-yl)methyl)benzonitrile | | 367.1 |
| 127 | 4-fluoro-2-(2-hydroxy-2-methylpropyl)-5-methyl-6-(4-(1H-pyrazol-1-yl)benzyl)isoindolin-1-one | | 394.1 |
| 128 | 5-ethyl-2-[(3S,4S)-4-hydroxytetrahydro-2H-pyran-3-yl]-6-[4-(1H-pyrazol-1-yl)benzyl]-2,3-dihydro-1H-isoindol-1-one Alias; 1,5-anhydro-2,4-dideoxy-2-(5-ethyl-1-oxo-6-(4-(1H-pyrazol-1-yl)benzyl)-1,3-dihydro-2H-isoindol-2-yl)-L-threo-pentitol | | 418.0 |

TABLE 1-continued

| Ex. No. | IUPAC Name | structure formula | MS |
|---|---|---|---|
| 129 | 5-ethyl-2-(2-hydroxy-2-methylpropyl)-6-(4-(1H-pyrazol-1-yl)benzyl)isoindolin-1-one | | 390.1 |
| 130 | 4-chloro-2-[(3S,4S)-4-hydroxytetrahydro-2H-pyran-3-yl]-5-methyl-6-[4-(1H-pyrazol-1-yl)benzyl]-2,3-dihydro-1H-isoindol-1-one<br>Alias; 1,5-anhydro-2-(4-chloro-5-methyl-1-oxo-6-(4-(1H-pyrazol-1-yl)benzyl)-1,3-dihydro-2H-isoindol-2-yl)-2,4-dideoxy-L-threo-pentitol | | 438.0 |
| 131 | 4-chloro-2-((1S,2S)-2-hydroxycyclopentyl)-5-methyl-6-(4-(1H-pyrazol-1-yl)benzyl)isoindolin-1-one | | 422.0 |

TABLE 1-continued

| Ex. No. | IUPAC Name | structure formula | MS |
|---|---|---|---|
| 132 | 4-chloro-2-(2-hydroxy-2-methylpropyl)-5-methyl-6-(4-(1H-pyrazol-1-yl)benzyl)isoindolin-1-one | | 410.0 |
| 133 | 2-(3-hydroxy-3-methylbutan-2-yl)-5-methyl-6-(4-(1H-pyrazol-1-yl)benzyl)isoindolin-1-one | | 390.1 |
| 134 | 2-((1S,2S)-2-hydroxycyclopentyl)-4,5-dimethyl-6-((6-methylpyridin-3-yl)methyl)isoindolin-1-one | | 351.2 |

TABLE 1-continued

| Ex. No. | IUPAC Name | MS |
|---|---|---|
| 135 | 2-(2-fluorophenyl)-5-methyl-6-(4-(1H-pyruzol-1-yl)benzyl)isoindolin-1-one | 398.0 |
| 136 | 4,5-dimethyl-6-((6-(1H-pyrazol-1-yl)pyridin-3-yl)methyl)-2-((2S)-tetrahydrofuran-2-ylmethyl)isoindolin-1-one | 403.1 |
| 137 | 5-ethyl-2-(2-hydroxy-2-methylpropyl)-6-(4-(1-methyl-1H-pyrazol-3-yl)benzyl)isoindolin-1-one | 404.1 |

TABLE 1-continued

| Ex. No. | IUPAC Name | structure formula | MS |
|---|---|---|---|
| 138 | 2-fluoro-4-((2-(2-hydroxy-2-methylpropyl)-6,7-dimethyl-3-oxo-2,3-dihydro-1H-isoindol-5-yl)methyl)-N-methylbenzamide | | 399.0 |
| 139 | 4-((6,7-dimethyl-3-oxo-2-((2S)-tetrahydrofuran-2-ylmethyl)-2,3-dihydro-1H-isoindol-5-yl)methyl)-2-fluoro-N-methylbenzamide | | 411.1 |
| 140 | 4-fluoro-2-[(3S,4S)-4-hydroxytetrahydro-2H-pyran-3-yl]-5-methyl-6-[4-(1-methyl-1H-pyrazol-3-yl)benzyl]-2,3-dihydro-1H-isoindol-1-one<br>Alias; 1,5-anhydro-2,4-dideoxy-2-(4-fluoro-5-methyl-6-(4-(1-methyl-1H-pyrazol-3-yl)benzyl)-1-oxo-1,3-dihydro-2H-isoindol-2-yl)-L-threo-pentitol | | 436.0 |

TABLE 1-continued

| Ex. No. | IUPAC Name | structure formula | MS |
|---|---|---|---|
| 141 | 2-((1S,2S)-2-hydroxycyclohexyl)-6-(4-methoxybenzyl)-4,5-dimethylisoindolin-1-one | | 380.1 |
| 142 | 6-(4-ethoxybenzyl)-2-[(3S,4S)-4-hydroxytetrahydro-2H-pyran-3-yl]-4,5-dimethyl-2,3-dihydro-1H-isoindol-1-one<br>Alias; 1,5-anhydro-2,4-dideoxy-2-(6-(4-ethoxybenzyl)-4,5-dimethyl-1-oxo-1,3-dihydro-2H-isoindol-2-yl)-L-threo-pentitol | | 396.1 |
| 143 | 2-[(3S,43)-4-hydroxytetrahydro-2H-pyran-3-yl]-4,5-dimethyl-6-[4-(propan-2-yloxy)benzyl]-2,3-dihydro-1H-isoindol-1-one<br>Alias; 1,5-anhydro-2,4-dideoxy-2-(6-(4-isopropoxybenzyl)-4,5-dimethyl-1-oxo-1,3-dihydro-2R-isoindol-2-yl)-L-threo-pentitol | | 410.1 |

TABLE 1-continued

| Ex. No. | IUPAC Name | structure formula | MS |
|---|---|---|---|
| 144 | 5-ethyl-6-[2-fluoro-4-(1H-pyrazol-1-yl)benzyl]-2-[(3S,4S)-4-hydroxytetrahydro-2H-pyran-3-yl]-2,3-dihydro-1H-isoindol-1-one<br>Alias; 1,5-anhydro-2,4-dideoxy-2-(5-ethyl-6-(2-fluoro-4-(1H-pyrazol-1-yl)benzyl)-1-oxo-1,3-dihydro-2H-isoindol-2-yl)-L-threo-pentitol | | 436.2 |
| 145 | 5-ethyl-6-(2-fluoro-4-(1H-pyrazol-1-yl)benzyl)-2-((1S,2S)-2-hydroxycyclopentyl)isoindolin-1-one | | 420.3 |
| 146 | 5-ethyl-6-(2-fluoro-4-(1H-pyrazol-1-yl)benzyl)-2-(2-hydroxy-2-methylpropyl)isoindolin-1-one | | 408.1 |

TABLE 1-continued

| Ex. No. | IUPAC Name | structure formula | MS |
|---|---|---|---|
| 147 | 2-[(3S,4S)-4-hydroxytetrahydro-2H-pyran-3-yl]-4,5-dimethyl-6-[4-(trifluoromethoxy)benzyl]-2,3-dihydro-1H-isoindol-1-one<br>Alias; 1,5-anhydro-2,4-dideoxy-2-(4,5-dimethyl-1-oxo-6-(4-(trifluoromethoxy)benzyl)-1,3-dihydro-2H-isoindol-2-yl)-L-threo-pentitol | | 436.1 |
| 148 | 5-ethyl-2-[(3S,4S)-4-hydroxytetrahydro-2H-pyran-3-yl]-6-(4-methoxybenzyl)-2,3-dihydro-1H-isoindol-1-one<br>Alias; 1,5-anhydro-2,4-dideoxy-2-(5-ethyl-6-(4-methoxybenzyl)-1-oxo-1,3-dihydro-2H-isoindol-2-yl)-L-threo-pentitol | | 382.2 |
| 149 | 6-((6-ethylpyridin-3-yl)methyl)-2-((1S,2S)-2-hydroxycyclohexyl)-4,5-dimethylisoindolin-1-one | | 379.3 |
| 150 | 4-fluoro-2-[(3S,4S)-4-hydroxytetrahydro-2H-pyran-3-yl]-6-(4-methoxybenzyl)-5-methyl-2,3-dihydro-1H-isoindol-1-one<br>Alias; 1,5-anhydro-2,4-dideoxy-2-(4-fluoro-6-(4-methoxybenzyl)-5-methyl-1-oxo-1,3-dihydro-2H-isoindol-2-yl)-L-threo-pentitol | | 386.1 |

TABLE 1-continued

| Ex. No. | IUPAC Name | structure formula | MS |
|---|---|---|---|
| 151 | 4-chloro-2-((1S,2S)-2-hydroxycyclohexyl)-6-(4-methoxybenzyl)-5-methylisoindolin-1-one | | 400.1 |
| 152 | 4-chloro-2-((1S,2S)-2-hydroxycyclopentyl)-6-(4-methoxybenzyl)-5-methylisoindolin-1-one | | 386.1 |
| 153 | 2-(3-fluoropyridin-2-yl)-4,5-dimethyl-6-(4-(1H-pyrazol-1-yl)benzyl)isoindolin-1-one | | 413.1 |

TABLE 1-continued

| Ex. No. | IUPAC Name | structure formula | MS |
|---|---|---|---|
| 154 | 4-fluoro-2-((1S,2S)-2-hydroxycyclohexyl)-6-(4-methoxybenzyl)-5-methylisoindolin-1-one | | 384.2 |
| 155 | 4-((2-((1S,2S)-2-hydroxycyclohexyl)-6,7-dimethyl-3-oxo-2,3-dihydro-1H-isoindol-5-yl)methyl)benzonitrile | | 375.2 |
| 156 | 4-({2-[(3S,4S)-4-hydroxytetrahydro-2H-pyran-3-yl]-6,7-dimethyl-3-oxo-2,3-dihydro-1H-isoindol-5-yl}methyl)benzonitrile Alias; 1,5-anhydro-2-(6-(4-cyanobenzyl)-4,5-dimethyl-1-oxo-1,3-dihydro-2H-isoindol-2-yl)-2,4-dideoxy-L-threo-pentitol | | 377.3 |

TABLE 1-continued

| Ex. No. | IUPAC Name | structure formula | MS |
|---|---|---|---|
| 157 | 4-fluoro-2-[(3S,4S)-4-hydroxytetrahydro-2H-pyran-3-yl]-5-methoxy-6-(4-methoxybenzyl)-2,3-dihydro-1H-isoindol-1-one<br>Alias; 1,5-anhydro-2,4-dideoxy-2-(4-fluoro-5-methoxy-6-(4-methoxybenzyl)-1-oxo-1,3-dihydro-2H-isoindol-2-yl)-L-threo-pentitol | | 402.1 |
| 158 | 6-(3-fluoro-4-methoxybenzyl)-2-[(3S,4S)-4-hydroxytetrahydro-2H-pyran-3-yl]-4,5-dimethyl-2,3-dihydro-1H-isoindol-1-one<br>Alias; 1,5-anhydro-2,4-dideoxy-2-(6-(3-fluoro-4-methoxybenzyl)-4,5-dimethyl-1-oxo-1,3-dihydro-2H-isoindol-2-yl)-L-threo-pentitol | | 400.1 |
| 159 | 2-(2-fluorophenyl)-4,5-dimethyl-6-(4-(1H-pyrazol-1-yl)benzyl)isoindolin-1-one | | 412.2 |

TABLE 1-continued

| Ex. No. | IUPAC Name | structure formula | MS |
|---|---|---|---|
| 160 | 2-[(3S,4S)-4-hydroxytetrahydro-2H-pyran-3-yl]-6-(4-methoxy-3-methylbenzyl)-4,5-dimethyl-2,3-dihydro-1H-isoindol-1-one Alias; 1,5-anhydro-2,4-dideoxy-2-(6-(4-methoxy-3-methylbenzyl)-4,5-dimethyl-1-oxo-1,3-dihydro-2H-isoindol-2-yl)-L-threo-pentitol | | 396.2 |
| 161 | 4-fluoro-2-((1S,2S)-2-hydroxycyclohexyl)-5-methoxy-6-(4-methoxybenzyl)isoindolin-1-one | | 400.2 |
| 162 | 2-(5-chloro-3-fluoropyridin-2-yl)-4,5-dimethyl-6-(4-(1H-pyrazol-1-yl)benzyl)isoindolin-1-one | | 447.1 |

TABLE 1-continued

| Ex. No. | IUPAC Name | MS |
|---|---|---|
| 163 | 6-(2-fluoro-4-methoxybenzyl)-2-[(3S,4S)-4-hydroxytetrahydro-2H-pyran-3-yl]-4,5-dimethyl-2,3-dihydro-1H-isoindol-1-one<br>Alias; 1,5-anhydro-2,4-dideoxy-2-(6-(2-fluoro-4-methoxybenzyl)-4,5-dimethyl-1-oxo-1,3-dihydro-2H-isoindol-2-yl)-L-threo-pentitol | 400.1 |
| 164 | 2-[(3S,4S)-4-hydroxytetrahydro-2H-pyran-3-yl]-6-(4-methoxybenzyl)-5-methyl-2,3-dihydro-1H-isoiridol-1-one<br>Alias; 1,5-anhydro-2,4-dideoxy-2-(6-(4-methoxybenzyl)-5-methyl-1-oxo-1,3-dihydro-2H-isoindol-2-yl)-L-threo-pentitol | 368.2 |
| 165 | rac-2-(trans-4-hydroxytetrahydro-2H-pyran-3-yl)-6-(4-methoxybenzyl)-4,5-dimethyl-2,3-dihydro-1H-isoindol-1-one | 382.2 |
| 166 | 2-[(3S,4S)-4-hydroxytetrahydro-2H-pyran-3-yl]-5-methoxy-6-(4-methoxybenzyl)-4-methyl-2,3-dihydro-1H-isoindol-1-one<br>Alias; 1,5-anhydro-2,4-dideoxy-2-(5-methoxy-6-(4-methoxybenzyl)-4-methyl-1-oxo-1,3-dihydro-2H-isoindol-2-yl)-L-threo-pentitol | 398.2 |

TABLE 1-continued

| Ex. No. | IUPAC Name | structure formula | MS |
|---|---|---|---|
| 167 | 2-((1S,2S)-2-hydroxycyclohexyl)-6-(4-methoxybenzyl)-5-methylisoindolin-1-one | | 366.1 |
| 168 | 2-(3-hydroxy-3-methylbutan-2-yl)-6-(4-methoxybenzyl)-4,5-dimethylisoindolin-1-one | | 368.2 |

Formulation Example 1

| (1) | Compound obtained in Example 1 | 10.0 g |
|---|---|---|
| (2) | Lactose | 60.0 g |
| (3) | Cornstarch | 35.0 g |
| (4) | Gelatin | 3.0 g |
| (5) | Magnesium stearate | 2.0 g |

A mixture of the compound (10.0 g) obtained in Example 1, lactose (60.0 g) and cornstarch (35.0 g) is passed through a 1 mm mesh sieve by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| (1) | Compound obtained in Example 1 | 10.0 g |
|---|---|---|
| (2) | Lactose | 70.0 g |
| (3) | Cornstarch | 50.0 g |
| (4) | Soluble starch | 7.0 g |
| (5) | Magnesium stearate | 3.0 g |

The compound (10.0 g) obtained in Example 1 and magnesium stearate (3.0 g) are granulated using aqueous soluble starch solution (70 mL) (7.0 g as soluble starch), and the obtained granules are dried, and mixed with lactose (70.0 g) and cornstarch (50.0 g). The mixture is compressed to give 1000 tablets.

Experimental Example 1

Measurement of M1 Receptor Positive Allosteric Modulator (M1PAM) Activity

The activity of a test compound in the presence of acetylcholine at EC20 concentration (final concentration 0.6-0.8 nM), which affords an action corresponding to about 20% of the maximum activity, was measured as PAM activity. The method is as follows. CHO-K1 cells stably expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A (Recording medium (DOJINDO LABORATORIES), 0.1% BSA (Wako Pure Chemical Industries, Ltd.), 2.5 μg/mL Fluo-4 AM (DOJINDO LABORATORIES), 0.08% Pluronic F127 (DOJINDO LABORATORIES), 1.25 mM probenecid (DOJINDO LABORATORIES)) containing a calcium indicator was added at 30 μL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 2.4-3.2 nM acetylcholine was added at 10 μL/well, and the fluorescence was measured by FLIPRtetra (Molecular Devices) for 1 min every 1 second. With the definition that the amount of change in the fluorescence on addition of acetylcholine (final concentration 1 µM) is 100% and that on addition of DMSO instead of a test compound is 0%, the activity (%) of the test compound was calculated, and the inflection point in the concentration-dependent curve of the test compound was calculated as IP values. The results are shown in Table 2.

TABLE 2

| Example No. | IP value (nM) | activity (%) at 10 µM |
|---|---|---|
| 1 | 750 | 111 |
| 2 | 86 | 109 |
| 3 | 15 | 106 |
| 4 | 19 | 98 |
| 5 | 8.2 | 102 |
| 6 | 5.3 | 101 |
| 7 | 180 | 107 |
| 8 | 290 | 90 |
| 9 | 43 | 102 |
| 10 | 66 | 106 |
| 11 | 13 | 105 |
| 12 | 7.7 | 91 |
| 13 | 7.9 | 104 |
| 14 | 1.2 | 94 |
| 15 | 11 | 103 |
| 16 | 12 | 94 |
| 17 | 18 | 90 |
| 18 | 10 | 88 |
| 19 | 2 | 101 |
| 20 | 5.5 | 109 |
| 21 | 6.2 | 106 |
| 22 | 32 | 110 |
| 23 | 46 | 100 |
| 24 | 4.3 | 88 |
| 25 | 10 | 90 |
| 26 | 9.2 | 99 |
| 28 | 4.8 | 106 |
| 29 | 9.5 | 102 |
| 32 | 5.6 | 99 |
| 33 | 37 | 95 |
| 34 | 18 | 108 |
| 35 | 3.9 | 103 |
| 36 | 83 | 107 |
| 40 | 37 | 97 |
| 41 | 30 | 97 |
| 42 | 9.2 | 115 |
| 43 | 98 | 110 |
| 47 | 3 | 99 |
| 48 | 31 | 102 |
| 49 | 31 | 97 |
| 51 | 42 | 86 |
| 53 | 28 | 103 |
| 54 | 37 | 92 |
| 55 | 98 | 101 |
| 58 | 95 | 100 |
| 59 | 34 | 100 |
| 60 | 72 | 94 |
| 61 | 35 | 97 |
| 62 | 95 | 103 |
| 63 | 45 | 99 |
| 64 | 22 | 104 |
| 67 | 26 | 93 |
| 68 | 96 | 95 |
| 69 | 13 | 95 |
| 71 | 56 | 100 |
| 75 | 23 | 97 |
| 78 | 8.8 | 95 |
| 79 | 72 | 93 |
| 80 | 14 | 90 |
| 82 | 5.7 | 91 |
| 83 | 13 | 92 |
| 84 | 52 | 104 |
| 85 | 41 | 105 |
| 88 | 85 | 98 |
| 89 | 5.7 | 94 |
| 91 | 38 | 95 |
| 92 | 60 | 91 |
| 93 | 5.6 | 94 |
| 94 | 9.5 | 92 |
| 95 | 26 | 92 |
| 97 | 5.3 | 96 |
| 99 | 16 | 103 |
| 100 | 94 | 101 |
| 102 | 13 | 91 |
| 103 | 6 | 94 |
| 104 | 54 | 101 |
| 105 | 10 | 92 |
| 106 | 11 | 92 |
| 107 | 14 | 102 |
| 109 | 23 | 100 |
| 110 | 24 | 77 |
| 111 | 26 | 103 |
| 112 | 30 | 93 |
| 113 | 1.5 | 82 |
| 114 | 15 | 96 |
| 115 | 25 | 92 |
| 116 | 6.1 | 111 |
| 118 | 25 | 106 |
| 119 | 3.1 | 91 |
| 120 | 25 | 93 |
| 121 | 22 | 89 |
| 123 | 2.1 | 90 |
| 124 | 16 | 86 |
| 125 | 73 | 93 |
| 127 | 59 | 104 |
| 128 | 5 | 97 |
| 129 | 53 | 100 |
| 130 | 2.2 | 94 |
| 131 | 12 | 100 |
| 132 | 7.3 | 87 |
| 133 | 35 | 87 |
| 136 | 75 | 100 |
| 138 | 25 | 106 |
| 139 | 14 | 102 |
| 140 | 2 | 93 |
| 141 | 18 | 106 |
| 142 | 31 | 106 |
| 144 | 23 | 97 |
| 148 | 63 | 89 |
| 149 | 16 | 99 |
| 150 | 14 | 89 |
| 151 | 16 | 92 |
| 152 | 47 | 91 |
| 153 | 57 | 92 |
| 154 | 22 | 100 |
| 155 | 7.1 | 100 |
| 156 | 4.3 | 80 |
| 157 | 84 | 97 |
| 158 | 28 | 111 |
| 160 | 47 | 112 |
| 161 | 32 | 94 |
| 162 | 66 | 95 |
| 163 | 51 | 108 |
| 164 | 62 | 102 |
| 165 | 36 | 103 |
| 167 | 30 | 95 |

Experimental Example 2

Measurement of Myo-Inositol 1 Phosphate (IP1)

Animals used were male Long-Evans rats. They were used after acclimation for at least 1 week. Test compounds were suspended in 0.5% aqueous methylcellulose solution, and the suspension was orally administered to the rats. At a certain period of time after the oral administration, the solution prepared by dissolving lithium chloride in saline was subcutaneously administered into the rats. At a certain period of time after the subcutaneously administration, their bilateral hippocampi were isolated from the rats, and the wet weight thereof was measured. The hippocampi were homogenized with HEPES buffer, followed by centrifugation. The IP1 and protein concentrations in the supernatant were measured by IP-One HTRF assay kit (Cisbio Bioassays) and BCA protein assay kit (Thermo Scientific), respectively. The level of the IP1 production was expressed as the ratio of the concentration of IP1 to that of protein. The increase rate of the IP1 production was shown as a relative value when Vehicle administration group as 100%. The results are shown in Table 3.

TABLE 3

| test compound | increase rate at 10 mg/kg (% of Vehicle) |
|---|---|
| Example 18 | 40 |
| Example 20 | 108 |
| Example 25 | 32 |

Experimental Example 3

Novel Object Recognition Test

Novel object recognition test is comprised of two trials called the acquisition and the retention trials. Scopolamine-induced memory deficits models were used for the test, and animals used were male Long-Evans rats (7-week-old). On the day before the test, for acclimation, the rats were allowed to freely move about the test box (40×40×50 cm) for 10 minutes. On the test day, the rats were acclimated to the test room for about 1 hr prior to the test. The test compounds were orally administered to the rats in a single dose 2 hr before the acquisition trial. For induction of learning and memory deficits, scopolamine (0.1 mg/kg) was subcutaneously administered into the rats 30 min before the acquisition trial. For the acquisition trial, two identical objects (A1, A2) were placed in the test box. The rats were put in the test box for 3 min, and the duration exploring each object was measured. The retention trial was performed 4 hr after the acquisition trial. For the retention trial, the familiar object (A3) used for the acquisition trial and the novel object (B) different shape from A3 were placed in the test box. The rats were put in the test box for 3 min. The duration exploring each object in the acquisition trial and the retention trial, and the exploration rate (%) of novel object was calculated. The exploration rate (%) of novel object was expressed as (the duration exploring the novel object)/[(the duration exploring the novel object)+(the duration exploring the familiar object)]×100(%) at mean±standard error. The results are shown below.

exploration rate (%) of novel object
control: 63.35±1.59%
solvent-scopolamine group: 52.08±2.47%
Example 18 (3 mg/kg)-scopolamine group: 59.11±3.87%
control: 66.4±2.3%
solvent-scopolamine group: 50.4±2.4%
Example 20 (3 mg/kg)-scopolamine group: 61.2±3.1%
control: 62.37±3.24%
solvent-scopolamine group: 48.39±2.01%
Example 25 (10 mg/kg)-scopolamine group: 57.55±5.03%

INDUSTRIAL APPLICABILITY

The compound of the present invention is useful as a cholinergic muscarinic M1 receptor positive allosteric modulator, or a medicament such as an agent for the prophylaxis or treatment of Alzheimer's disease, schizophrenia, pain, sleep disorder, Parkinson's disease dementia, dementia with Lewy bodies and the like.

This application is based on patent application No. 2014-089585 filed on Apr. 23, 2014 in Japan, the contents of which are encompassed in full herein.

The invention claimed is:

1. 2-[(3S,4S)-4-Hydroxytetrahydro-2H-pyran-3-yl]-6-(4-methoxybenzyl)-4,5-dimethyl-2,3-dihydro-1H-isoindol-1-one, or a salt thereof.

2. A medicament comprising 2-[(3S,4S)-4-hydroxytetrahydro-2H-pyran-3-yl]-6-(4-methoxybenzyl)-4,5-dimethyl-2,3-dihydro-1H-isoindol-1-one or a salt thereof, and a pharmaceutically acceptable carrier.

* * * * *